(12) United States Patent
Kragler et al.

(10) Patent No.: US 11,981,901 B2
(45) Date of Patent: May 14, 2024

(54) METHOD FOR CHANGING THE INTERCELLULAR MOBILITY OF AN MRNA

(71) Applicant: Rijk Zwaan Zaadteelt en Zaadhandel B.V., De Lier (NL)

(72) Inventors: Friedrich Kragler, Potsdam (DE); Wenna Zhang, Potsdam (DE); Wim Verelst, De Lier (NL)

(73) Assignee: Rijk Zwaan Zaadteelt en Zaadhandel B.V., De Lier (NL)

( * ) Notice: Subject to any disclaimer, the term of this patent is extended or adjusted under 35 U.S.C. 154(b) by 3 days.

(21) Appl. No.: 17/446,931

(22) Filed: Sep. 3, 2021

(65) Prior Publication Data

US 2022/0056462 A1 Feb. 24, 2022

Related U.S. Application Data

(63) Continuation of application No. 16/093,772, filed as application No. PCT/EP2017/059029 on Apr. 13, 2017, now Pat. No. 11,142,771.

(30) Foreign Application Priority Data

Apr. 14, 2016 (WO) .................. PCT/EP2016/058282

(51) Int. Cl.
C12N 15/82 (2006.01)
C12N 15/10 (2006.01)

(52) U.S. Cl.
CPC ....... *C12N 15/8216* (2013.01); *C12N 15/102* (2013.01); *C12N 15/8289* (2013.01)

(58) Field of Classification Search
None
See application file for complete search history.

(56) References Cited

U.S. PATENT DOCUMENTS

| | | | | |
|---|---|---|---|---|
| 7,579,150 | B1 * | 8/2009 | Hannapel | C12N 15/8261 435/6.13 |
| 10,351,865 | B2 * | 7/2019 | Kragler | C12N 15/8216 |
| 11,142,771 | B2 * | 10/2021 | Kragler | C12N 15/8216 |

FOREIGN PATENT DOCUMENTS

| | | |
|---|---|---|
| EP | 2918161 A1 | 9/2015 |
| WO | WO-2013/017683 A1 | 2/2013 |
| WO | WO-2015/200539 A1 | 12/2015 |

OTHER PUBLICATIONS

Zhang et al., 2016, The Plant Cell, 28:1237-1249.*
Calderood et al., 2016, The Plant Cell, 28:610-615.*
Li et al., 2009, Journal of Virology, 83:3540-3548.*
Xia et al., 2018, Plant Physiology, 177:745-758.*
Alonso et al. (2003) "Genome-wide insertional mutagenesis of *Arabidopsis thaliana*," Science. 301:653-657.
Barends et al. (2004) "tRNA-like structure regulates translation of Brome mosaic virus RNA," J. Virol. 78 (8):4003-4010.
Calderwood et al., (2016) The Plant Cell, 28:610-615.
Chen et al. (1998) "Control of dissected leaf morphology by a Cys(2)His(2) zinc finger transcription factor in the model legume *Medicago truncatula*," Proc. Natl. Acad. Sci. USA. 107(23):10754-10759.
Cho et al. (Aug. 17, 2015) "Polypyrimidine tract-binding proteins of potato mediate tuberization through an interaction with StBEL5 RNA," J. Exp. Bot. 66:6835-6847.
Curtis et al. (2003) "A gateway cloning vector set for high-throughput functional analysis of genes in planta," Plant Physiol. 133:462-469.
Dobin et al. (Oct. 25, 2012) "STAR: ultrafast universal RNA-seq aligner," Bioinformatics. 29(1):15-21.
Goodenbour et al., (2006) Nucleic Acids Research, 34:6137-6146.
Huang et al. (2009) "The sequences of Arabidopsis GA-Insensitive RNA constitute the motifs that are necessary and sufficient for RNA long-distance trafficking," The Plant Journal. 59:921-929.
International Search Report with Written Opinion for PCT/EP2017/059029 dated Jun. 19, 2017.
Jinek et al. (2012) "A Programmable Dual-RNA-Guided DNA Endonuclease in Adaptive Bacterial Immunity," Science. 337:816-821.
Juhling et al. (2009) "tRNAdb 2009: compilation of tRNA sequences and tRNA genes," Nucleic Acids Res. 37:D159-D162.
Koh et al. (May 5, 2014) "Noninvasive in vivo monitoring of tissue-specific global gene expression in humans," Proc. Natl. Acad. Sci. USA. 111:7361-7366.
Kragler (2010) "RNA in the phloem: A crisis or a return on investment?" Plant Sci. 178:99-104.
Lamesch et al. (2012) "The *Arabidopsis* Information Resource (TAIR): improved gene annotation and new tools," Nucleic Acids Res. 40:01202-1210.

(Continued)

*Primary Examiner* — Jason Deveau Rosen
(74) *Attorney, Agent, or Firm* — Dechert LLP

(57) ABSTRACT

The present invention relates to a method for changing the intercellular mobility of an m RNA of a gene in an organism, comprising: modifying a t RNA-like structure present in the m RNA by mutating the gene from which the m RNA is transcribed, or including the sequence of a t RNA-like structure in the transcribed part of the gene. The method is in particular suited for plants. The intercellular mobility can be between different organs. Mutating the gene is for example for inducing loss of mobility of the transcript and comprises deleting the sequence of the tRNA-like structure from the gene, mutating the sequence of the t RNA-like structure to change the tridimensional configuration thereof, or inserting a genetic element into the gene to remove the tRNA-like structure from the transcribed part of the gene, or for inducing a change in the destination of the transcript and comprises modifying the sequence of the t RNA-like structure from the gene such that the transcript is addressed to a location different from the original destination of the transcript.

Figure 1A:
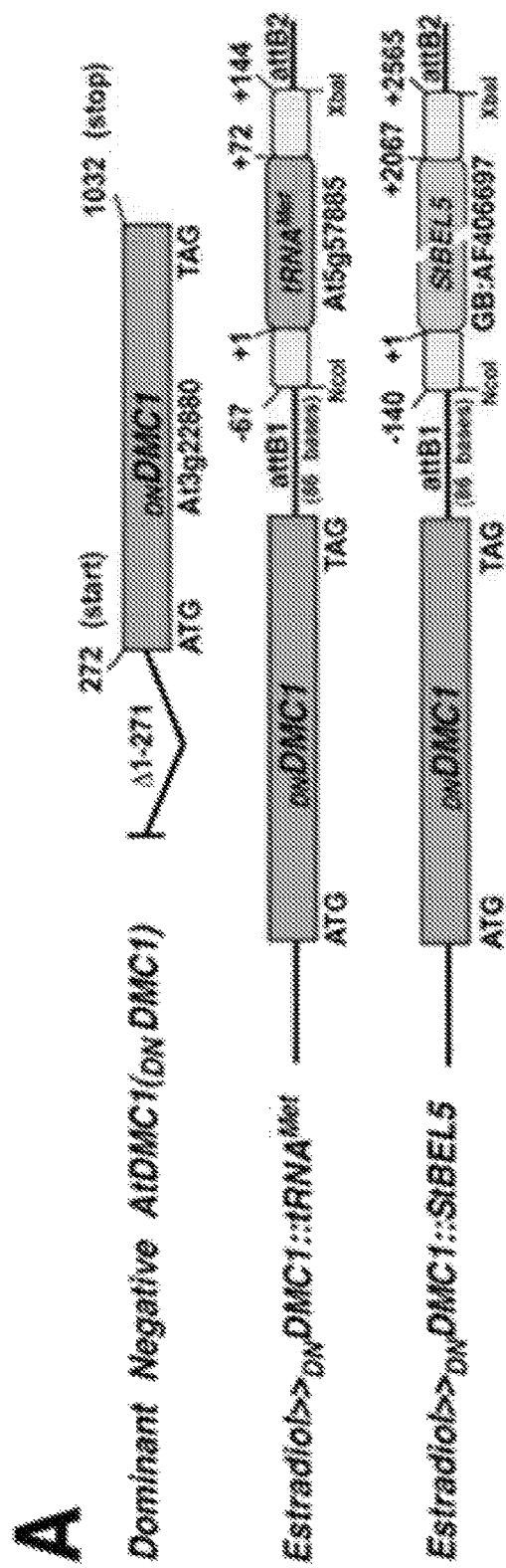
Figure 1B:
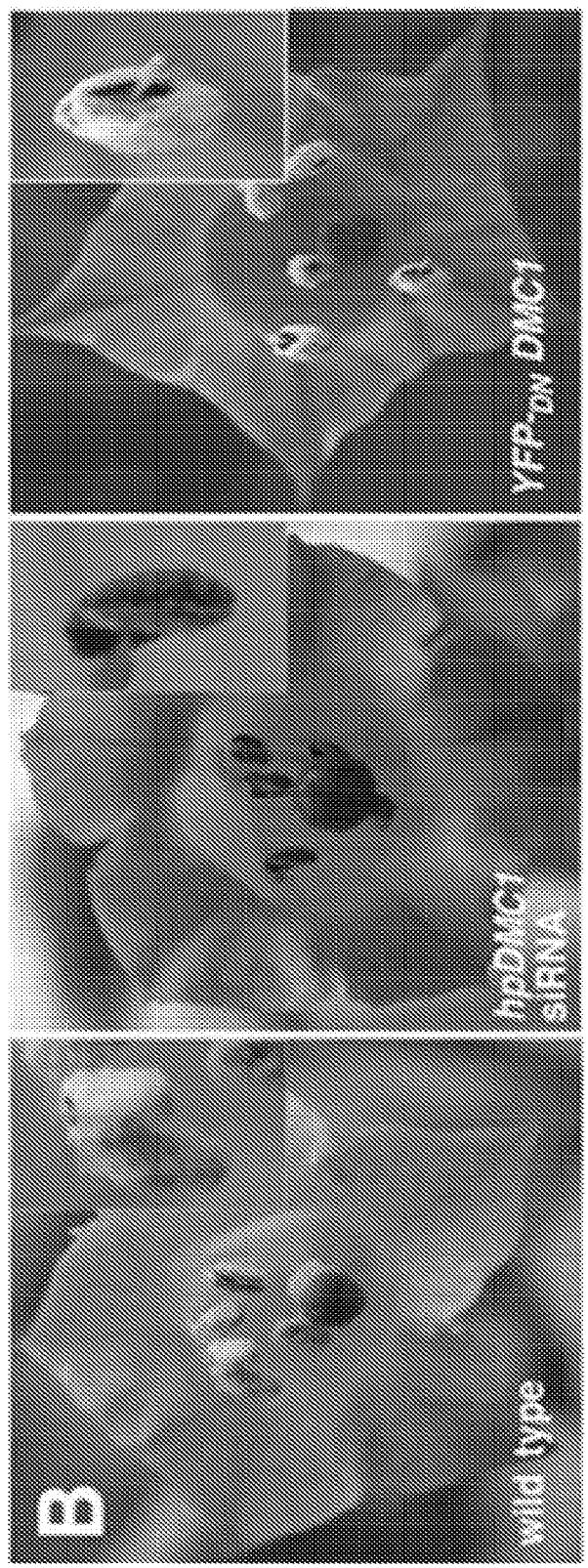
Figure 1C:
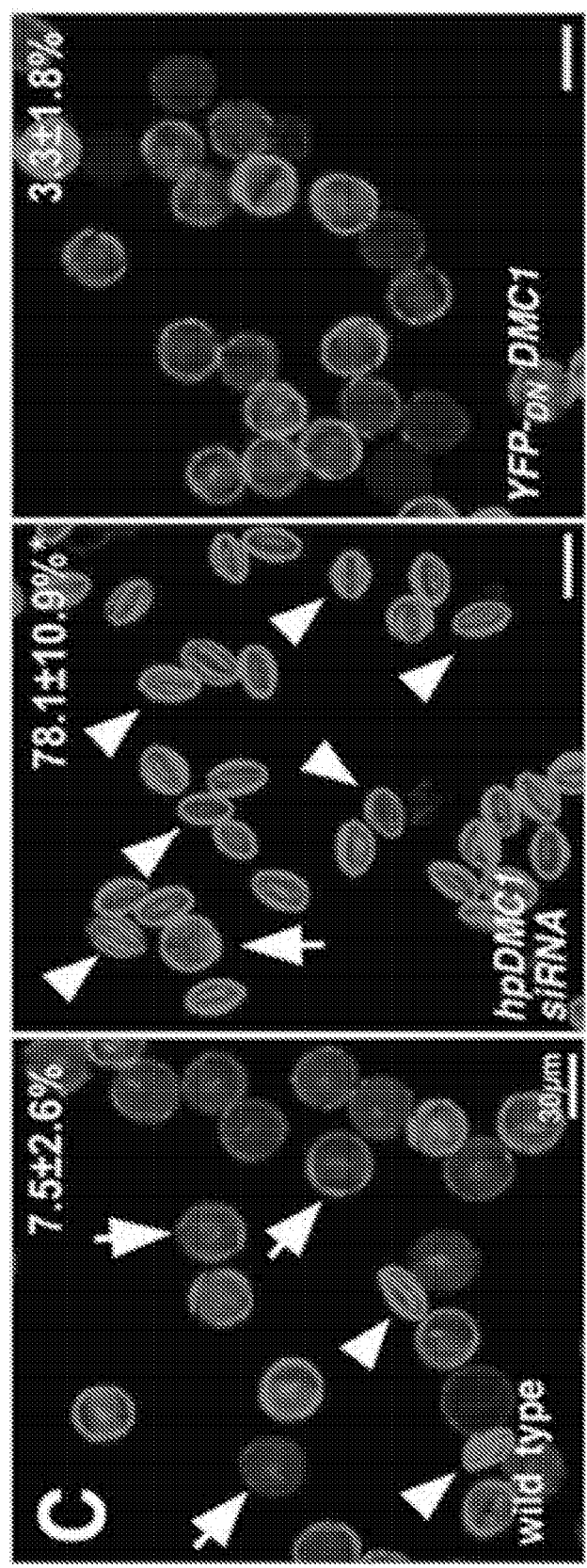
Figure 1D:
Figure 1E:
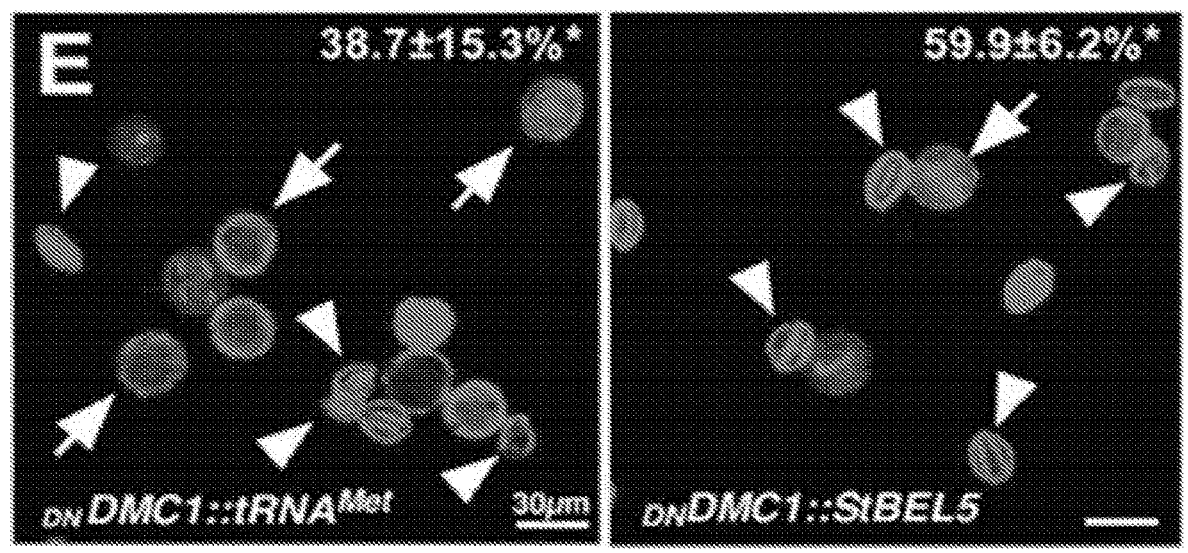
Figure 1F:
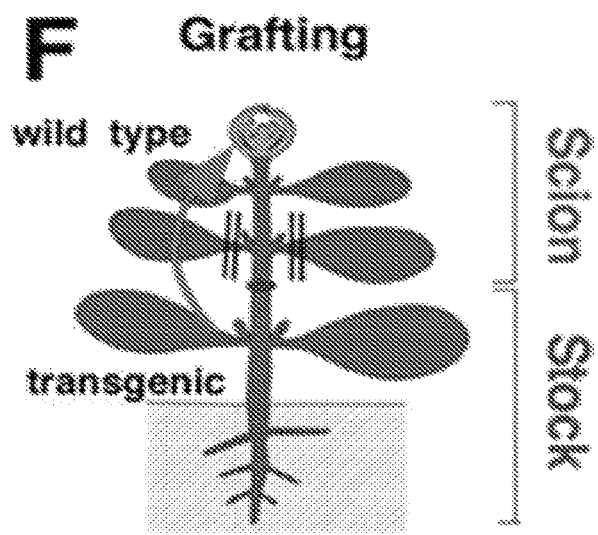
Figure 1G:
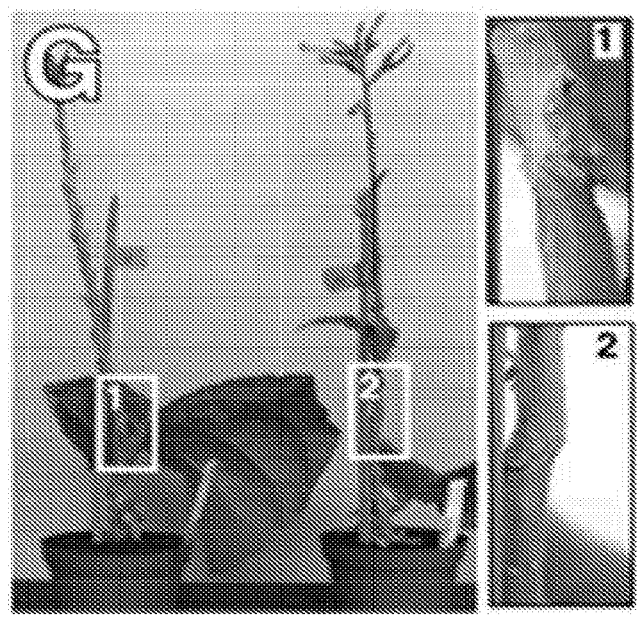

31 Claims, 32 Drawing Sheets
Specification includes a Sequence Listing.

(56) References Cited

OTHER PUBLICATIONS

Li et al. (2009) "A cis element within flowering locus T mRNA determines its mobility and facilitates trafficking of heterologous viral RNA," J. Viral. 83(8):3540-3548.

Li et al. (2011) "Mobile FT mRNA contributes to the systemic florigen signalling in floral induction," Scientific Reports. 1:73. pp. 1-6.

Lohse et al. (Jun. 8, 2012) "RobiNA: a user-friendly, integrated software solution for RNA-Seq-based transcriptomics," Nucleic Acids Res. 40:W622-W627.

Lu et al. (May 1, 2012) "Long-distance movement of *Arabidopsis* Flowering Locust RNA participates in systemic floral regulation," RNA Biology. 9(5):653-662.

Mach et al. (Jun. 17, 2016) "Ticket to Ride: tRNA-Related Sequences and Systemic Movement of mRNAs," The Plant Cell. 28:1231-1232.

Macke et al. (2001) "RNAMotif, an RNA secondary structure definition and search algorithm," Nucleic Acids Res. 29:4724-4735.

Maniataki et al. (2003) "Viroid RNA systemic spread may depend on the interaction of a 71-nucleotide bulged hairpin with the host protein VirP1," RNA. 9:346-354.

Nisar et al. (Dec. 19, 2012) "Inflorescence stem grafting made easy in *Arabidopsis*," Plant Methods. 8:50. pp. 1-8.

Probst et al. (2007) "Spontaneous cellular uptake of exogenous messenger RNA in vivo is nucleic acid-specific, saturable and ion dependent," Gene Ther. 14:1175-1180.

Takeda et al. (2011) "A Three-Dimensional RNA Motif in Potato spindle tuber viroid Mediates Trafficking from Palisade Mesophyll to Spongy Mesophyll in Nicotiana benthamiana," The Plant Cell. 23:258-272.

Tani et al. (2007) "Circulating cell-free mRNA in plasma as a tumor marker for patients with primary and recurrent gastric cancer," Anticancer Res. 27:1207-1212.

Thieme et al. (2015) "Endogenous *Arabidopsis* messenger RNAs transported to distant tissues," Nat. Plants. 1:15025. pp. 1-8.

Woo et al. (Oct. 19, 2015) "DNA-free genome editing in plants with preassembled CRISPR-Cas9 ribonucleoproteins," Nat. Biotechnol. 33:1162-1164.

Zaretsky et al. (2006) "MUC1 gene overexpressed in breast cancer: structure and transcriptional activity of the MUC1 promoter and role of estrogen receptor alpha (ERa) in regulation of the MUC1 gene expression," Mal. Cancer. 5:57. pp. 1-14.

Zhang et al. (2009) "The Phloem-Delivered RNA Pool Contains Small Noncoding RNAs and Interferes with Translation," Plant Physiol. 150:378-387.

Zhang et al. (Apr. 4, 2016) "Vascular-mediated signalling involved in early phosphate stress response in plants," Nat. Plants. 2:16033. pp. 1-9.

Zhang et al. (Aug. 14, 2014) "Graft-transmissible movement of inverted-repeat-induced siRNA signals into flowers," The Plant Journal. 80:106-121.

Zhang et al. (Jun. 7, 2016) "tRNA-Related Sequences Trigger Systemic mRNA Transport in Plants," The Plant Cell. 28:1237-1249.

Zhong et al. (2008) "A Genomic Map of Viroid RNA Motifs Critical for Replication and Systemic Trafficking," The Plant Cell. 20:35-47.

* cited by examiner

D Arabidopsis *CHOLINE KINASE 1 (CK1)*

E *CK1::tRNA^Gly* detection after grafting

METHOD FOR CHANGING THE INTERCELLULAR MOBILITY OF AN MRNA

CROSS-REFERENCE TO RELATED APPLICATIONS

This application is a Continuation of application Ser. No. 16/093,772 filed on Oct. 15, 2018, which is a 35 U.S.C. § 371 filing of International Patent Application No. PCT/EP2017/059029, filed Apr. 13, 2017, which claims priority to International Patent Application No. PCT/EP2016/058282, filed Apr. 14, 2016, the entire contents of which are incorporated herein by reference.

FIELD OF THE INVENTION

The present invention relates to a method for changing the intercellular mobility of an mRNA of a gene in an organism.

BACKGROUND

One of the most fundamental principles in biology is the relationship between DNA, RNA and proteins. Generally, in eukaryotic organisms, DNA comprises genes, which can be transcribed into messenger RNA (mRNA) molecules, and these mRNA molecules are subsequently translated into proteins. These different steps take place at different locations in a eukaryotic cell: the DNA is contained inside an organelle which is located inside the cytoplasm of a eukaryotic cell (i.e. a nucleus, mitochondrion or chloroplast). However, the mRNA transcript needs to be exported out of that organelle, because translation typically takes place in the cytoplasm of the cell, which is where the ribosomes required for translation are located.

Thus, it is fundamental for the normal functioning of biological systems that mRNA transcripts are transported across organellar membranes, from one subcellular compartment to another subcellular compartment. In this manner, a cell's genetic information is efficiently translated into a large number of different proteins that work together to enable the cell to maintain its own functionality and metabolism, and to respond adequately to its environment and to signals from other cells in the organism, and to signals from the organism's environment. This so-called cell-autonomy thus leads to a situation in which a cell's phenotype and behaviour is directly linked to that cell's own genetic information, in a multicellular organism.

However, researchers have also observed cases of non-cell-autonomy, wherein one cell influences the phenotype of another cell. In a multicellular organism, different cells communicate with each other, and thus they influence and coordinate each other's behaviour and phenotype. In some cases, a mutation present in the genome of one cell may even influence the phenotype of another cell that does not have said mutation in its genome.

A good example of non-cell-autonomy has been observed in plants. In the phloem sap of plants, many protein-coding mRNA transcripts, small RNA molecules and proteins have been detected that can move from one location in the plant to another location. Thus, in some instances one cell produces an mRNA transcript, and then exports it to another cell, where the mRNA transcript may be translated into a protein, and where the protein fulfils its function. This exchange of information over long distances, from one cell-type, tissue or organ to another via the vascular tissue, is very poorly understood, but it provides a new level of complexity in how plants function, how they coordinate their own development and growth, and how their organs exhibit a concerted response to the plant's environment. It reveals that cells and organs in different parts of the organism communicate with each other, not only by means of small signalling molecules such as hormones, but also by exchanging macromolecules in a coordinated manner. The mode of action of this system (RNA motifs that trigger mobility, the extent of their transport, and their potential to be translated into functional proteins after transport) is however unknown in the prior art.

In the research leading to the present invention, it was observed that many mRNA transcripts that are present in the phloem sap of plants (and that are enriched in the pool of mRNA transcripts that move across chimeric graft junctions) comprise a tRNA-like structure (TLS). It was demonstrated that tRNA-like structures are sufficient to mobilise mRNA transcripts, by showing that mRNAs harbouring distinctive TLS move from transgenic roots into wild-type leaves and from transgenic leaves into wild-type flowers or roots, when wild-type and transgenic plants are grafted onto each other. It was furthermore shown that these mobile mRNA transcripts are translated into proteins after their transport. It was also found that bicistronic mRNA::tRNA transcripts (i.e. mRNA transcripts harbouring a TLS) are frequently produced in *Arabidopsis thaliana*, and that they are enriched in the population of graft-mobile mRNAs. "Graft-mobile mRNAs" are mRNAs that are capable of moving across a graft junction.

RNA molecules are arguably the most functionally diverse biological macromolecules found in cells, and their diverse roles are determined by both their complex three-dimensional structure and by their primary sequence. An additional biological role of tRNA sequences (or tRNA-like structures, TLSs) has now been uncovered in plants: they harbour a motif mediating mRNA transport to distant plant cells. Interestingly, transcript mobility was induced by tRNA$^{Met}$ and tRNA$^{Gly}$, but not by one particular tRNA$^{Ile}$, which correlates with the absence of this tRNA$^{Ile}$ in pumpkin phloem sap. As the present results indicate that transcript mobility is mediated by a particular RNA structure, a tRNA motif-scanning algorithm did indeed reveal that a significantly high number of identified mobile mRNAs harbours a TLS motif or is transcribed by genes in close proximity of annotated tRNA genes which seem to frequently produce bicistronic poly(A)-RNA::tRNAs.

While the functional role of many mobile mRNAs in distant tissues remains to be elucidated, evidence supports the notion that trafficking of small si/miRNA and large mRNAs via the phloem plays an important role in regulating plant development. A surprisingly high number of mRNAs is present in phloem exudates and was shown to move across graft junctions, but no general and easily predictable RNA motif or conserved sequence mediating mobility could be identified in the graft-mobile transcript populations. However, the present invention now demonstrates that a significant fraction of mobile mRNAs carries a TLS motif that mediates mobility across graft junctions.

Messenger RNA transfer does not strictly follow the source to sink phloem flow, as it could be demonstrated that GUS::tRNA fusions not only move from shoot (source) to root (sink), but also vice versa. Two transport pathways were found to exist for delivering mRNA molecules. One is based on passive, non-selective delivery from source to sink via the phloem vessels. However, according to the invention also another pathway in form of a targeted and active transport system was found. This pathway inter alia mediates the delivery of mRNAs from root to shoot. Presence of an active mRNA delivery mechanism is supported by two findings according to the invention, namely that sequences derived from TLS are sufficient to confer mobility to heterologous mRNAs, and that deletion of a TLS in the plant endogenous CK1:tRNA$^{Gly}$ bicistronic transcript, which is naturally mobile, makes it immobile.

It was shown according to the invention that TLSs or closely related RNA structures mediate transport of a number of graft-mobile transcripts, and that specific tRNA sequences such as tRNA$^{Gly}$-, tRNA$^{Met}$-, and tRNA$^{Met}$-derived sequences trigger transport of otherwise non-mobile transcripts, and that a significant number of mobile mRNAs harbour a TLS motif.

The invention is thus based on the fact that this structural motif (TLS, with predicted stem-bulge-loop structures that are identical or very similar to a tRNA) plays a role in the coordinated long-distance transport of mRNA transcripts.

In animals, evidence for long-distance intercellular mRNA transport also exists. In human plasma, for example, the presence of cell-free mRNA of the hTERT and MUC1 genes has been found to correlate with gastric cancer (Tani et al., 2007, *Anticancer Res.* 27: 1207-1212). Both genes have been linked to oncogenesis in humans. It is conceivable that the occurrence of cell-free mRNA of these genes in plasma represents a mode of communication between cancer cells and healthy cells. If healthy cells have a means of uptake for these mRNA transcripts, they may start producing the encoded proteins Mammalian cells have been reported to be capable of taking up exogenous mRNA (see, for example, Probst et al., 2007, *Gene Ther.* 14: 1175-1180). Various mutations in hTERT have been linked to an increased risk of various cancers, and by sending out mRNA transcripts comprising such mutation, one single cell carrying an oncogenic mutation in its genome (e.g. as the result of a non-inherited de novo mutation) may have the capacity to distribute its mutated version of the mRNA transcript to many other cells that may not harbour said mutation in their own genome, but that are receptive for taking up said transcript from the extracellular matrix. In such a manner, healthy cells will produce a mutant (and potentially oncogenic) form of the encoded protein, even when their own, endogenous gene coding for that protein is not mutated. In the case of MUC1, it has been shown that up-regulation of this gene is associated with cancer (Zaretsky et al., 2006, *Mol. Cancer* 5: 57). Here again, the presence of mRNA transcripts of this gene in blood plasma would provide an opportunity for cells to take up these cell-free mRNA transcripts and to produce the proteins encoded thereby, independently of the promoter activity of their own, endogenous MUC1 gene. This may lead to a higher than normal production of this protein in many cells in the plasma, which, in turn, may be linked to oncogenesis.

The occurrence of disease-specific mRNA transcripts in blood has also been observed in, for example, patients with the neurodegenerative disorder Alzheimer's disease (Koh et al., 2014, *Proc. Nat. Acad. Sci. USA* 111: 7361-7366). This mRNA secretion from neurons may represent a way in which this disorder progresses and spreads between the neurons of a patient.

In animal cells, proteins and RNA may be secreted from cells through vesicles in an unconventional secretion mechanism, which is different from the Endoplasmic Reticulum (ER)/Golgi pathway. It is possible that TLSs play a role in the selective loading of mRNA transcripts into vesicles and/or in the specific secretion of mRNA from cells into the extracellular matrix (e.g. blood, plasma). If the presence of a TLS also enables an mRNA transcript to be taken up by other cells, said TLS would essentially mediate cell-to-cell movement of mRNA transcripts in animals, similarly to what has been observed in plants in the research leading to the present invention.

The invention thus relates to a method for changing the intercellular mobility of an mRNA of a gene in an organism, comprising:
  modifying a tRNA-like structure (TLS) present in the mRNA by mutating the gene from which the mRNA is transcribed, or
  including the sequence of a tRNA-like structure (TLS) in the transcribed part of the gene.

There are essentially three ways in which the present invention can be applied to change the intercellular mobility of an mRNA of a gene in an organism. On the one hand, the mobility of an mRNA transcript that is mobile in a wild-type organism can be prevented, by modifying the tRNA-like structure that is naturally present in said mRNA transcript in such a way that it no longer promotes mobility of the mRNA transcript.

On the other hand, an mRNA transcript that is not mobile in a wild-type organism can be made mobile, by providing said mRNA transcript with one or more tRNA-like structures that have the ability to promote mobility of the mRNA transcript. This embodiment can be applied to mRNA transcripts from genes that are endogenous to the organism, but also to mRNA transcripts from genes that are not endogenous to the organism, such as genes that have been introduced into the organism's genome by means of genetic modification, or that have been introduced into the organism in a transient manner, e.g. by injection, ingestion, transfection, or by exogenous application of mRNA molecules comprising a TLS on the organism's surface, and that are subsequently transported further inside the organism and imported into cells by virtue of the presence of said TLS.

In a third embodiment, the mobility of an mRNA transcript can be changed in the sense that the destination of the transcript inside the organism (i.e. the cell-type, tissue or organ where the mRNA transcript moves towards in a wild-type organism) changes as a result of modifications in the TLS. In case different destinations in the organism are linked to different TLSs, modifying the original TLS of an mRNA can direct the transcript to a different destination inside the organism, which results in an ectopic production of the encoded protein.

Modification of TLSs and inclusion of such TLSs in transcripts can be achieved by means of genetic modification. Genetic modification comprises transgenic modification or transgenesis, using a gene from a non-crossable species or a synthetic gene, and cisgenic modification or cisgenesis, using a natural gene, coding for a trait from the organism itself or from a sexually compatible donor organism.

In one embodiment, the organism of which the intercellular mobility of the mRNA of a gene is to be changed is a multicellular eukaryotic organism, such as a plant, a fungus, or an animal. In a further embodiment, the organism is a dicotyledonous plant, a monocotyledonous plant, a gymnosperm, a bryophyte, an algae, a mammal, a non-mammalian vertebrate animal, or an invertebrate animal.

In the context of this invention, the term "organism" is intended to not only comprise living multicellular plants, animals and fungi, but also tissue cultures and cell cultures that have been derived from living multicellular plants, animals and fungi. Just like a living organism, said tissue cultures or cell cultures consist of multiple cells, between which cells mRNA can be exchanged.

According to a first aspect of the invention, said organism is a plant. In one embodiment, the organism is a plant belonging to one of the following plant genera, or a cell culture or tissue culture derived therefrom: *Allium, Apium, Beta, Brassica, Capsicum, Cichorium, Citrullus, Cucumis, Cucurbita, Benincasa, Daucus, Eruca, Lactuca, Lagenaria, Luffa, Phaseolus, Pisum, Lens, Raphanus, Solanum, Spinacia, Valerianella, Nicotiana, Petunia, Arabidopsis, Capsella, Arabis, Cardamine, Malus, Pyrus, Prunus, Vitis, Rosa, Fragaria, Populus, Fagus, Pinus, Picea, Ginkgo, Larix, Betula, Quercus, Salix, Alnus, Corylus, Amygdalus, Vaccinium, Rubus, Persea, Citrus, Castanea, Acer, Fraxinus, Coffea, Camellia, Theobroma, Olea, Cicer, Juglans, Pistacia, Arachis, Anacardium, Macadamia, Ficus, Litchi, Actinidia, Bougainvillea, Helianthus, Hibiscus, Malva, Glycine, Gossypium, Cannabis, Stevia, Opuntia, Ipomoea, Manihot, Humulus, Acacia, Medicago, Trifolium, Lotus, Vicia, Linum, Fagopyrum, Zea, Triticum, Avena, Hordeum, Oryza, Zizania, Secale, Triticosecale, Sorghum, Bambusa, Dendrocalamus, Saccharum, Cymbopogon, Pennisetum, Panicum, Festuca, Lolium, Phleum, Poa, Miscanthus, Asparagus, Agave, Yucca, Cocos, Elaeis, Phoenix, Amaryllis, Narcissus, Aloe, Canna, Iris, Colchicum, Crocus, Gladiolus, Juncus, Lilium, Tulipa, Musa, Dendrobium, Phalaenopsis, Vanilla, Typha, Zingiber, Curcuma, Lemna*. Cell cultures and tissue cultures derived from plants include, for example, microspore cultures, pollen cultures, callus cultures, root cultures, meristem cultures, protoplast cultures, mesophyll cell cultures, tissue or organ explants, and the BY-2 cell culture.

According to a second aspect of the invention, said organism is an animal. In one embodiment, said organism is a mammal, a non-mammalian vertebrate animal, or an invertebrate animal. In a further embodiment, the organism is a mammal belonging to one of the following genera, or a cell culture or a tissue culture derived therefrom: *Mus, Homo, Rattus, Pan, Cricetus, Mesocricetus, Cavia, Canis, Oryctolagus* Mammalian cell cultures often used in research are, for example, CHO, HeLa, HEK293, HL-60, J558L, JY, K562, KBM-7, RBL, and COS-1.

In one embodiment, the intercellular mobility is between cells in the same organ of an organism, or between cells in the same tissue culture or cell culture. In this context, the concept of an "organ" also comprises, for example, the blood and lymph of animals. In another embodiment, the intercellular mobility is between cells in different organs of an organism.

Intercellular mobility of an mRNA of a gene in an organism may occur across the plasma membranes of neighbouring cells in a tissue, or it may occur across the plasma membranes of cells that are not positioned adjacent to each other in a tissue. In the latter embodiment, said mobility may take advantage of the organism's own means for long-distance transport and cell-to-cell communication and/or of the extracellular matrix, such as the vascular tissue (phloem and/or xylem) or the apoplast in plants, or the blood stream or lymphatic system in animals. Cells that are not positioned adjacent to each other in a tissue may for example be cells that belong to different tissues or organs in the organism, or cells that are not attached or connected to other cells, such as blood cells in an animal, pollen grains in a plant's anther, etcetera.

In the course of normal development and growth, the exchange of mRNA transcripts between cells appears to be commonplace. It may however also be a phenomenon that plays an important role in the establishment and/or progression of disease or in the organism's defence against disease, as it allows the transport of genetic material—in the form of an already transcribed mRNA—from one cell to other cells, even across large distances within an organism. This implies that the presence in an organism of a single cell that harbours in a gene in its genome a mutation that causes a certain effect in the protein encoded by said gene, may result in the export of the mRNA comprising said mutation to many other cells in the organism that—in their own genome—lack said mutation. This may thus lead to a situation in which cells lacking a mutation in their own genetic material import mRNA molecules comprising said mutation, and subsequently translate that mRNA molecule into the protein that is encoded by said mRNA molecule. The effect thereof is that cells lacking said mutation may produce and harbour a protein that comprises said mutation. The mRNA transcripts of one mutated cell could thus affect the behaviour and/or phenotype of a multitude of non-mutated cells in the same organism, if the mRNA molecules sent out by said mutated cell are mobile and are able to move from the cell by which they have been produced to another cell in the same organism where they can be translated into protein. This mechanism may e.g. be relevant in the blood stream of animals, where essentially all cells are in a position to communicate with each other by means of molecules that are present in the blood, and in plants, wherein all organs are connected to each other by means of the vascular tissue.

Alternatively, the one cell may not be mutated, but it may be subjected to a stimulus, which causes it to produce a specific mRNA transcript or a specific splice-form of an mRNA transcript. This specific transcript or splice-form thereof may subsequently be transported to other cells in the organism, which had not (yet) received that stimulus, or which are incapable of responding to the stimulus. In plants, for example, cells of a leaf may respond to a change in light quality, and signal this perception to the roots. Root cells may detect changes in water availability in the soil, and communicate this to e.g. stomatal cells. Mobile mRNA transcripts may constitute a part of such intercellular communication signals between different parts of an organism.

In one embodiment, the invention relates to a method for changing the intercellular mobility of an mRNA of a gene in an organism, comprising modifying a tRNA-like structure present in the mRNA by mutating the gene from which the mRNA is transcribed. Mutating the gene may comprise deleting the sequence of the tRNA-like structure from the gene, mutating the sequence of the tRNA-like structure to change the tridimensional configuration thereof, or inserting a genetic element (such as, for example, a transposon, a retrotransposon, a T-DNA insertion, or a retroviral repeat sequence) into the gene to remove the tRNA-like structure from the transcribed part of the gene, such that the sequence encoding the TLS is no longer transcribed as part of the mRNA to which it initially belonged, thus changing the mobility of that mRNA.

Deleting the sequence of the tRNA-like structure from the gene may, for example, be accomplished by using genome editing tools such as CRISPR-Cas, using two guide RNAs designed to respectively target sequences upstream and downstream of the coding sequence of the tRNA-like structure in the gene, thereby leading to double-stranded breaks in the gene up- and downstream from the coding sequence of the tRNA-like structure in the gene, which may result in the removal of said coding sequence of the tRNA-like structure from the gene. Alternatively, deleting the sequence of the tRNA-like structure from the gene may be accomplished in vitro, using standard molecular biology techniques or gene synthesis techniques, and subsequently introducing a DNA construct encoding a tRNA::mRNA bicistronic transcript, or the in vitro transcribed transcript itself, into the organism.

The tridimensional configuration of a tRNA typically comprises stem-loop structures: from 5' to 3' these are the D arm (or D stem-loop), the A or anticodon arm (or A stem-loop, or anticodon stem-loop), and the T arm (or TψC arm, TψC arm, or TψC stem-loop). Between the A and T arms a variable loop may be present. Mutating the sequence of the tRNA-like structure to change the tridimensional configuration thereof may comprise deleting part of the transcribed sequence thereof, mutating one or more nucleotides involved in the formation of a stem-loop structure in the tRNA-like structure, or inserting one or more nucleotides in a stem-loop of the tRNA-like structure.

Mutations may be induced at random or in a targeted manner, using various mutagenesis methods known in the prior art. In vitro mutagenesis methods include, for example, site-directed mutagenesis, PCR-mediated mutagenesis, and total gene synthesis. In vivo mutagenesis may, for example, be achieved randomly by means of one or more chemical compounds, such as ethyl methanesulphonate, nitrosomethylurea, hydroxylamine, proflavine, N-methyl-N-nitrosoguanidine, N-ethyl-N-nitrosourea, N-methyl-N-nitro-nitrosoguanidine, diethyl sulphate, ethylene imine, sodium azide, formaline, urethane, phenol, ethylene oxide, and/or by physical means, such as UV-irradiation, fast-neutron exposure, X-rays, gamma irradiation, and/or by insertion of genetic elements, such as transposons, T-DNA, retroviral elements. Mutations may also be introduced specifically by means of homologous recombination, oligonucleotide-based mutation induction, or targeted genome editing methods such as TALEN, zinc-finger technology, or CRISPR-Cas.

In one embodiment, deleting part of the transcribed sequence of the tRNA-like structure in a gene comprises deleting the A and/or T stem-loops from the tRNA-like structure. As is shown in Example 2, removal of the A and T stem-loop structures results in the abolition of mobility of an mRNA transcript that is mobile when the A and T stem-loop structures are present. The removal of the D stem-loop, of the D and T stem-loops or of the D and A stem-loops from a gene did not abolish the mobility of the same mRNA transcript.

It should be noted that the term "tRNA-like structure" as used in this application not only comprises intact tRNA structures that are present in the mRNA transcript of a gene (and which can be screened for using the tRNA motif scan approach, explained in Example 2), but also incomplete tRNA structures that lack one or more stem-loop structures but that still retain the ability to enable the intercellular mobility of the mRNA transcript of said gene. The term "tRNA-like structure" as used in the context of the present invention thus also encompasses tRNA structures that lack the D stem-loop, the D and T stem-loops, or the D and A stem-loops. The efficacy of such incomplete structures for conferring mobility to an mRNA transcript has been shown in Example 2 and FIG. 4C.

In one embodiment, the present invention relates to a method for changing the intercellular mobility of an mRNA of a gene in an organism, wherein the change in mobility results in a loss of the function of the gene. This is the case for genes whose mRNA transcript is transcribed in one cell-type, tissue or organ of an organism, but whose gene product (the encoded protein) functions in at least one other cell-type, tissue or organ of the organism, where its mRNA transcript is not produced. For such genes, the intercellular mobility of their mRNA transcript is thus essential for the normal functionality of the gene in the organism. The loss of intercellular mobility of the mRNA transcript of such a gene results in a loss of the function of the gene in the cells, tissues or organs towards which the mRNA transcript moves during normal growth, development and/or functioning of the organism and in which it is normally translated into protein. The loss of intercellular mobility of the mRNA transcript thus leads to the absence or reduced presence of the gene product (i.e. the encoded protein) in the cells, tissues or organs where the mRNA transcript moves towards during normal growth, development and/or functioning of the organism. The phenotype of said cells, tissues or organs may be affected by this absence or reduced presence, and the morphology, responsiveness and/or functionality of said cells, tissues or organs may be affected thereby. This situation is illustrated in Example 3, which shows that the loss of transcript mobility for the CK1 gene in plants results in the absence of CK1 transcript in the phloem, and in a very similar phenotype as could be observed in a knock-out mutant that lacked the CK1 transcript altogether.

In another embodiment, the present invention relates to a method for changing the intercellular mobility of an mRNA of a gene in an organism, comprising including the coding sequence of a tRNA-like structure in the transcribed part of the gene.

In one embodiment, the present invention relates to a method for changing the intercellular mobility of an mRNA of a gene in an organism, wherein the change in mobility results in ectopic presence of the gene product in the organism. In this manner, an mRNA transcript that does not display intercellular mobility can be rendered mobile, by including a tRNA-like structure in said transcript.

In another embodiment, the present invention relates to a method for changing the intercellular mobility of an mRNA of a gene in an organism, wherein the gene is a non-endogenous gene in at least part of the organism. This situation is illustrated in Example 2, wherein the addition of a TLS to the 3'UTR of the ß-glucuronidase-encoding gene (GUS) makes the GUS transcript mobile, and leads to translation of the protein in distant parts of the plant, across a graft junction. This situation is also illustrated in Example 1, wherein a modified version of DMC1 is provided in the form of a DNA construct in a transgenic rootstock. The modification comprise the addition of a TLS in the 3'UTR of the gene, and a truncation of the gene which turns the encoded protein into a dominant-negative version that interferes with the function of wild-type DMC1. Said modified transcript is demonstrated to be transported towards the male spores in a grafted scion, where the encoded protein (which is a dominant-negative version of DMC1) subsequently affects development.

Suitably, including the coding sequence of a tRNA-like structure in the transcribed part of the gene is achieved by introducing the complementary sequence of the tRNA-like structure in a DNA construct comprising the complementary sequence of the mRNA, or by introducing the complementary sequence of the tRNA-like structure in the endogenous gene, by means of e.g. genome editing tools such as CRISPR-Cas.

In one embodiment, the coding sequence of a tRNA-like structure is introduced into the 3' untranslated region (3'UTR) of the mRNA of the gene. Preferably, the coding sequence of a tRNA-like structure is then introduced after the stop-codon of a gene, such that it is present in the transcribed part of the gene but does not affect the open reading frame of the gene. Alternatively, the coding sequence of a tRNA-like structure may also be introduced into the 5' untranslated region (5'UTR) of the mRNA of the gene, or in the open reading frame of the gene, in such a way that the coding sequence is not disrupted or the reading frame is shifted.

The DNA construct may be stably integrated in the genome of the organism, transiently expressed in the organism, or in vitro transcribed. Said DNA construct comprises a suitable promoter that is capable of driving expression of the gene in a suitable environment. There are, for example, promoters that are ubiquitous, organ-, tissue- or cell-type specific, and promoters that are constitutive or regulated by environmental (physical or biological) or endogenous (developmental) queues, or regulated by chemicals.

Suitable constitutive promoter control sequences for mammals include, but are not limited to, cytomegalovirus immediate early promoter (CMV), simian virus (SV40) promoter, adenovirus major late promoter, Rous sarcoma virus (RSV) promoter, mouse mammary tumor virus (MMTV) promoter, phosphoglycerate kinase (PGK) promoter, elongation factor (ED1)-alpha promoter, ubiquitin promoters, actin promoters, tubulin promoters, immunoglobulin promoters, fragments thereof, or combinations of any of the foregoing.

Suitable constitutive promoter control sequences for plants include, but are not limited to, 35S cauliflower mosaic virus (CaMV) promoter, opine promoters, ubiquitin promoters, actin promoters, tubulin promoters, alcohol dehydrogenase promoters, fragments thereof, or combinations of any of the foregoing.

Examples of suitable regulated promoter control sequences for animals or plants include, without limit, those regulated by heat shock, cold, drought, heavy metals, steroids (such as dexamethasone, ß-estradiol), antibiotics, or alcohols (such as ethanol).

Non-limiting examples of tissue-specific mammalian promoters include B29 promoter, CD14 promoter, CD43 promoter, CD45 promoter, CD68 promoter, desmin promoter, elastase-1 promoter, endoglin promoter, fibronectin promoter, Flt-1 promoter, GFAP promoter, GPllb promoter, ICAM-2 promoter, INF-13 promoter, Mb promoter, Nphsl promoter, OG-2 promoter, SP-B promoter, SYN1 promoter, and WASP promoter.

Non-limiting examples of tissue-specific plant promoters include the ß-phaseolin, glutenin, a-Kaf, zein, ß-conglycinin and AGPase promoters (for seed-specific expression), the LAT52, GEX2, MAN5 and FRK4 promoters (for pollen-specific expression), the rolD, REO, Prx and Tip2 promoters (for root-specific expression), and the Zmglp1, PnGLP and PDX1 promoters (for leaf-specific expression).

The promoter sequence can be wild type or it can be modified for more efficient or efficacious expression. In one exemplary embodiment, the encoding DNA can be operably linked to a CMV promoter for constitutive expression in mammalian cells.

In certain embodiments, the sequence of an endogenous or non-endogenous gene can be operably linked to a promoter sequence that is recognised by a phage RNA polymerase for in vitro mRNA synthesis. In such embodiments, the in vitro-transcribed RNA can be purified for administration to an organism. For example, the promoter sequence can be a T7, T3, or SP6 promoter sequence or a variation of a T7. T3, or SP6 promoter sequence. In an exemplary embodiment, the DNA encoding the fusion protein is operably linked to a T7 promoter for in vitro mRNA synthesis using T7 RNA polymerase.

In alternative embodiments, the sequence of an endogenous or non-endogenous gene can be operably linked to a promoter sequence for in vitro expression in bacterial or eukaryotic cells.

The DNA construct or the in vitro synthesised RNA transcript may be introduced into the organism by various methods known in the prior art.

When a DNA construct is intended for stable integration in the genome of an organism or for transient expression in an organism, it can be introduced into said organism or into a cell derived therefrom by means of (micro)injection, ingestion, transfection, electroporation, DEAE-dextran treatment, lipofection, nanoparticle-mediated transfection, protein transduction domain mediated transduction, virus-mediated gene delivery, PEG-mediated transfection of protoplasts, infection with a suitable virus or bacterium (such as *Agrobacterium* for plants), etcetera.

When a DNA construct is intended for in vitro transcription of the encoded mRNA, in vitro transcription may be achieved using any in vitro transcription system known in the art. Alternatively, transcription may also be done in a heterologous organism, after which the transcript of interest is subsequently purified for further use.

An in vitro synthesised RNA transcript may be introduced into the organism or into a cell derived therefrom by the methods listed above (such as injection into the blood stream of a mammal or into the phloem of a plant), and also by means of, for example, exogenous application on the surface of the organism. Exogenous application may for example be performed according to the disclosure in patent application WO2015/200539. Exogenous application to cell cultures or tissue cultures may, for example, be performed using electroporation, transfection, etcetera.

When an in vitro synthesised RNA transcript is introduced into an organism, a suitable promoter is not required, because transcription does not need to take place inside the organism's cells. Said transcript may immediately be translated, and/or it may move into cells of the organism and from one cell of the organism to other cells of the organism. According to the invention the movement of the transcript is due to the presence of TLS.

Another application is the use of cultured cells that produce an mRNA transcript harbouring a TLS for in vivo application in an organism. For example, cultured cells harbouring a gene that—when transcribed—gives rise to an mRNA transcript harbouring a TLS, may be injected (or otherwise administered) into a mammal's blood stream, where said cells secrete an mRNA transcript harbouring a TLS into the extracellular matrix. This mRNA transcript can subsequently be taken up by other cells in the organism, due to the presence of a TLS. This constitutes an efficient way of delivering mRNA transcripts in vivo. Said mRNA transcript may encode any protein that can be administered to the organism. In a further embodiment, said mRNA transcript encodes a therapeutic protein, an endogenously occurring protein or a modified version thereof, or a non-endogenously occurring protein. Suitably, the administration of said cells to the organism is for the treatment of a disease, or for gene therapy.

In one embodiment, the complementary sequence of a tRNA-like structure is introduced into the transcribed part of a gene in a DNA construct, and the gene comprising the tRNA-like structure is transcribed in vitro. The mRNA transcript comprising the tRNA-like structure is subsequently introduced into an organism, cell culture or tissue culture, such that it can move into cells, and from one cell into other cells. This embodiment represents an application of the present invention that does not require the use of DNA constructs in vivo. The manner in which the mRNA transcript comprising the tRNA-like structure is introduced into an organism, cell culture or tissue culture, depends on the type of organism, cell culture or tissue culture that is being used. Means by which introduction can be achieved comprise, for example, injection into the blood stream of animals, injection into the vascular tissue or apoplast of plants, or exogenous application on the surface of the organism. The use of cell-penetrating peptides may for example facilitate the entry of the mRNA transcript into the organism.

As stated above, the term "tRNA-like structure" as used in this application not only comprises intact tRNA structures that are present in the mRNA transcript of a gene (and which can be screened for using the tRNA motif scan approach, explained in Example 2), but also incomplete tRNA structures that lack one or more stem-loop structures but that still retain the ability to enable the intercellular mobility of the mRNA transcript of said gene. The term "tRNA-like structure" as used in the context of the present invention thus also encompasses tRNA structures that lack the D stem-loop, the D and T stem-loops, or the D and A stem-loops. The term "tRNA-like structure" as used in this application thus encompasses intact tRNA structures and tRNA structures that comprise at least the A stem-loop and/or the T stem-loop.

Figure 4A:
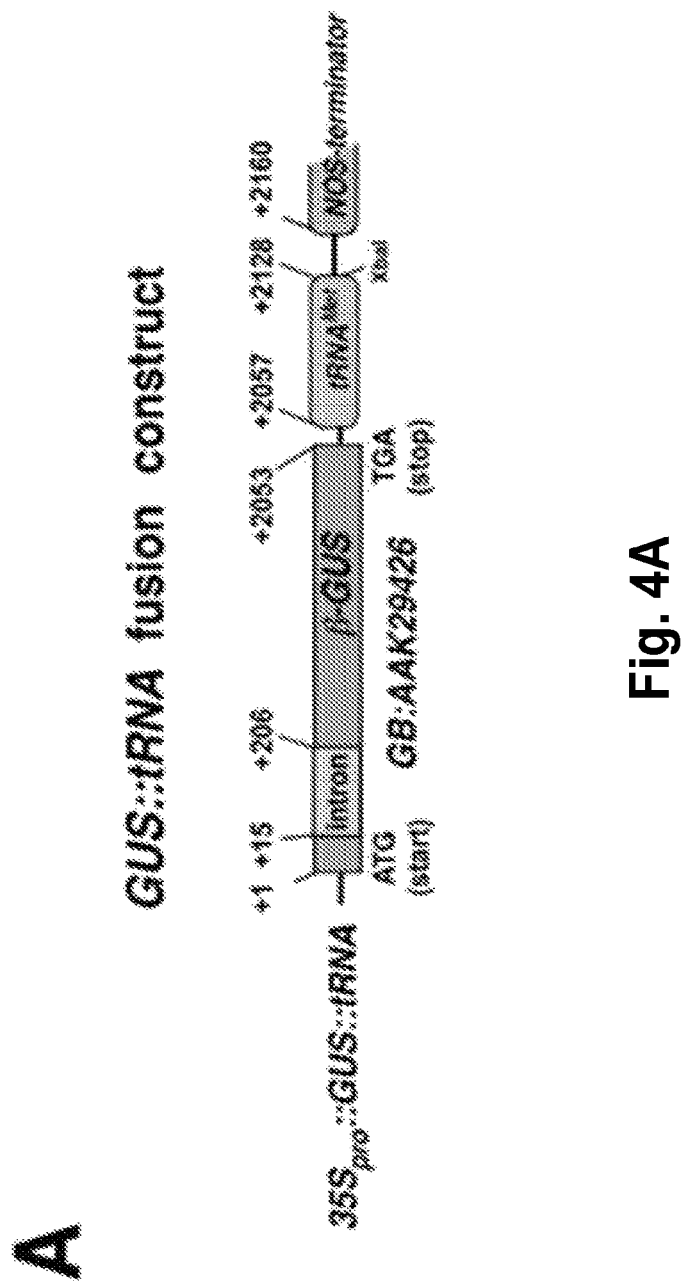
Figure 4B:
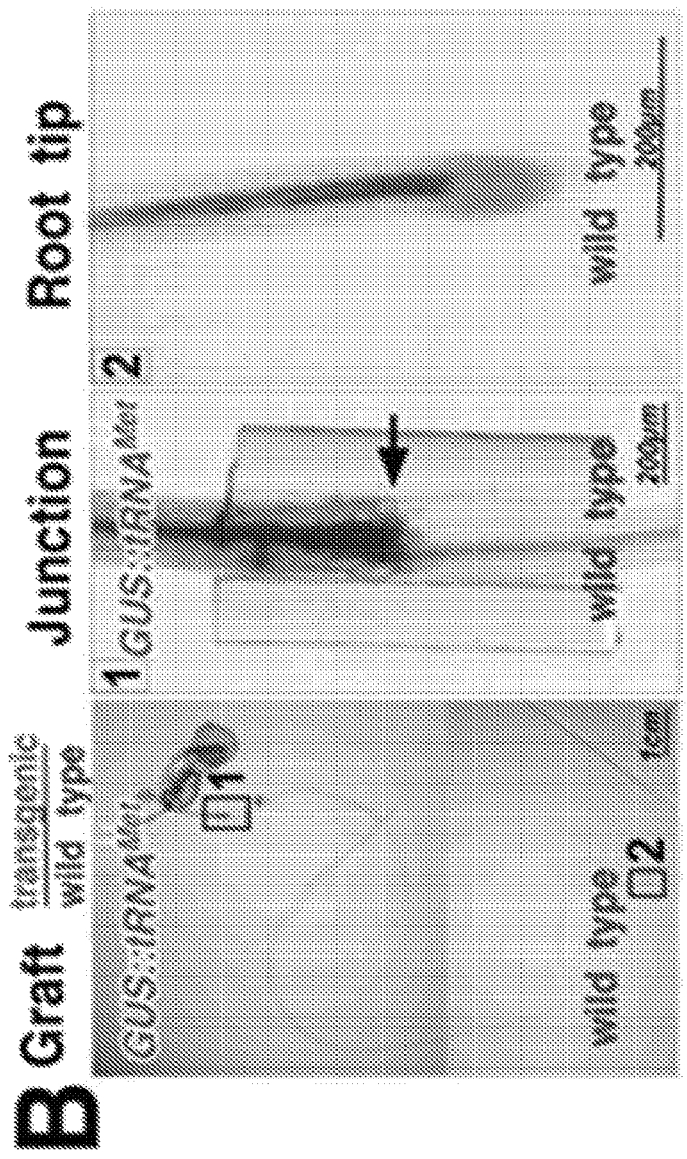
Figure 4C:
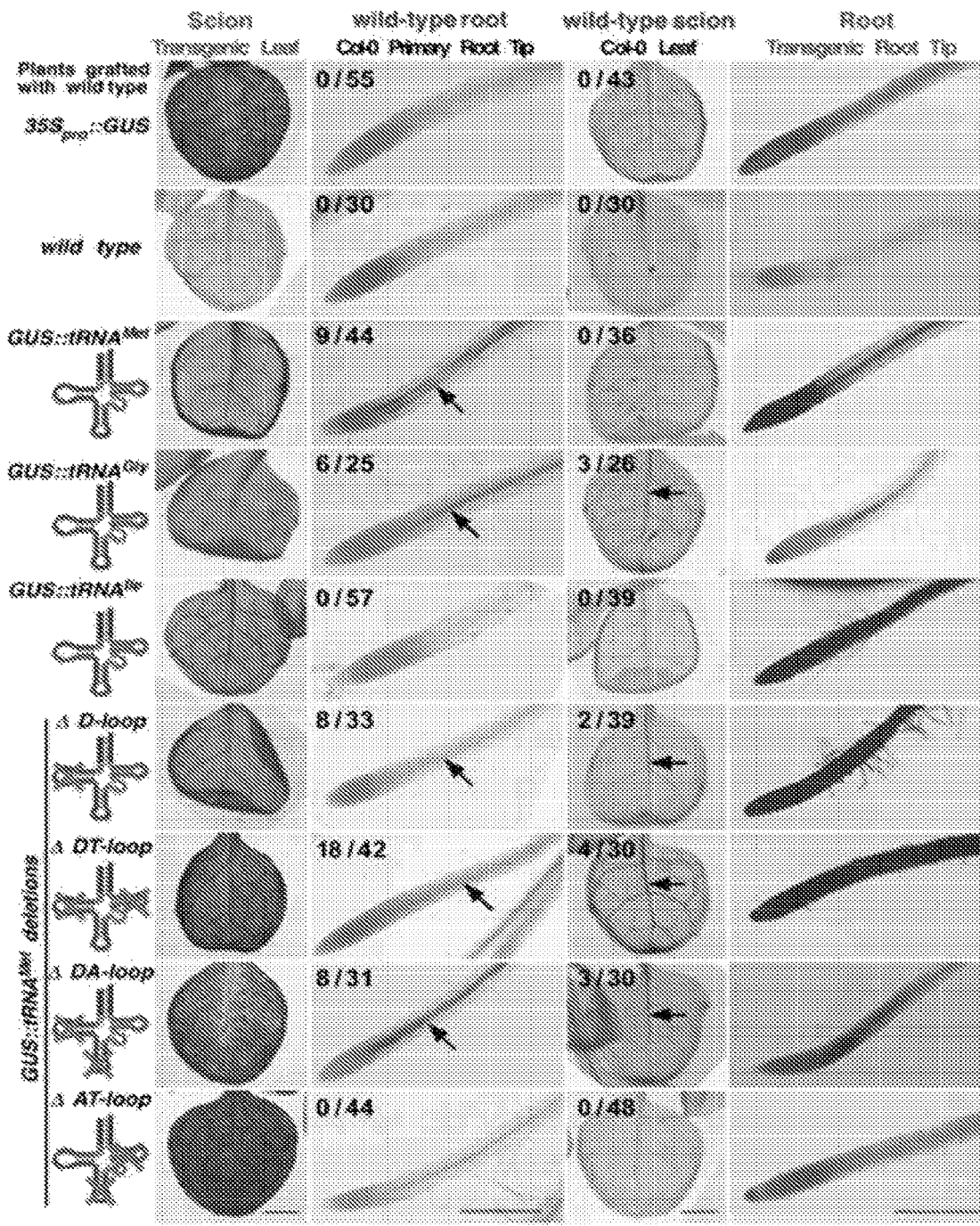

The efficacy of such incomplete structures for conferring mobility to an mRNA transcript has been shown in Example 2 and FIG. 4C. In one embodiment, the tRNA-like structure is selected from the group consisting of $tRNA^{Ala}$, $tRNA^{Arg}$, $tRNA^{Asn}$, $tRNA^{Asp}$, $tRNA^{Cys}$, $tRNA^{Gln}$, $tRNA^{Glu}$, $tRNA^{Gly}$, $tRNA^{His}$, $tRNA^{Ile}$, $tRNA^{Leu}$, $tRNA^{Lys}$, $tRNA^{Met}$, $tRNA^{Phe}$, $tRNA^{Pro}$, $tRNA^{Ser}$, $tRNA^{Thr}$, $tRNA^{Trp}$, $tRNA^{Tyr}$, $tRNA^{Val}$. In another embodiment, the tRNA-like structure is selected from the group consisting of tRNAAla, tRNAArg, tRNAAsn, tRNAAsp, tRNACys, tRNAGln, tRNAGlu, tRNAGly, tRNAHis, tRNAIle, tRNALeu, tRNALys, tRNAMet, tRNAPhe, tRNAPro, tRNASer, tRNAThr, tRNATrp, tRNATyr, tRNAVal and it lacks the D stem-loop, the D and T stem-loops, or the D and A stem-loops.

In a further embodiment, the tRNA-like structure comprises a tRNA anticodon with a sequence from 5' to 3' in the transcribed mRNA selected from the group consisting of AGC, CGC, UGC, ACG, CCG, CCU, UCG, UCU, GUU, GUC, GCA, CUG, UUG, CUC, UUC, ACC, CCC, GCC, UCC, GUG, AAU, AAG, CAA, CAG, GAG, UAA, UAG, CUU, UUU, CAU, GAA, AGG, CGG, UGG, AGA, CGA, GCU, GGA, UGA, AGU, CGU, UGU, CCA, GUA, AAC, CAC, UAC. In another embodiment, the tRNA-like structure comprises a tRNA anticodon with a sequence from 5' to 3' in the transcribed mRNA selected from the group consisting of AGC, CGC, UGC, ACG, CCG, CCU, UCG, UCU, GUU, GUC, GCA, CUG, UUG, CUC, UUC, ACC, CCC, GCC, UCC, GUG, AAU, AAG, CAA, CAG, GAG, UAA, UAG, CUU, UUU, CAU, GAA, AGG, CGG, UGG, AGA, CGA, GCU, GGA, UGA, AGU, CGU, UGU, CCA, GUA, AAC, CAC, UAC and it lacks the D stem-loop, or the D and T stem-loops.

As shown in Example 2, some tRNA-like structures exist that have a tridimensional structure that does not promote intercellular mobility of an mRNA transcript, such as $tRNA^{Ile}$ with anticodon UAU.

In one embodiment, the present invention relates to a method for changing the intercellular mobility of an mRNA of a gene in a plant, wherein said plant consists of a rootstock of a first plant upon which a scion of a second plant has been grafted, and wherein the intercellular mobility of an mRNA of a gene in the first and/or the second plant has been changed. This embodiment has been illustrated in Examples 1-3, with Arabidopsis and Nicotiana (tobacco).

This embodiment can be carried out with any plant species for which grafting is possible. Commercially relevant plants that can be grafted are, for example, plants belonging to the genera Apium, Beta, Brassica, Capsicum, Cichorium, Citrullus, Cucumis, Cucurbita, Benincasa, Daucus, Eruca, Lactuca, Lagenaria, Luffa, Phaseolus, Pisum, Lens, Raphanus, Solanum, Spinacia, Valerianella, Nicotiana, Petunia, Arabidopsis, Capsella, Arabis, Cardamine, Malus, Pyrus, Prunus, Vitis, Rosa, Fragaria, Populus, Fagus, Pinus, Picea, Ginkgo, Larix, Betula, Quercus, Salix, Alnus, Corylus, Amygdalus, Vaccinium, Rubus, Persea, Citrus, Castanea, Acer, Fraxinus, Coffea, Camellia, Theobroma, Olea, Cicer, Juglans, Pistacia, Arachis, Anacardium, Macadamia, Ficus, Litchi, Actinidia, Bougainvillea, Helianthus, Hibiscus, Malva, Gossypium, Cannabis, Stevia, Opuntia, and Ipomoea. This is of course a non-exhaustive list.

In general, many dicotyledonous plants can be grafted, whereas monocotyledonous plants cannot be grafted. However, a method has recently been developed to graft recalcitrant species such as soybean (Glycine max) and commercially important species of the Poaceae family, such as maize (Zea mays), rice (Oryza sativa), wheat (Triticum aestivum), etcetera (T. Harada, European patent application EP2918161). For those species this embodiment of the method of the present invention can thus also be applied.

This embodiment has various distinct applications. Firstly, the intercellular mobility of an mRNA of an endogenous gene may be changed. This may be done by changing the encoding gene in the rootstock or in the scion of a grafted plant, and it may either lead to a loss of mobility for an mRNA transcript that is naturally mobile in the plant, or to a gain of mobility for an mRNA transcript that is naturally non-mobile in the plant. In case of a gain of mobility, the mRNA transcript may move across the graft junction. In case of a loss of mobility, the rootstock or scion may be depleted of the mRNA transcript, which may lead to phenotypic effects. Changing the encoding gene can be done in all manners that have been described above, such as mutagenesis, genome editing and/or the use of transgenes.

In a further embodiment, the phenotype of the rootstock and/or scion is changed. This may for example be achieved by the movement of a mobile mRNA transcript across the graft junction, where it complements for the absence of that mRNA transcript in either the rootstock or the scion due to a mutation. This thus represents a method for mutant complementation, by grafting a mutant plant onto a wild-type plant and rescuing the mutant phenotype by means of a mobile mRNA transcript that compensates for the absence of the corresponding endogenous mRNA transcript.

In addition to changing the intercellular mobility of an mRNA of an endogenous gene, it is of course possible to induce additional mutations in said mRNA transcript, such as point mutations, or to induce other modifications in said mRNA transcripts, such as insertions or deletions. Such additional mutations or modifications may, for example, have an effect on the primary sequence of the encoded protein, and on the encoded protein's structure and/or function. An example of this embodiment is presented in Example 1, wherein a modified (dominant-negative) form of DMC1 is used to interfere with DMC1 function in male spores.

Secondly, in another embodiment, a non-endogenous gene may be rendered mobile in an organism. The use of non-endogenous genes, such as reporter genes, is common practice in molecular biology, but the expression pattern of such non-endogenous genes depends entirely on the use of a suitable promoter, that is able to drive a gene's expression in the organism. Suitable promoters have been discussed above in this text. This situation is illustrated in Example 2, with ß-glucuronidase (GUS).

Another example of a non-endogenous gene for which it is interesting to render its mRNA transcript mobile in an organism is Cas9. Cas9 is an RNA-guided endonuclease that has the capacity to create double-stranded breaks in DNA in vitro and in vivo, also in eukaryotic cells. It is part of an RNA-mediated adaptive defence system known as Clustered Regularly Interspaced Short Palindromic Repeats (CRISPR) in bacteria and archaea. Cas9 gets sequence-specificity when it associates with a guide RNA molecule, which can target sequences present in an organism's DNA based on their sequence. Cas9 requires the presence of a Protospacer Adjacent Motif (PAM) immediately following the DNA sequence that is targeted by the guide RNA. The Cas9 enzyme has been first isolated from *Streptococcus pyogenes* (SpCas9), but functional homologues from many other bacterial species have been reported, such as *Neisseria meningitides, Treponema denticola, Streptococcus thermophilus, Francisella novicida, Staphylococcus aureus*, etcetera. For SpCas9, the PAM sequence is 5'-NGG-3', whereas various Cas9 proteins from other bacteria have been shown to recognise different PAM sequences. In nature, the guide RNA is a duplex between crRNA and tracrRNA, but a single guide RNA (sgRNA) molecule comprising both crRNA and tracrRNA has been shown to work equally well (Jinek et al, 2012, *Science* 337: 816-821). The advantage of using an sgRNA is that it reduces the complexity of the CRISPR-Cas9 system down to two components, instead of three. For use in an experimental setup (in vitro or in vivo) this is an important simplification.

An alternative for Cas9 is, for example, Cpf1, which does not need a tracrRNA to function, which recognises a different PAM sequence, and which creates sticky end cuts in the DNA, whereas Cas9 creates blunt ends.

On the one hand, genetic modification techniques can be applied to express an RNA-guided endonuclease and/or guide RNAs in eukaryotic cells. One or more DNA constructs encoding an RNA-guided endonuclease and at least one guide RNA can be introduced into a cell or organism by means of stable transformation (wherein the DNA construct is integrated into the genome) or by means of transient expression (wherein the DNA construct is not integrated into the genome, but it expresses an RNA-guided endonuclease and at least one guide RNA in a transient manner). This approach requires the use of a transformation vector and a suitable promoter for expression in said cell or organism. Organisms into which foreign DNA has been introduced are considered to be Genetically Modified Organisms (GMOs), and the same applies to cells derived therefrom and to offspring of these organisms. In important parts of the worldwide food market, transgenic food is not allowed for human consumption, and not appreciated by the public. There is therefore a need for an alternative, "DNA-free" delivery method of CRISPR-Cas components into intact plants, that does not involve the introduction of DNA constructs into the cell or organism.

In the prior art, introducing the mRNA encoding Cas9 into a cell or organism has been described, after in vitro transcription from a DNA construct encoding an RNA-guided endonuclease, together with at least one guide RNA. This approach does not require the use of a transformation vector and a suitable promoter for expression in said cell or organism.

Another known approach is the in vitro assembly of ribonucleoprotein (RNP) complexes, comprising an RNA-guided endonuclease protein (for example Cas9) and at least one guide RNA, and subsequently introducing the RNP complex into a cell or organism. The GMO status of this approach is not yet clear, but the introduction of RNP complexes into intact organisms is technically challenging. In animals and animal cell and tissue cultures, RNP complexes have been introduced by means of, for example, injection, electroporation, nanoparticles, vesicles, and with the help of cell-penetrating peptides. However, the RNP complexes can only perform their function in cells where they have been introduced into, and this limits the efficiency of this approach. There is a need for a self-propagating system wherein the CRISPR-Cas components move between cells.

In plants, the use of RNPs has been demonstrated in protoplasts, for example with polyethylene glycol (PEG) transfection (Woo et al., 2015, *Nat. Biotech.* 33: 1162-1164). However, the applicability of this technique depends entirely on the availability of protocols for the regeneration of entire plants from protoplasts. Such protocols are not available for all plants, and there is therefore a need for an alternative delivery method of CRISPR-Cas components in plant cells and in intact plants.

A specific application of the present invention involves the mobilisation of an RNA-guided endonuclease-encoding mRNA in a plant. A shown in Example 1 with DMC1-encoding mRNA, mRNA transcripts that are present in the phloem of a plant are able to reach the plant's male spores. When a similar approach is taken with an RNA-guided endonuclease-encoding mRNA, it is therefore not only possible to modify the genome of a plant's somatic cells, but also the genome of its male germline, in the presence of at least one suitable guide RNA. The latter category of genome modifications is heritable, as they can be transmitted to the next generation.

Suitably, in one embodiment, the RNA-guided endonuclease gene can be encoded by a DNA construct that is integrated into the genome of one plant, onto which another plant is subsequently grafted. In this manner, the cells of the rootstock harbour a transgenic construct, but the cells of the scion do not. However, when the mRNA transcript encoding the RNA-guided endonuclease comprises a TLS, it is rendered mobile and it is able to cross the graft junction, and the RNA-guided endonuclease-encoding transcript can be delivered into cells of the scion, where the RNA-guided endonuclease protein can be translated. In this situation, cells of the scion produce a protein that is not encoded in their own genome, and this protein is capable of modifying a chromosomal sequence in said cells, when at least one suitable guide RNA is present in said cells.

Alternatively, the mRNA transcript encoding the RNA-guided endonuclease and comprising a TLS may be introduced into a plant by direct injection, for example into the vascular tissue, or by exogenous application, as has been described above. Said transcript will then behave as if it had been produced inside the plant, and it will be delivered into cells of the plant, where the encoded protein will be translated and where it will perform its function. In this embodiment, grafting is not a requirement.

After said modification of a chromosomal sequence has taken place, the cells can be used to produce plants that harbour said modification in their genome, using any plant regeneration method known in the art (such as in vitro tissue culture).

In a preferred embodiment, the RNA-guided endonuclease-encoding mRNA transcript is translated into the encoded protein inside male spores of a plant, where the encoded protein may modify a chromosomal sequence in the presence of at least one suitable guide RNA. The at least one guide RNA may, for example, be introduced into the cells by means of injection into the anther, the phloem or other parts of the plant, *Agrobacterium*-mediated transformation, or exogenous application, or it may be encoded by a DNA-construct that is present in the cells of the plant that produces said male spores. Said spores may be produced by the scion of a grafted plant. It has been shown that many small RNA molecules (of comparable size as a typical guide RNA) are mobile in the phloem and are able to move systemically throughout the plant and across graft junctions. It has also been shown that such small RNA molecules are able to reach the male spores of a scion when they are transcribed in a rootstock (see for example patent application WO2013017683).

In a particular embodiment the invention thus provides a method for modifying a chromosomal sequence in a plant cell or spore, comprising:
  a) combining a first plant comprising a rootstock, which harbours a nucleic acid sequence encoding a modified, non-naturally occurring RNA-guided endonuclease protein, with a scion from a second plant grafted onto the rootstock of the said first plant, whereby the said nucleic acid sequence generates a transcript in the rootstock of the first plant, which transcript is transported systemically across the graft junction to enter the scion of the second plant, and which transcript is imported into cells of the scion of the second plant, where it is translated into a functional protein;
  b) providing at least one guide RNA or DNA encoding at least one guide RNA to at least one cell or spore of the scion of the second plant, wherein the at least one guide RNA is a single molecule comprising a 5' region that is complementary to a target site in a chromosomal sequence of said second plant;
  c) allowing each guide RNA to direct an RNA-guided endonuclease protein to a targeted site in the chromosomal sequence, where the RNA-guided endonuclease protein introduces a double-stranded break in the targeted site, and allowing the cell to repair the double-stranded break by a DNA-repair process such that the chromosomal sequence is modified in at least one cell or spore of the scion of the second plant.

The nucleic acid sequence encoding a modified, non-naturally occurring RNA-guided endonuclease protein may be a transgene that is stably integrated or transiently expressed.

In a particular embodiment, the RNA-guided endonuclease protein is derived from a Cas protein. The Cas protein is suitably Cas9, or a variant thereof. The Cas protein is for example derived from the genus *Streptococcus*.

In a particular embodiment, the nucleic acid sequence encoding a modified, non-naturally occurring RNA-guided endonuclease protein comprises a tRNA-like structure that allows the transcript to be transported systemically across the graft junction from the rootstock of the first plant into the scion of the second plant. The nucleic acid sequence encoding a modified, non-naturally occurring RNA-guided endonuclease protein may further comprise at least one localisation signal to a DNA-containing organelle and optionally a marker domain. Non-limiting examples of marker domains are fluorescent markers (such as Green Fluorescent Protein, Yellow Fluorescent Protein, mCherry), epitope tags (such as FLAG, His, HA, calmodulin), etcetera.

The localisation signal is suitably selected from the group comprising a nuclear localisation signal, a chloroplast targeting signal, a mitochondrial targeting signal.

The nucleic acid sequence encoding a modified, non-naturally occurring RNA-guided endonuclease protein may optionally further comprises a FokI endonuclease domain or another protein domain.

The tRNA-like structure can be $tRNA^{Ala}$, $tRNA^{Arg}$, $tRNA^{Asn}$, $tRNA^{Asp}$, $tRNA^{Cys}$, $tRNA^{Gln}$, $tRNA^{Glu}$, $tRNA^{Gly}$, $tRNA^{His}$, $tRNA^{Ile}$, $tRNA^{Leu}$, $tRNA^{Lys}$, $tRNA^{Met}$, $tRNA^{Phe}$, $tRNA^{Pro}$, $tRNA^{Ser}$, $tRNA^{Thr}$, $tRNA^{Trp}$, $tRNA^{TYR}$, $tRNA^{Val}$. The term "tRNA-like structure" as used in the context of the present invention also encompasses tRNA structures that lack the D stem-loop, the D and T stem-loops, or the D and A stem-loops.

The tRNA-like structure is located in the 3'UTR of the transcript, in the 5'UTR of the transcript, or in the coding sequence of the transcript.

In one embodiment, the guide RNA is a single-chain guide RNA, wherein the guide RNA is a DNA-targeting RNA comprising a) a first segment comprising a nucleotide sequence that is complementary to a chromosomal sequence in a plant cell or spore, and b) a second segment that interacts with an RNA-guided endonuclease protein. Suitably, the guide RNA is a single-chain guide RNA comprising a crRNA and a tracrRNA.

Expression of a transgenic nucleic acid sequence in the first plant is suitably achieved by operably linking the said nucleic acid sequence to a promoter sequence that confers a ubiquitous expression profile or a tissue- or cell-type specific expression profile onto the transgenic nucleic acid sequence, and/or to an inducible promoter. Suitable promoters have been discussed above.

In one embodiment, the promoter sequence confers onto the transgenic nucleic acid sequence an expression profile that encompasses roots.

When expression of the transgenic nucleic acid sequence in the first plant is transient, transient expression is suitably achieved by use of an inducible promoter, selected from the group comprising heat-inducible promoters, cold-inducible promoters, chemical-inducible promoters, steroid-inducible promoters and alcohol-inducible promoters. Suitable promoters have been discussed above.

Providing the at least one guide RNA or DNA encoding the at least one guide RNA to at least one cell or spore of the scion of the second plant is suitably accomplished by means of injection, *Agrobacterium*-mediated transformation, exogenous application, or stable integration or transient expression of a DNA-construct.

The invention further relates to such a method, wherein exogenous application of the at least one guide RNA or DNA encoding the at least one guide RNA comprises applying onto the scion of the second plant or a part thereof a mixture comprising:
  a) a cationic polyelectrolyte;
  b) an osmolyte; and
  c) the at least one guide RNA or DNA encoding the at least one guide RNA,
wherein the at least one guide RNA is a single molecule comprising a 5' region that is complementary to a target site in a chromosomal sequence of said second plant. Exogenous application may be performed according to the disclosure in patent application WO2015/200539.

In one embodiment of this latter method a chromosomal sequence of at least one cell or spore of the second plant is genetically modified without the insertion of external genetic material.

In a particular embodiment of this latter method, the first plant and the second plant belong to the same plant family. Suitably, the first plant and the second plant belong to the same genus, in particular to the same plant species.

In a further embodiment, the plant belongs to one of the following genera: Beta, Brassica, Capsicum, Cichorium, Citrullus, Cucumis, Cucurbita, Benincasa, Daucus, Eruca, Lactuca, Lagenaria, Luffa, Phaseolus, Pisum, Raphanus, Solanum, Spinacia, Valerianella, Nicotiana, Petunia, Arabidopsis, Capsella, Arabis, Malus, Pyrus, Prunus, Vitis, Rosa, Fragaria, Populus, Fagus, Pinus, Picea, Ginkgo, Larix, Betula, Quercus, Salix, Alnus, Corylus, Amygdalus, Vaccinium, Rubus, Persea, Citrus, Castanea, Acer, Fraxinus, Coffea, Camellia, Theobroma, Olea, Cicer, Juglans, Pistacia, Arachis, Anacardium, Macadamia, Ficus, Litchi, Actinidia, Bougainvillea, Helianthus, Hibiscus, Malva, Glycine, Gossypium, Cannabis, Stevia, Opuntia, or Ipomoea.

In an embodiment of this invention where grafting is not performed (for example when the guide RNA and the RNA-guided endonuclease-encoding transcript are both administered to the plant by means of a DNA-free delivery method, such as, for example, injection of the guide RNA and the RNA-guided endonuclease-encoding mRNA transcript into the phloem of the plant), the plant may belong to one of the following genera: Album, Apium, Beta, Brassica, Capsicum, Cichorium, Citrullus, Cucumis, Cucurbita, Benincasa, Daucus, Eruca, Lactuca, Lagenaria, Luffa, Phaseolus, Pisum, Lens, Raphanus, Solanum, Spinacia, Valerianella, Nicotiana, Petunia, Arabidopsis, Capsella, Arabis, Cardamine, Malus, Pyrus, Prunus, Vitis, Rosa, Fragaria, Populus, Fagus, Pinus, Picea, Ginkgo, Larix, Betula, Quercus, Salix, Alnus, Corylus, Amygdalus, Vaccinium, Rubus, Persea, Citrus, Castanea, Acer, Fraxinus, Coffea, Camellia, Theobroma, Olea, Cicer, Juglans, Pistacia, Arachis, Anacardium, Macadamia, Ficus, Litchi, Actinidia, Bougainvillea, Helianthus, Hibiscus, Malva, Glycine, Gossypium, Cannabis, Stevia, Opuntia, Ipomoea, Manihot, Humulus, Acacia, Medicago, Trifolium, Lotus, Vicia, Linum, Fagopyrum, Zea, Triticum, Avena, Hordeum, Oryza, Zizania, Secale, Triticosecale, Sorghum, Bambusa, Dendrocalamus, Saccharum, Cymbopogon, Pennisetum, Panicum, Festuca, Lolium, Phleum, Poa, Miscanthus, Asparagus, Agave, Yucca, Cocos, Elaeis, Phoenix, Amaryllis, Narcissus, Aloe, Canna, Iris, Colchicum, Crocus, Gladiolus, Juncus, Lilium, Tulipa, Musa, Dendrobium, Phalaenopsis, Vanilla, Typha, Zingiber, Curcuma, Lemna.

The present invention will be further illustrated in the Examples that follow and that are not intended to limit the invention in any way. In the Examples reference is made to the following figures.

FIGS. 1A-1G. Dominant-negative DMC1 as a reporter construct causes male sterility in flowers.

(FIG. 1A) Schematic drawing of the $_{DN}$DMC1 RNA fusion constructs used. A. thaliana $_{DN}$DMC1 codes for a truncated protein lacking the N-terminal 92 amino acids and dominantly interferes with meiosis, resulting in misshaped pollen and partial male sterility. The $_{DN}$DMC1 coding sequence was fused to graft-mobile StBEL5 sequences or phloem tRNA$^{Met}$ at the 3'UTR to evaluate their potential to trigger $_{DN}$DMC mRNA transport over graft junctions.

(FIG. 1B) to (FIG. 1E) Fertile anthers of wild-type Nicotiana tabacum plants show regular pollen production with minimal abnormally shaped pollen (2-3%), whereas hpDMC1 siRNA transgenic tobacco plants produce high numbers of abnormally shaped pollen and are sterile as previously described (Zhang et al., 2014). YFP-$_{DN}$DMC1 transgenic plants have normal pollen production similar to wild type. Transgenic plants expressing $_{DN}$DMC1 fused with tRNA$^{Met}$ or StBEL5 at the 3'UTR exhibit increased male sterility.

(FIG. 1C) and (FIG. 1E) Propidium iodide-stained pollen grains harvested from transgenic plants were imaged by Confocal Laser Scanning Microscopy (CLSM) and evaluated by an automatic imaging analysis algorithm to count abnormally shaped pollen (Zhang et al., 2014), indicated by % numbers. Arrows indicate normal pollen; arrowheads indicate abnormally shaped pollen. Scale bars: 30 µm.

(FIG. 1F) and (FIG. 1G) Scheme of performed stem-grafts to evaluate transport of mRNA to wild-type flowers.

FIGS. 2A-2G. $_{DN}$DMC1 fusion transcript transport induces aberrant pollen formation.

(FIG. 2A) Flowers of grafted wild-type stock plants supported by 35S$_{pro}$:YFP-$_{DN}$DMC1 transgenic scions and reciprocal grafts are fertile.

(FIG. 2B) Upper panel: Grafted wild-type/wild-type or wild-type/$_{DN}$DMC1::tRNA$^{Met}$ plants showed normal pollen production when mock-treated. Lower panel: Estradiol-induced expression of $_{DN}$DMC1:tRNA$^{Met}$ in scion or stock plant parts resulted in partially sterile anthers in both transgenic and wild-type flowers. The latter suggests $_{DN}$DMC1::tRNA$^{Met}$ mRNA transport into, and expression of the truncated DMC1 protein in, wild-type male meiocytes.

(FIG. 2C) Flowers of grafted $_{DN}$DMC1::StBEL5 transgenic plants. Upper panel: Mock-treated wild-type/estradiol>>$_{DN}$DMC1::StBEL5 grafts showed weak male sterility. Lower panel: Flowers of grafted plants treated with estradiol exhibit partial male sterility.

(FIG. 2D) RT-PCR assays on RNAs samples from grafted wild-type tissues revealed that the YFP-$_{DN}$DMC1 control transcript is not allocated over graft junctions into wild-type stock leaves (n=6) or scion flowers (n=8). ACTIN2 (ACT2) specific RT-PCR was used as a positive control.

(FIG. 2E) RT-PCR assays on RNA samples from grafted plants. $_{DN}$DMC1::tRNA$^{Met}$ and $_{DN}$DMC1::StBEL5 is detected in transgenic and in wild-type scion flowers. Appearance of a specific PCR product in samples from grafted wild-type stock leaves and wild-type flowers (red asterisks) suggests mobility of the $_{DN}$DMC1::tRNA$^{Met}$ fusion transcript. Number of tested grafted plants is shown on the right.

(FIG. 2F) CLSM images of sepals formed on YFP-$_{DN}$DMC1 producing scions. Upper panel: YFP-$_{DN}$DMC1/YFP-$_{DN}$DMC1 control graft with expected high green fluorescence emitted by YFP-$_{DN}$DMC1. Middle panel: Control graft with siRNA-producing stock plants (hpDMC1) with expected low YFP fluorescence and distribution in YFP-$_{DN}$DMC1 flowers (Zhang et al., 2014). Lower panel: YFP-$_{DN}$DMC1 scion grafted onto $_{DN}$DMC1::tRNA$^{Met}$ transgenic stock shows similar YFP fluorescence levels as YFP-$_{DN}$DMC1/YFP-$_{DN}$DMC1 control grafts. Note that YFP-$_{DN}$DMC1 fusion protein is detected in all epidermal leaf cells except when grafted with hpDMC1 producing DMC1 siRNA lines. Green indicates presence of YFP-$_{DN}$DMC1; Blue: plastid auto-fluorescence. Scale Bar: 300 µm.

(FIG. 2G) Statistical analysis of misshaped pollen appearing on grafted plants. Misshaped pollen formation was significantly higher on wild-type scions supported by $_{DN}$DMC1::tRNA$^{Met}$ and $_{DN}$DMC1::StBEL5 stock plants than in control grafts. Asterisks indicate highly significant differences against controls using Chi-square test for independence of variables in a contingency table. Biological replicates: n>8. Error bars indicate S. D. For details see Table 1.

FIGS. 3A-3D. tRNA$^{Met}$::$_{DN}$DMC1 movement into flowers and pollen phenotype.

(FIG. 3A) Upper panel: Flowers of non-grafted transgenic plants supported by $_{DN}$DMC1::tRNA$^{Met}$ and tRNA$^{Met}$::$_{DN}$DMC1 are fertile when mock-treated. Lower panel: Application of estradiol inducing $_{DN}$DMC1::tRNA$^{Met}$ and tRNA$^{Met}$::$_{DN}$DMC1 expression resulted in partially sterile anthers, suggesting production of the dominant-negative $_{DN}$DMC1 protein.

(FIG. 3B) Upper panel: Grafted tRNA$^{Met}$::$_{DN}$DMC1/wild-type or wild-type/tRNA$^{Met}$::$_{DN}$DMC1 plants showed partial sterile pollen production when mock-treated. Lower panel: After application of estradiol onto grafted tRNA$^{Met}$::$_{DN}$DMC1/wild-type or wild-type/tRNA$^{Met}$::$_{DN}$DMC1 plants formation of aberrant pollen/sterile anthers in wild-type flowers suggest tRNA$^{Met}$::$_{DN}$DMC1 mRNA transport and expression of the truncated DMC1 protein in wild-type male organs.

(FIG. 3C) RT-PCR assays on poly(A)-RNA samples from transgenic $_{DN}$DMC1::tRNA$^{m}$et (n=6) and tRNA$^{Met}$::$_{DN}$DMC1 (n=7) tissues indicate presence of fusion transcripts in both transgenic and in wild-type scion flowers (red asterisks) suggesting mobility of the tRNA$^{Met}$::$_{DN}$DMC1 fusion transcript over graft junctions. The number of grafted plants tested is shown on the right. ACTIN2 (ACT2) specific RT-PCR was used as a positive control.

(FIG. 3D) Statistical analysis of misshaped pollen appearing on grafted plants (Table 1). Compared to mock-treated control grafts, production of misshaped pollen was significantly higher in estradiol-treated $_{DN}$DMC1::tRNA$^{Met}$ and tRNA$^{Met}$::$_{DN}$DMC1 transgenic plants and in wild-type scions supported by tRNA$^{Met}$::$_{DN}$DMC1. Asterisks indicate statistically significant differences against controls using Chi-square test of independence of variables in a contingency table. Biological replicates: n>8. Error bars indicate S.D. For details see Table 1. Note that >3 independent transgenic $_{DN}$DMC1::tRNA$^{Met}$ or tRNA$^{Met}$::$_{DN}$DMC1 lines were used in the grafting experiments.

FIGS. 4A-4D. GUS::tRNA fusion transcripts and mobility in grafted *Arabidopsis thaliana*.

Figure 5:
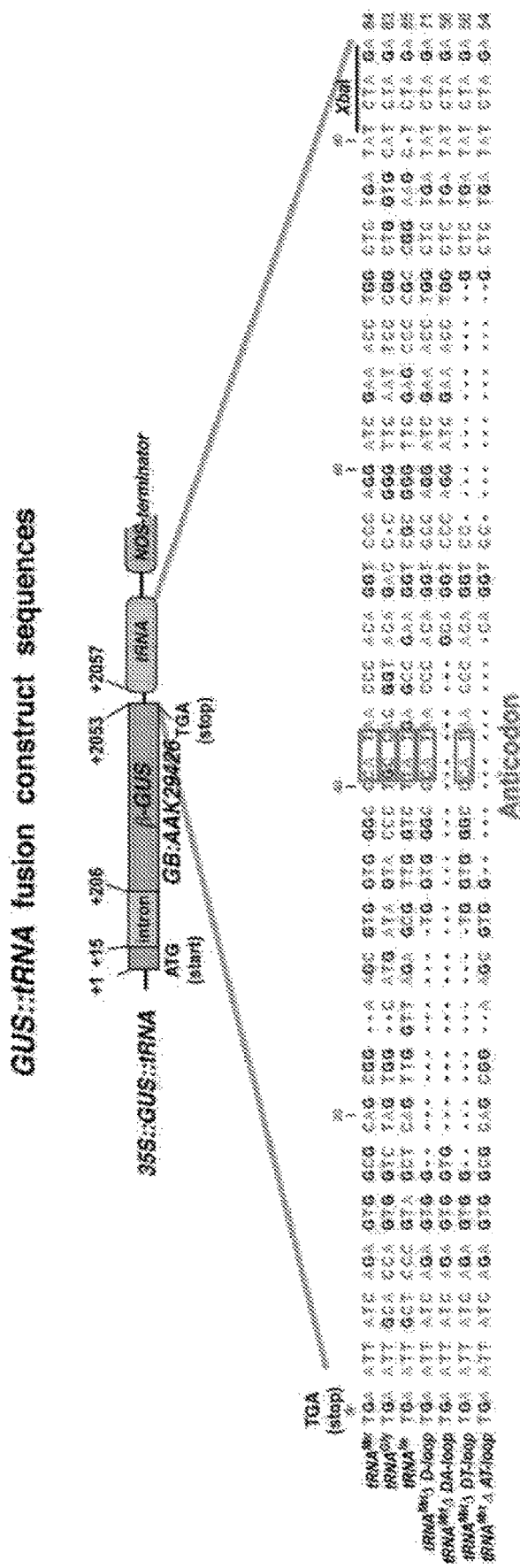

(FIG. 4A) Schematic drawing of used 35S$_{pro}$:GUS::tRNA fusion constructs (for sequences of tRNA$^{Met}$ tRNA$^{Gly}$ tRNA$^{Ile}$, and tRNA$^{Met}$ deletions see FIG. 5).

(FIG. 4B) Example of a hypocotyl grafted GUS::tRNA$^{Met}$/wild-type (Col-0) plant. Blue colour indicates presence of GUS activity in the hypocotyl above the graft junction (arrow) and in the wild-type root tip.

(FIG. 4C) GUS activity in leaves and primary root tips detected in GUS::tRNA/wild-type grafts. The numbers indicate the fraction of GUS staining detected in the wild-type root tips or wild-type leaf vasculature (arrows) of plants grafted with the indicated transgenic line. At least 3 independent transgenic lines were used for each graft combination (for additional images of grafted plants see FIGS. 6A-6B).

(FIG. 4D) RT-PCR on poly(A)-RNA samples harvested from grafted plants. Three samples from 3-5 grafted plants were pooled and tested for presence of GUS transcripts in wild-type tissue (asterisks). Numbers indicate occurrence of GUS poly(A) RNA in the tested wild-type root or wild-type leaves RNA samples. ACTIN2 (ACT2) specific RT-PCR was used as a positive control confirming mRNA presence in the samples.

FIG. 5. tRNA sequences fused to the 3'UTR of GUS.

Alignment of tRNA sequences fused to the GUS coding DNA sequence. The GUS sequence harbouring an intron was fused with tRNA$^{Met}$ (CAU), tRNA$^{Gly}$ (GCC), tRNA$^{Ile}$ (TAT) and deletion variants of tRNA$^{Met}$ (CAU) named tRNA$^{Met}$ ΔD, ΔDA, ΔDT, and ΔAT. The length of tRNA sequences (counted from the GUS ATG start codon) is indicated at the right. Asterisks indicate the GUS TGA stop codon. Red boxes indicate the anticodon sequence of the cloned tRNAs.

Figure 6A:
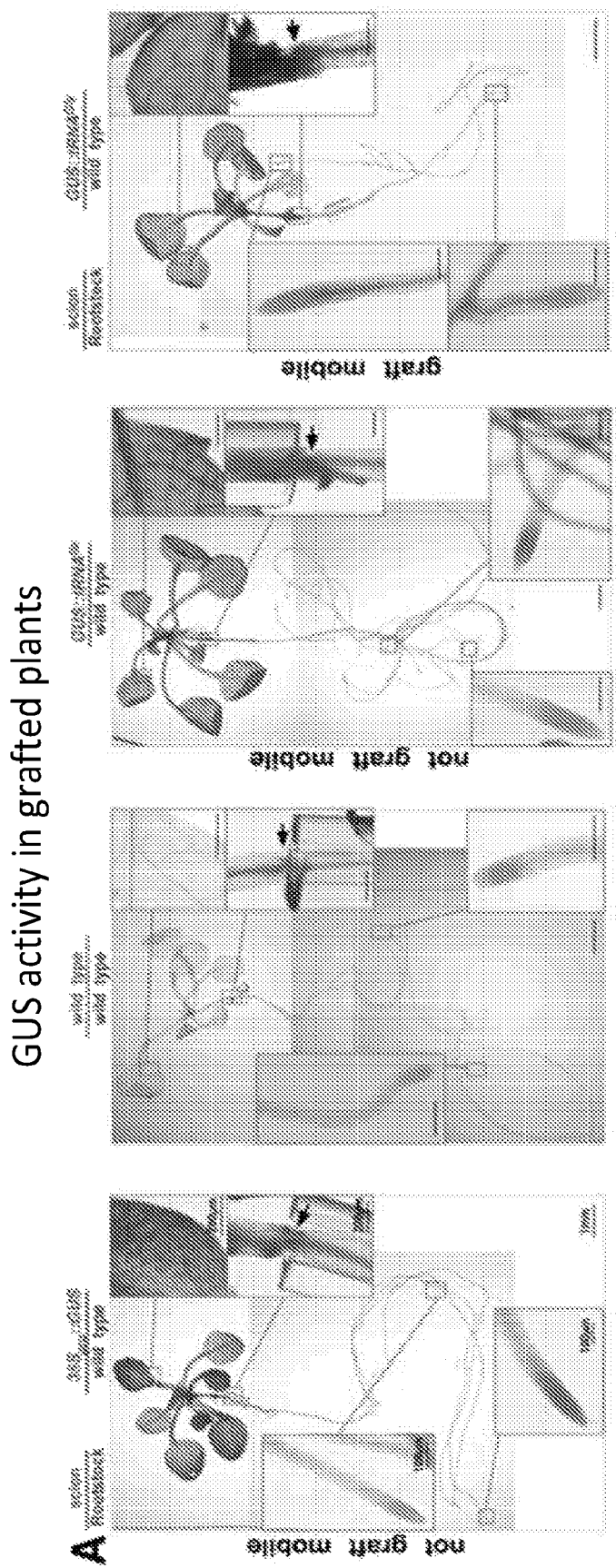
Figure 6A:
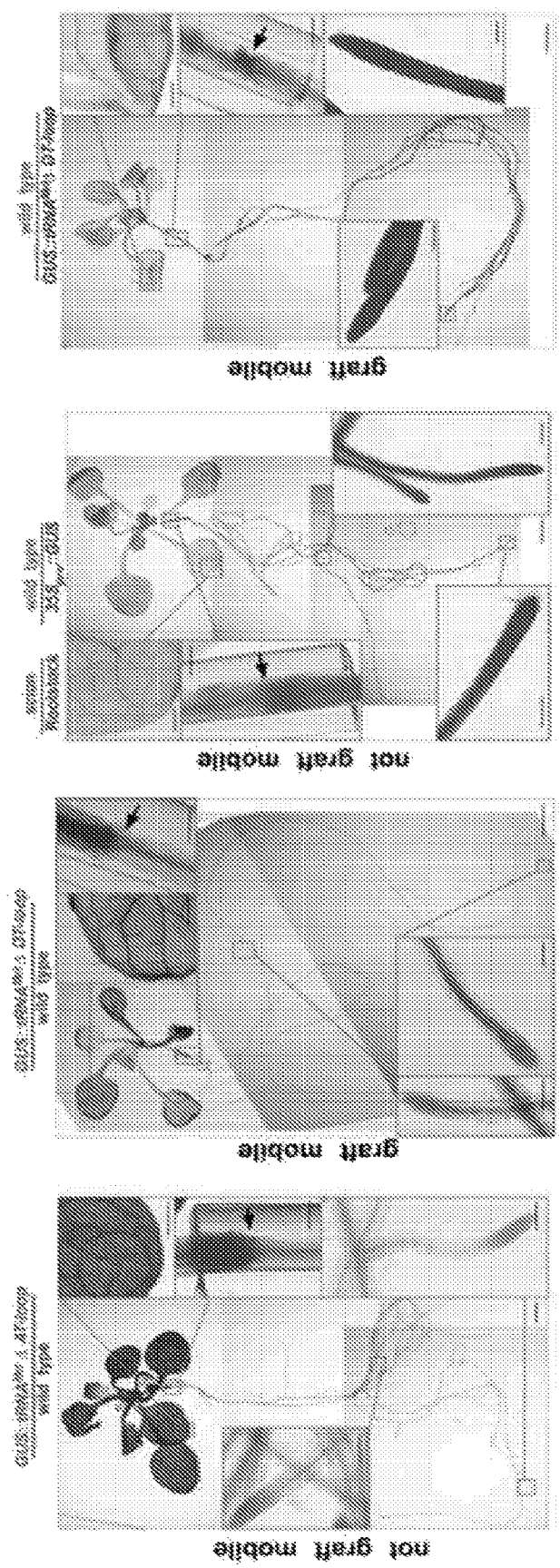
Figure 6B:
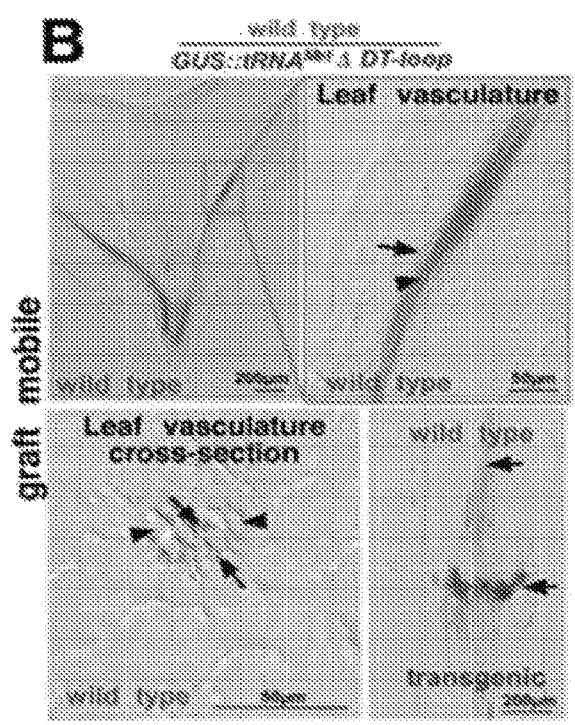

FIGS. 6A-6B. Images of hypocotyl-grafted wild-type/GUS::tRNA transgenic plants.

(FIG. 6A) Example images of *Arabidopsis thaliana* Col-0 plants that were hypocotyl-grafted. The presented wild-type (Col-0)/transgenic plant graft combinations are indicated above. Magnified images of leaf areas, root tips, and graft junction (arrows) are indicated by orange rectangles. Blue coloured tissues in the shown plant parts indicate presence of GUS activity.

(FIG. 6B) Micrographs of thin sections made on a paraffin embedded grafted plant. Wild type was grafted with GUS: tRNA$^{Met}$ ΔDT transgenic stocks. GUS enzymatic activity (blue colour) was detected in vascular cells of wild-type leaves and wild-type hypocotyl in cells associated to the vasculature (arrows). Arrowheads indicate xylem vessels.

FIGS. 7A-7G. Mobile *A. thaliana* mRNAs and occurrence of tRNA-like motifs.

Figure 7A:
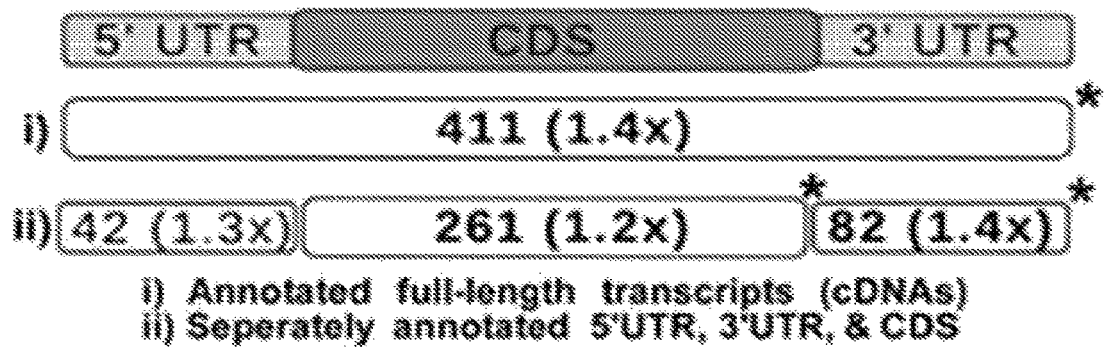
Figure 8A:
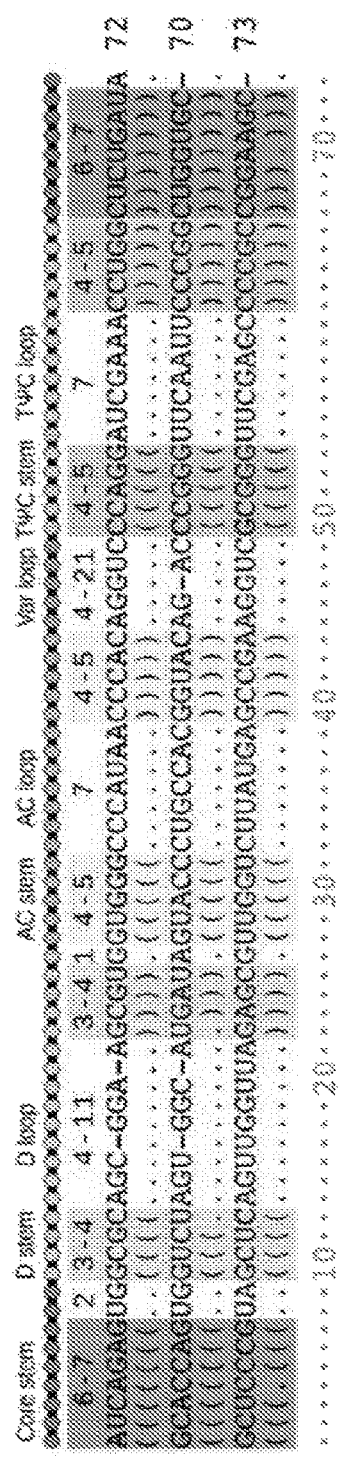
Figure 8B:
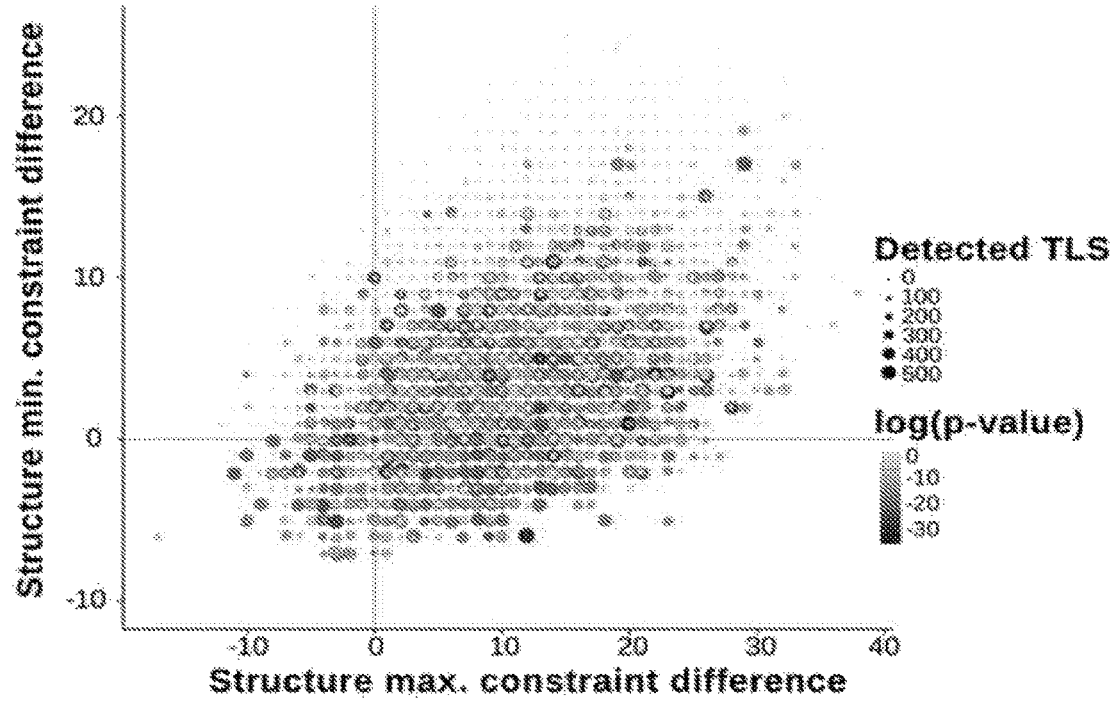
Figure 8C:
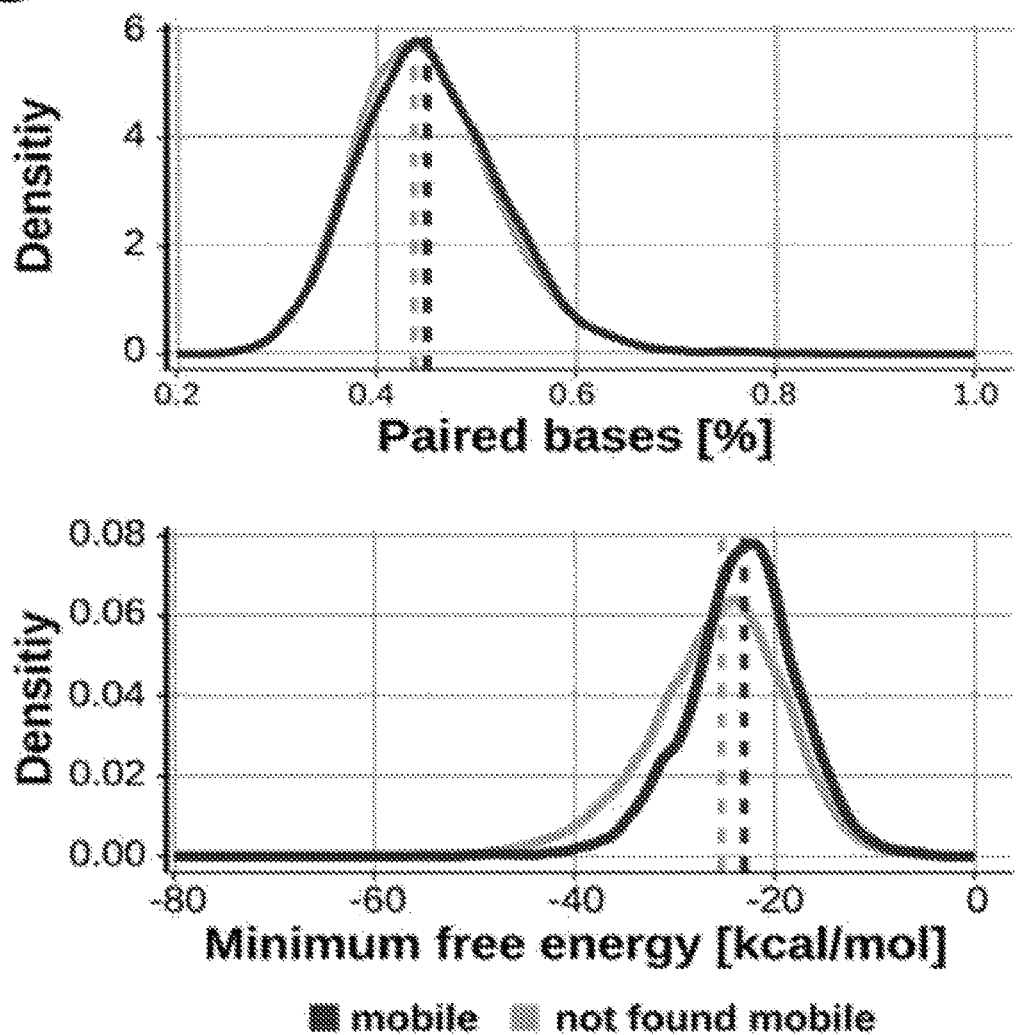

(FIG. 7A) Number of all identified mobile transcripts (n=3630) with predicted tRNA-like structures found by the default RNAMotif tRNA descriptor, which does not capture the tRNA$^{Ile}$ (TAT) (FIGS. 8A-8C). Absolute counts as well as enrichment in relation to transcripts not found in the mobile database are shown. Asterisks indicate significant counts ($p<0.05$) according to Fisher's exact test.

(FIG. 7B) Normalised frequency (estimated density) and cumulative relative frequency (ecdf) of inter-gene distances of tRNA-mRNA tandem gene pairs with the tRNA being located within 1000 nucleotides up- or downstream of genes coding for mobile transcripts (blue) or non-mobile predicted transcripts (grey). Vertical dashed lines indicate medians of shown distributions. Mobile transcript encoding loci in comparison to loci not producing mobile transcript show a significantly closer proximity to tRNA genes (two-sample one-sided Kolmogorov-Smirnov test, $p<0.004$; Cohen's D d=0.349).

(FIG. 7C) Number of tRNA genes according to their anticodon, which were detected as poly(A)-RNA:tRNA bicistronic transcripts in RNA-Seq data. The distribution of the 94 tRNA genes observed bicistronically are given in orange; distribution of the 24 tRNA genes associated with mobile transcripts are shown in blue. The total of TAIR10 annotated tRNA genes is presented in gray. tRNA genes with bicistronic transcripts confirmed by RT-PCR are indicated by asterisks, experimentally tested tRNA fusions are marked by arrows. (FIG. 7D) Schematic diagram of *A. thaliana* CHOLINE KINASE 1 (CK1, AT1G71697) gene and analysed insertion mutants. Note that CK1 mRNA exists as a bicistronic poly(A)—tRNA transcript and that the ck1.2 mutant harbours a T-DNA insertion between the CK1 stop codon and the annotated tRNA$^{Gly}$ (AT1G71700) in the 3' UTR resulting in a truncated poly(A) transcript lacking the tRNA$^{Gly}$ sequences. RT-PCR primers are indicated as follows: P1 binding to exon 7 of CK1 CDS and P3 binding to tRNA$^{Gly}$ sequences were used for wild-type CK1:tRNA$^{Gly}$ identification. P1 together with P2 which is stretching the T-DNA left border and CK1 3'UTR were used for specific ck1.2 detection.

(FIG. 7E) RT-PCR with the indicated primers revealed that the CK1 poly(A) transcript is present in ck1.2 mutant samples (asterisks) originating from stem-grafted wild-type Col-0 tissue. In the reciprocal wild-type samples a mutant CK1 poly(A) transcript produced in ck1.2 and lacking the 3'UTR tRNA$^{Gly}$ sequence was not detected.

(FIG. 7F) Phenotype of ck1.1 and ck1.2 and quantitative Real Time RT-PCR of transcripts. Wild-type and ck1.2 plants show similarly high levels of CK1 expression whereas ck1.1 mutants show very low expression. Rosette area size measurements on adult plants revealed that both ck1.1 and ck1.2 mutants are significantly smaller than wild type (Students T-test, mutant vs. wild type; p-value ck1.1=0.006; p-value ck1.2=0.002; n=16 plants/line). Error bars: S. D.

(FIG. 7G) Schematic folding structure of the GUS TLS 3'UTR motifs predicted according to their minimal free energy (MFE). Structures are shown for GUS::tRNA$^{Met}$ (SEQ ID NO: 111), GUS::tRNA$^{Met}$ ΔD/T loop/stem ("ΔD/T loop/stem"; SEQ ID NO: 112), GUS::tRNA$^{Met}$ ΔA/T loop/stem ("ΔA/T loop/stem"; SEQ ID NO: 113), GUS::tRNA$^{Met}$ ΔD loop/stem ("ΔD loop/stem"; SEQ ID NO: 114), GUS::tRNA$^{Met}$ ΔD/A loop/stem ("ΔD/A loop/stem"; SEQ ID NO: 115), GUS::tRNA$^{Gly(GCC)}$ (SEQ ID NO: 116), and GUS::tRNA$^{Ile(TAT)}$ (SEQ ID NO:117).

FIGS. 8A-8C. Computational analysis of tRNA-like sequences (TLSs) present in mobile mRNAs.

(FIG. 8A) tRNA structure descriptor and structural alignment of tRNA$^{Met}$, tRNA$^{Gly}$, and tRNA$^{Ile}$. The numbers indicate the accepted descriptor ranges of structural elements (stem and loops). Note that the tRNA descriptor does not recognise the structure of the tRNA$^{Ile}$ which did not confer mobility when fused to GUS.

(FIG. 8B) Evaluation of parameter space for the tRNA descriptor constraints. Given a tRNA descriptor model, we tested for enrichment of TLS in mobile relative to non-mobile predicted gene transcripts. The default tRNA descriptor (indicated by a red circle at coordinate origin, p=0.001) indicates an enriched number of hits in mobile transcripts in comparison to non-mobile transcripts. Departure from the default tRNA descriptor parameters is expressed by the sum over differences of the constraint values for the minimum element length (y-axis) as well as by the sum over the maximum element length differences (x-axis). Out of 20,000 produced descriptors, 13,598 that have less than 5,000 gene hits to the non-mobile dataset (excluding tRNA genes) were plotted. Colouring is according to p-values resulting from the counts of motif hits to mobile versus non-mobile transcript sequences (Fisher's exact test), point sizes indicate the number of hits to mobile transcripts. Increasing minimum stem and loop lengths in the RNA structure models result in lower numbers of matches in the mobile transcript dataset. Similarly, relaxing maximum length constraints results in larger number of false positive matches in the non-mobile dataset and, thus, motif hits to mobile versus non-mobile transcripts get less significant.

(FIG. 8C) Degree of structuredness associated with the predicted structure of the 150 nt 3'-terminal sequence region of mobile (n=3,606) vs. non-mobile (n=23,132) predicted mRNAs. Upper graph shows structuredness in terms of number of predicted paired bases. Lower graph in terms of predicted minimum free energy (MFE). The vertical dashed lines denote the medians of the two distributions.

EXAMPLES

Example 1

TRNA$^{Met}$ Fusion Transcripts Move into Flowers

Introduction

To establish a simple phenotypic scoring system for mRNAs harbouring predicted mobility motifs such as TLSs, a dominant-negative A. thaliana DMC1 variant ($_{DN}$DMC1) was used that lacks the N-terminal 92 amino acid residues (FIG. 1A) and that interferes with meiosis progression.

Methods

Plant Material and Growth Conditions

Tobacco (N. tabacum cv. Petite Havana) plants were grown under aseptic conditions on agar-solidified medium containing 30 g L$^{-1}$ sucrose. Rooted tobacco plants were transferred to soil and grown to maturity under standard greenhouse conditions (relative humidity: 55%; day temperature: 25° C.; night temperature: 20° C.; diurnal cycle: 16 h light/8 h darkness; light intensity: 190-600 µE·m$^{-2}$·s$^{-1}$).

Grafting and Estradiol Treatment

Tobacco plants used for grafting experiments were grown two to three months on soil in the greenhouse. A standard splice grafting procedure was used as previously described (Zhang et al., 2014). In short, plants with the same stem diameter carrying five fully expanded leaves were used as stock and scion material; rootstocks were prepared by removing the apical leaves from the top of the plant and keeping two to three source leaves. Scions were prepared by cutting the stem 3 to 4 cm below the apex and removing the source leaves. A long slanting cut was made on the rootstock stem (about 30 degrees from vertical) with a matching cut at the scion base. The surfaces of both cuts were immediately pressed together and the junction was tightly wrapped with parafilm. The first week after grafting the scion was covered with a plastic bag and kept under high humidity.

After the graft junction was established, axillary branches and leaves emerging at the stock were removed in order to enforce apical dominance of the scion. Before flower induction, 50 µM 17-β-estradiol mixed with Lanolin (Sigma-Aldrich) (1000× stock solution: 5 mM 17-β-estradiol in DMSO, stored at −20° C.) was applied with soaked tissue paper onto the adaxial side of stock plant leaf surfaces to induce gene expression. The tissue paper was left on the surface to mark the site of induction. After flowers appeared on the scion, part of the induced leaf and emerging first closed flowers were sampled for fusion transcript presence by RT-PCR.

RNA Isolation and Reverse Transcription Reactions

Samples were prepared in 1 mL Trizol reagent (Invitrogen) (0.5 ml/100 mg tissue) as described previously (Zhang et al., 2009). After centrifugation (10,000 g, 10 minutes at 4° C.), the supernatant (~1 ml) was transferred to a new RNase-free tube and extracted once with 200 and once with 50 µl chloroform. To precipitate the RNA the supernatant was supplemented with two volumes of 99% isopropanol, 0.1 volumes of 3 M sodium acetate (pH 5.2), 1 µg of linear acrylamide (Invitrogen), and incubated>1 h at −20° C. After centrifugation (16,000 g, 30 minutes at 4° C.), the resulting pellet was washed twice with 80% ethanol, once with 99% ethanol, air dried, and resuspended in 20 µl RNase-free water. To determine RNA quality and concentration, 1 µl of each RNA sample was submitted to agarose gel electrophoresis (2%, agarose, 1×TBE) and quantified using a Nano-Drop ND-1000 (Thermo Scientific).

Reverse transcription reaction was performed with 1 U/µl AMV reverse transcriptase (Promega) with following modifications: total RNA (~4 µg) was denatured at 70° C. for 10 minutes in the presence of oligo (dT) primer followed by a 5 minutes annealing incubation at 37° C. prior to the RT-reaction, then incubated at 42° C. for one hour, and 72° C. for 10 minutes for deactivation. RT-PCR was conducted under standard PCR conditions with 40-45 cycles. Oligonucleotides used for RT-PCR are listed in Table 2.

TABLE 2

Oligonucleotides used in the study.

| Construct | Primer sequences | SEQ ID NO | Purpose/Size of PCR fragment |
|---|---|---|---|
| $_{DN}$DMC1::StBEL5 | FK868-F 5'-GATGCTCCGAATCTCGCTGA-3' | 1 | |
| | FK869-R 5'-GTTGCTTGCTGCTGGTGAAG-3' | 2 | 491 bp |
| $_{DN}$DMC1::$_{Met}$tRNA | FK868-F 5'-GATGCTCCGAATCTCGCTGA-3' | 3 | |
| | FK851-R 5'-TTCCGCTGCGCCACTCTGATT-3' | 4 | 260 bp |
| DMC1::$_{Met}$tRNA | FK868-F 5'-GATGCTCCGAATCTCGCTGA-3' | 5 | |
| | FK851-R 5'-TTCCGCTGCGCCACTCTGATT-3' | 6 | 260 bp |
| $_{DN}$DMC1::ZmKNIHD | FK868-F 5'-GATGCTCCGAATCTCGCTGA-3' | 7 | |
| | FK779-R 5'-TAGAAGGCATTGGTGGTG-3' | 8 | 495 bp |
| $_{Met}$tRNA::$_{DN}$DMC1 | FK774-F 5'-ATAACCCACAGGTCCCAG-3' | 9 | |
| | FK771-R 5'-TTCCATTCCCTCCTTTCA-3' | 10 | 422 bp |
| YFP-$_{DN}$DMC1 | FK938-F 5'-CCCGACAACCACTACCTGAG-3' | 11 | |
| | FK858-R 5'-TCATCGAGAGCTTGACACCCTGT-3' | 12 | 353 bp |
| NbActin (GB: X69885) | FK422-F 5'-CACCGGTATTGTGTTGGACTC-3' | 13 | |
| | FK423-R 5'-AGGACCTCAGGACAACGGAAACG-3' | 14 | 303 bp |
| ACTIN2 (At3g18780) | FK424-F 5'-GGAAGGATCTGTACGGTAAC-3' | 15 | 245 bp |
| | FK425-R 5'-TGTGAACGATTCCTGGACCT-3' | 16 | |
| BP primer for CHOLINE KINASE 1 (CK1) T-DNA insertion verification | FK907-F 5'-ATTTTGCCGATTTCGGAAC-3' | 17 | 504-804 bp |
| LP primer salk_023420 | FK908-R 5'-TGGTTCATTACAGGAGAACCG-3' | 18 | 1096 bp |
| RP primer salk_023420 | FK909-F 5'-TTTGTGAATCTCAGGGAATGC-3' | 19 | BP + RP 504-804 bp |
| LP primer salk_070759 | FK914-R 5'-AGCAGCCATCTCACAAAAGTG-3' | 20 | 1012 bp |
| RP primer salk_070759 | FK915-R 5'-TCTAAAACGCGTTTTGCAAAC-3' | 21 | BP + RP 492-792 bp |
| CK1-$_{Gly}$tRNA fusion detection | FK883-F 5'-CTATGGGGAATCATCTCGGG-3' | 22 | 331 bp |
| | FK884-R 5'-CACTAGACCACTGGTGCTTC-3' | 23 | |
| CK1-$_{Gly}$tRNA detection | FK883-F 5'-CTATGGGGAATCATCTCGGG-3' | 24 | 392 bp |
| | FK992-R 5'-CCGTGGCAGGGTACTATCAT-3' | 25 | |
| CK1-$_{Gly}$tRNA mobility detection binding to ck1.2 (salk_023420) | FK883-F 5'-CTATGGGGAATCATCTCGGG-3" | 26 | 309 bp |
| | FK962-R 5'-GTAGACTATATATTGTGGTGTAAAC-3' | 27 | |
| Construction GUS-tRNA fusion forward primer | FK963-F 5'-CTAG CCATGG TAGATCTGAGG-3' | 28 | |
| Construction GUS-$_{Gly}$tRNA reverse primer | FK944-R 5-GCG CGG TGA CCT GCA CCA GCC GGG AAT TGA ACC CGG GTC TGT ACC GTG GCA GGG TAC TAT CAT GCC ACT AGA CCA CTG GTG CAA TTC ACA CGT GAT GGT GAT GGT G-3' | 29 | Size of GUS-Gly tRNA 2141 bp |
| Construction GUS-$_{Met}$tRNA reverse primer | FK945-R 5'-GCG CGG TGA CCT ATC AGA GCC ACC TT CGA TCC TGG GAC CTG TGG GTT ATG GGC CCA CCA CGC TTC CGC TGC GCC ACT CTG ATA ATT CAC ACG TGA TGG TGA TGG TG-3' | 30 | Size of GUS-Met tRNA 2141 bp |
| Construction GUS-$_{Ile}$tRNA reverse primer | FK946-R 5'-GCG CGG TGA CCG CTT CCG GCG GGG CTC GAA CCC GCG ACC TTC GGC TCA TAA GAC CAA CGC TCT AAC CAA CTG AGC TAC GGG AGC AAT TCA CAC GTG ATG GTG ATG GTG-3' | 31 | Size of GUS-Met tRNA 2142 bp |
| Construction GUS-$_{Met}$tRNA D loop deletion (dD) reverse primer | FK948-R 5'-GCG CGG TGA CCT ATC AGA GCC AGG TTT CGA TCC TGG GAC CTG TGG GTT ATG GGC CCA CCA CCA CTC TGA TAA TTC ACA CGT GAT GGT GAT GGT G-3' | 32 | Size of GUS-Met tRNA dD 2128 bp |
| Construction of GUS-$_{Met}$tRNA D Anticodon loop deletion (dDA) reverse primer | FK950-R 5'-GCG CGG TGA CCT ATC AGA GCC AGG TTT C GAT CCT GGG ACC TGC CAC CAC TCT GAT AAT TCA CAC GTG ATG GTG ATG GTG-3' | 33 | Size of GUS-Met tRNA dDT 2113 bp |
| Construction GUS-$_{Met}$tRNA D and TΨC loop deletion (dDT) reverse primer | FK949-R 5'-G CGC GGT GAC CTA TCA GAG CGG ACC TGT GGG TTA TGG GCC CAC CAC CAC TCT GAC AAT TCA CAC GTG ATG GTG ATG GTG-3' | 34 | Size of GUS-Met tRNA dDA 2113 bp |
| Construction GUS-$_{Met}$tRNA Anticodon and TΨC loop deletion (dAT) reverse primer | FK947-R 5'-GC GCG GTG ACC TAT CAG AGC GGA CCT GCC ACG CTT CCG CTG CGC CAC TCT GAT AAT TCA CAC GTG ATG GTG ATG GTG-3' | 35 | Size of GUS-Met tRNA dAT 2111 bp |
| Adding $_{Met}$tRNA + XbaI + BstEII reverse primer | FK951-R 5'-gcgc GGTGACC TCTAGA TATCAGAGC-3' | 36 | |
| Adding $_{Gly}$tRNA + XbaI + BstEII reverse primer | FK952-R 5'-gcgc GGTGACC TCTAGA TGCACC-3' | 37 | |
| Adding $_{Ile}$tRNA XbaI + BstEII reverse primer | FK953-R 5'-gcgc GGTGACC TCTAGA GCTTCCGG-3' | 38 | |

TABLE 2-continued

Oligonucleotides used in the study.

| Construct | Primer sequences | SEQ ID NO | Purpose/Size of PCR fragment |
|---|---|---|---|
| GUS mobility test | FK1091-F 5' CAACAGCTTCCGGACCGCAC-3' | 39 | 428 bp |
|  | FK1092-R 5' GATTGAGCGCGATGACGTCA-3' | 40 |  |
| GUS-$_{Met}$tRNA mobility | FK1079-F 5' CGAGTACTACCAGGCGAACC-3' | 41 | 316 bp |
|  | FK1081-R 5' CAGAGCCAGGTTTCGATCCTG-3' | 42 |  |
| GUS-$_{Gly}$tRNA mobility | FK1079-F 5' CGAGTACTACCAGGCGAACC-3' | 43 | 281 bp |
|  | FK1086-R 5' GCAGGGTACTATCATGCCAC-3' | 44 |  |
| GUS-$_{Ile}$tRNA mobility | FK1080-F 5' ACCACGTCGTGTTCGATGAG-3' | 45 | 272 bp |
|  | FK1085-R 5' GGCTCATAAGACCAACGCTC-3' | 46 |  |
| Construction of GUS-$_{Met}$tRNA D loop deletion (dD) reverse primer | FK1079-F 5' CGAGTACTACCAGGCGAACC-3' | 47 | 316 bp |
|  | FK1081-R 5' CAGAGCCAGGTTTCGATCCTG-3' | 48 |  |
| GUS-$^{Met}$tRNA D and TΨC loop deletion (dDT) mobility verification | FK1080-F 5' ACCACGTCGTGTTCGATGAG-3' | 49 | 255 bp |
|  | FK1083-R 5' GTTATGGGCCCACCACCACTC-3' | 50 |  |
| GUS-$_{Met}$tRNA D and Anticodon loop deletion (dDA) mobility verification | FK1079-F 5' CGAGTACTACCAGGCGAACC-3' | 51 | 274 bp |
|  | FK1084-R 5' GATCCTGGGACCTGCCAC-3' | 52 |  |
| GUS-$_{Met}$tRNA Anticodon and TΨC loop deletion (dAT) reverse primer | FK1079-F 5' CGAGTACTACCAGGCGAACC-3' | 53 | 292 bp |
|  | FK1082-R 5' GCTGCGCCACTCTGATAATTC-3' | 54 |  |
| GUS mobility Poly A primer | FK1099-F 5' AGAACGCTAGCCATCACCATC-3' | 55 | 127 bp |
|  | FK1100-R 5'GCCAAATGTTTGAACGATCGGG-3' | 56 |  |
| GUS mobility poly A primer | FK1099-F 5' AGAACGCTAGCCATCACCATC-3' | 57 | 135 bp |
|  | FK1090-R 5'GCAAGACCGGCAACAGGAT-3' | 58 |  |
| GUS detection by QRT-PCR | FK1093-F 5' CGCGTCCAAGGGAAACAAGAAG-3' | 59 | 142 bp |
|  | FK1094-F 5' TTCACACGTGATGGTGATGGTGA-3' | 60 |  |
| Actin2 primer QRT-PCR (AT3G18780) | FK1097-F 5' TCCCTCAGCACATTCCAGCAGAT-3' | 61 | 69 bp |
|  | FK1098-F 5' AACGATTCCTGGACCTGCCTCATC-3' | 62 |  |
| UBQ10 primer QRT-PCR (AT4G05320) | FK1095-F 5' CACACTTCACTTGGTCTTGCGT-3' | 63 | 61 bp |
|  | FK1096-R 5' TAGTCTTTCCGGTGAGAGTCTTCA-3' | 64 |  |
| CK1 and mutant detection by QRT-PCR | FK1105-F 5' ATCTTCTGGGGACTATGGGGA-3' | 65 | 126 bp |
|  | FK1106-R 5' TCATCCTTCAAGAAGCAAAGGC-3' | 66 |  |
| CK1 and mutant detection by QRT-PCR | FK1107-F 5' TCATACACGCCAGAACTCTTTC-3' | 67 | 198 bp |
|  | FK1108-R 5' CCAACCGATACTTATCCATCTCTA-3' | 68 |  |
| AT3G01700-tRNA$^{Pro}$ bicistronic poly A RT-PCR | FK1122-F 5'-CCGGATTCTTCATCTTCTCTCTCT-3' | 69 | 305 bp |
|  | FK1123-R 5'-CCTAAGCGAGAATCATACCACTAGACC-3' | 70 |  |
| tRNA$^{Pro}$-AT3G01710 bicistronic poly A RT-PCR | FK1124-F 5'-GTTACAGTAGCAGAGAGGTCTTACA-3' | 71 | 280 bp |
|  | FK1125-R 5'-CGAGTTCAATTCTCGGAATGCC-3' | 72 |  |
| tRNA$^{Pro}$-AT3G01710 bicistronic poly A RT-PCR | FK1126-F 5'-CAACAGACCAAACTAAGAAAGCTC-3' | 73 | 305 bp |
|  | FK1125-R 5'-CGAGTTCAATTCTCGGAATGCC-3' | 74 |  |
| AT4G34030-tRNA$^{Arg}$ bicistronic poly A RT-PCR | FK1127-F 5'-CCTTTAGAAGATACTCGATTTGGTGTC-3' | 75 | 257 bp |
|  | FK1128-R 5'-GTCTGATTAGAAGTCAGACGCCT-3' | 76 |  |
| tRNA$^{Arg}$-AT4G34040 bicistronic poly(A) RT-PCR | FK1129-F 5'-CGACATAAAAGCACCGTTCC-3' | 77 | 514 bp |
|  | FK1130-R 5'-GGCCCAATGGATAAGGCGT-3' | 78 |  |
| AT5G03740-tRNA$^{Leu}$ bicistronic poly A RT-PCR | FK1131-F 5'-CAGTGCAGCTGCTTGAGAAGA-3' | 79 | 453 bp |
|  | FK1132-R 5'-GTCTTCCCCCTTAACCACTCG-3' | 80 |  |
| tRNA$^{Leu}$-AT5G03740 bicistronic poly A RT-PCR | FK1133-F 5'-GGTTTGCCCGAGTGGTTAAG-3' | 81 | 548 bp |
|  | FK1134-R 5'-GACAAGGTGCAGCTTCTTTGA-3' | 82 |  |
| AT5G41600-tRNA$^{Leu}$ bicistronic poly A RT-PCR | FK1135-F 5'-CTCTGAACAAGAAGAAGGATTAAGG-3 | 83 | 741 bp |
|  | FK1136-R 5'-CCTTAGACCACTCGGCCATC-3' | 84 |  |
| tRNA$^{Leu}$-AT5G41610, bicistronic poly A RT-PCR | FK1137-F 5'-GACTTCTACGGATAAAGACTCTGA-3' | 85 | 399 bp |
|  | FK1138-R 5'-TCTAAGGCGCCAGACTCAAG-3' | 86 |  |
| AT4G14410-tRNA$^{Thr}$ bicistronic poly A RT-PCR | FK1139-F 5'-GCCTCCTGCTGCTTAAACTCT-3' | 87 | 277 bp |
|  | FK1140-R 5'-GTAAGCGGGAGGTCTTGAGT-3' | 88 |  |
| tRNA$^{Thr}$-AT4G14420 bicistronic poly A RT-PCR | FK1141-F 5'-GCTCCAAAGGCAAAAGCAAAC-3' | 89 | 430 bp |
|  | FK1142-R 5'-AACGGGTGCTCTAACCAACT-3' | 90 |  |
| AT2G33130-tRNA$^{Met}$ bicistronic poly A RT-PCR | FK1143-F 5'-GCTAGCGCGTAGGTCTCATA-3' | 91 | 638 bp |
|  | FK1144-R 5'-GAAGCAAAGCTGCCGAGATG-3' | 92 |  |
| AT2G33130-tRNA$^{Met}$ bicistronic poly A RT-PCR | FK1143-F 5'-GCTAGCGCGTAGGTCTCATA-3' | 93 | 697 bp |
|  | FK1145-R 5'-TTCTCCACCGTCCATGCAAT-3' | 94 |  |
| RNA$^{Met}$-AT2G33150 bicistronic poly A RT-PCR | FK1146-F 5'-CGCTCGCTAGAGAGGACCAT-3' | 95 | 432 bp |
|  | FK1147-R 5'-GACCTACGCGCTAGCCAACT-3' | 96 |  |
| AT4G27870-tRNA$^{Gln}$ bicistronic poly A RT-PCR | FK1148-F 5'-CTGAAACTGAATCTTGCCTGGAG-3' | 97 | 284 bp |
|  | FK1149-R 5'-GGACTCTGAATCCAGTAACCCG-3' | 98 |  |
| Actin2 (At3g18780) | FK1152-F 5'-ACTTTCATCAGCCGTTTTGA-3' | 99 | 190 bp |
|  | FK1153-R 5'-ACGATTGGTTGAATATCATCAG-3' | 100 |  |

Expression Constructs

To produce a dominant-negative AtDMC1 with a N-terminal 92 amino acid deletion in *A. thaliana* DMC1 ($_{DN}$DMC1) transcripts with 3'UTR and 5'UTR fusions an expression binary constructs named pRD1 and pRD4 were created based on a pMDC7 (Curtis and Grossniklaus, 2003) backbone. The $_{DN}$DMC1 fragment was introduced 5' or 3' of the pMDC7 gateway cloning cassette which resulted in a template binary vector used to clone via a gateway reaction the RNA sequences of StBEL5, or tRNA$^{Met}$ between the $_{DN}$DMC1 ORF and promoter or terminator (FIG. 1A).

Synthetic oligonucleotides were used to produce gateway ENTRY clones with the according sequence for gateway recombination with the binary vector (Table 2). The binary vector constructs based on pMDC7 allow estradiol-induced $_{DN}$DMC1:RNA or RNA::$_{DN}$DMC1 expression. pEarlyGate104 used for 35S$_{pro}$:YFP-$_{DN}$DMC1 expression and the DMC1 siRNA *N. tabacum* line (35S$_{pro}$:BcDMC1 hpRNAi) and its function was previously described (Zhang et al., 2014).

Microscopy and Pollen Shape Analysis

The statistical pollen shape analysis indicating sterility was performed as described previously (Zhang et al., 2014). Tobacco pollen was collected and stained with propidium iodide (0.01 mg/ml, Molecular Probes, USA). To image the shape and size of the pollen a Confocal Laser-Scanning Microscope (CLSM; TCS SP5; Leica Microsystems) was used. The system had the following settings: Detection Channel 2 (red): 570-650 nm. The Channel 2 gain (PMT) was set between 500-600 V, Pinhole: 1.0 Airy Units, 5 Z-stacks with 5-6 µm were merged and used for the shape recognition algorithm as described (Zhang et al., 2014).

YFP fluorescence was detected as described (Zhang et al., 2014) with following settings: Sequential channel scan mode with a maximum aerial pinhole of 1.5 Airy Units. To compare the YFP fluorescence intensity between plants the same settings such as laser power, gain voltage, pinhole, objective, magnification, and channel/filter wavelengths were used. Z-stack images were assembled and processed using the Image J software package (NIH). Detection Channel 1 (green): 535 to 617 nm; Detection Channel 2 (red): not used; Detection Channel 3 (blue; Chloroplast/plastid autofluorescence): 695 to 765 nm Channel 1 gain (PMT) was set between 500-600 V.

Results

DMC1 is a specific meiotic cell-cycle factor and a member of the highly conserved RecA-type recombinase family of DNA-dependent ATPases active during meiosis in sporogenic cells. Lack of a functional DMC1/RAD51 complex induces achiasmatic meiosis resulting in the formation of anomalously shaped pollen containing an aberrant number of chromosomes and, consequently, is necessary for proper pollen development. Thus, production of misshaped pollen in anthers and decreased fertility serve as a readout, indicating the presence of mobile DMC1 siRNA (FIGS. 1B-1C) and/or the presence of a translation product of a mobile dominant-negative $_{DN}$DMC1 mRNA.

To implement an mRNA mobility reporter system, transgenic *Nicotiana tabacum* plants were produced expressing $_{DN}$DMC1 mRNA fused to the known mobile full-length StBEL5 transcript (Cho et al., 2015) ($_{DN}$DMC1:: StBEL5) and a full-length tRNA$^{Met}$ (AT5G57885; $_{DN}$DMC1::tRNA$^{Met}$, tRNA$^{Met}$::$_{DN}$DMC1) (FIG. 1A) which was detected in the phloem sap of pumpkin. Plants expressing these constructs were verified to show a pollen sterility phenotype (FIGS. 1D-1E) and they were used in grafting experiments (FIGS. 1F-1G) to evaluate transcript mobility from transgenic source tissue to wild-type flowers.

Figure 2A:
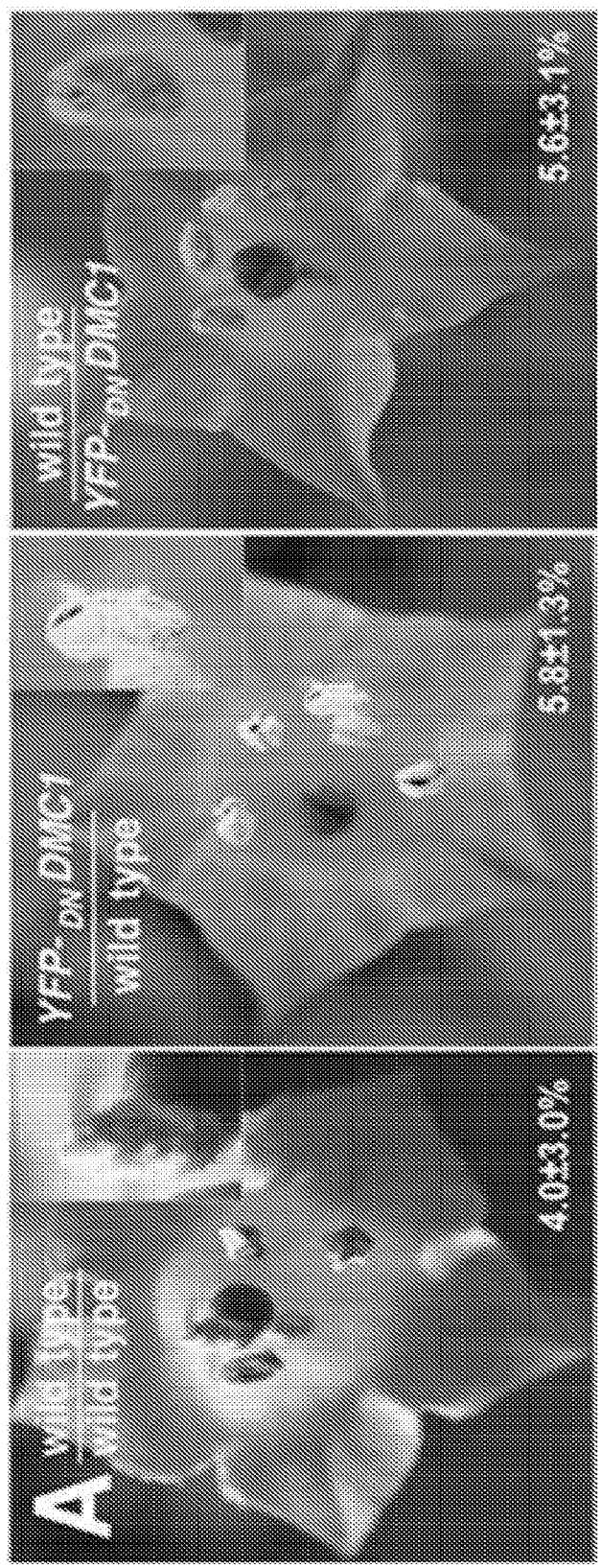
Figure 2B:
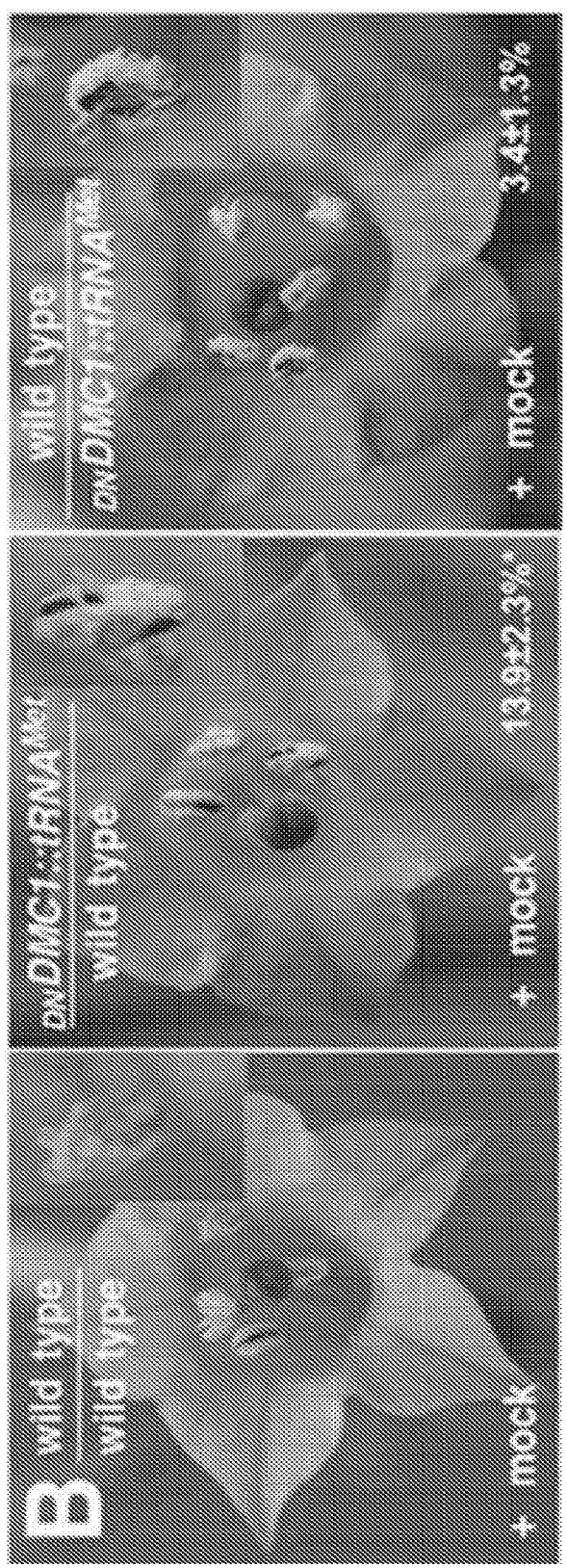
Figure 2B:

It was first confirmed by RT-PCR that $_{DN}$DMC1 itself is not mobile and, thus, is suitable as a transcript mobility reporter producing a pollen phenotype (FIG. 2A). Next, the mobility of the fusion transcripts was addressed by grafting $_{DN}$DMC1::StBEL5, $_{DN}$DMC1::tRNA$^{Met}$ or tRNA$^{Met}$::$_{DN}$DMC1 transgenic plants with wild-type plants, and pollen sterility and the presence of the fusion transcript in wild-type flowers examined (FIGS. 2B-2G; FIGS. 3A-3D).

Figure 2C:
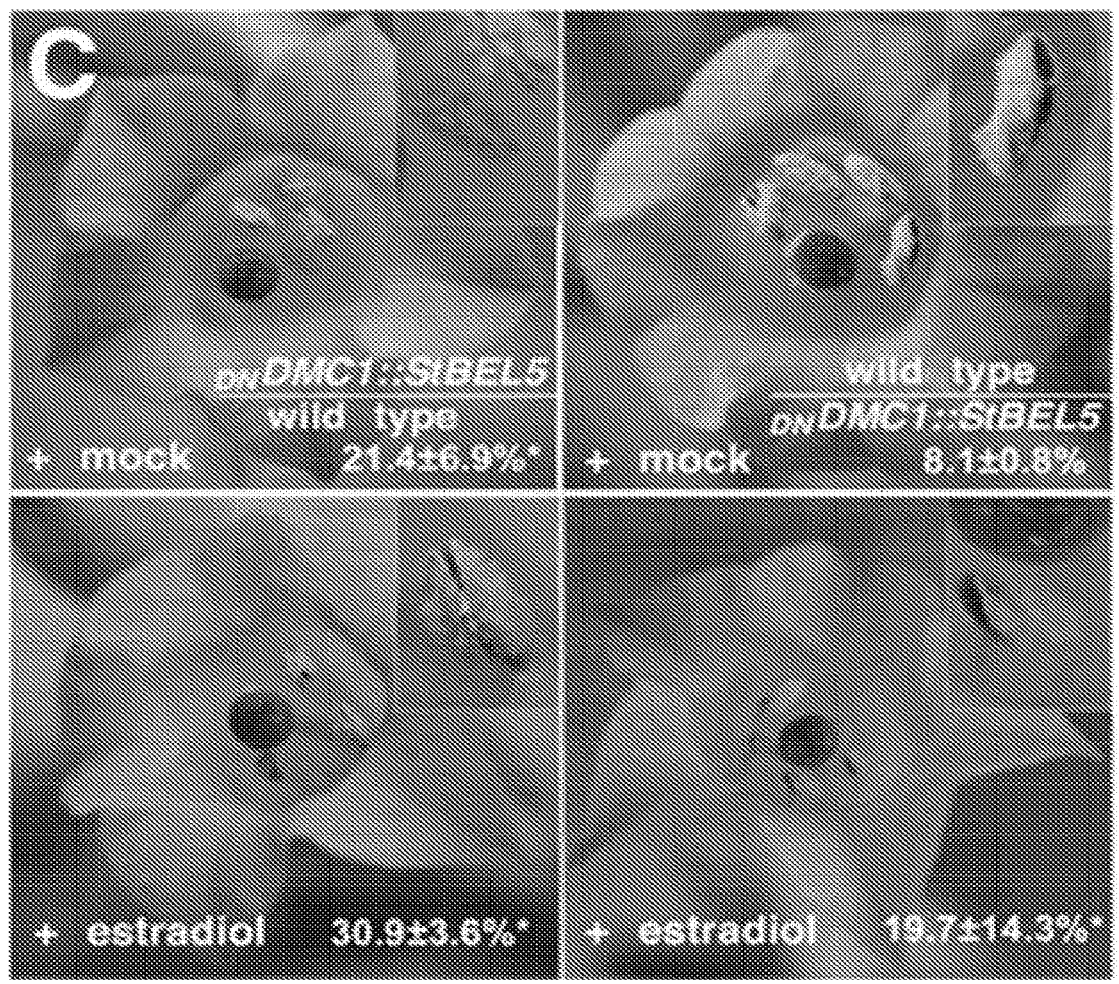
Figure 2D:
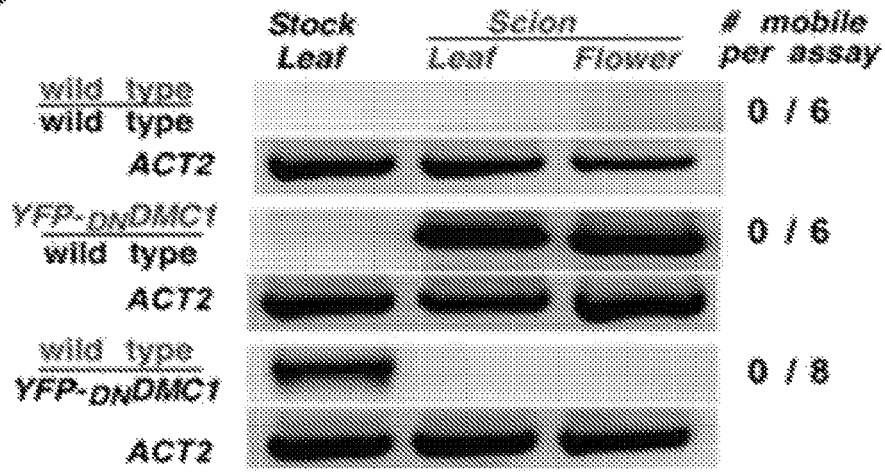
Figure 2E:
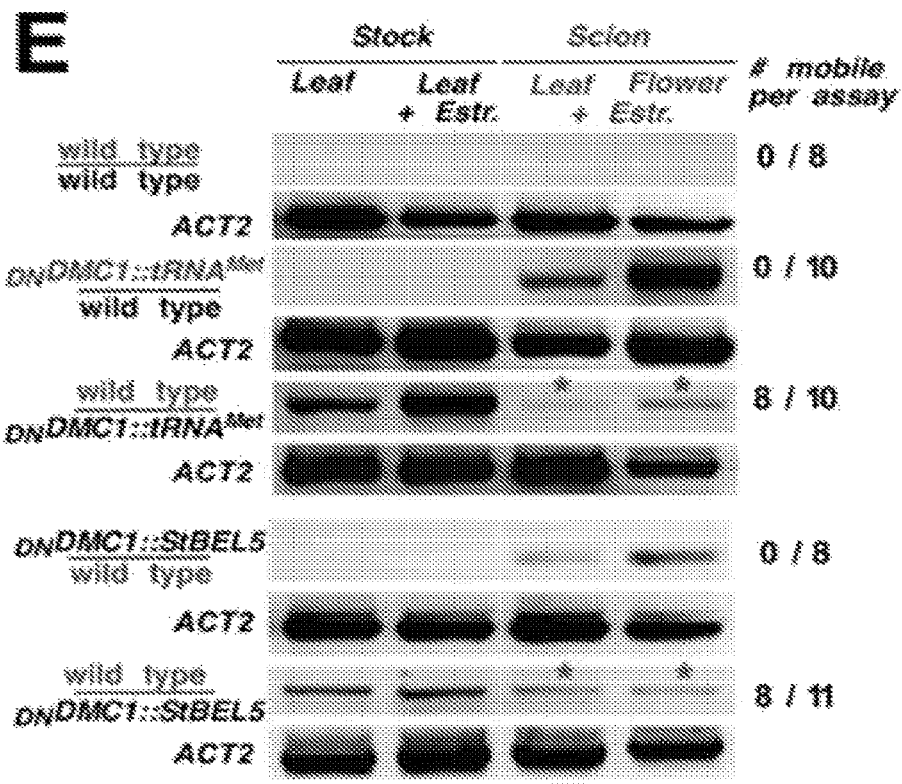

As expected, after induction with estradiol, the $_{DN}$DMC1::StBEL5 scions grafted onto wild-type stocks showed a significantly higher percentage of aberrant pollen formation in their flowers (30.9±7.6%) than grafted wild-type plants (4.0±3.0%) (FIG. 2C; Table 1). Confirming that StBEL5 fusion transcripts are mobile, wild-type plants grafted onto $_{DN}$DMC1::StBEL5 stocks produced a significantly higher number of misshaped pollen (19.7±14.3%) than wild-type controls and the presence of fusion transcript was confirmed by RT-PCR in closed wild-type flowers (FIG. 2E). Thus, $_{DN}$DMC1-RNA fusion constructs can be employed as an RNA mobility reporter system by producing a quantifiable pollen phenotype.

Next, to learn whether a phloem-allocated tRNA contains the necessary structural information mediating mRNA movement over long-distances, transgenic plants expressing the 3'UTR $_{DN}$DMC1::tRNA$^{Met}$ (FIG. 2B) or the 5'UTR tRNA$^{Met}$::$_{DN}$DMC1 (FIGS. 3A-3D) fusion construct were grafted. Expression was induced by applying estradiol to the transgenic source leaves (stock) or transgenic stem (scion) ~1.5 weeks after grafting and prior to flower induction. Estradiol-treated grafted plants formed a significantly higher number of misshaped pollen (14.2±7.6%; Table 1) compared to control grafts and wild-type plants (FIGS. 2A-2B), and RT-PCR assays confirmed the presence of $_{DN}$DMC1::tRNA$^{Met}$ and tRNA$^{Met}$::$_{DN}$DMC1 poly(A) transcripts in wild-type flowers formed on transgenic stock plants (FIG. 2E, FIGS. 3A-3D).

TABLE 1

Pollen shape analysis on wild-type, transgenic, and grafted *Nicotiana tabacum* plants.

| | Scion/Stock | # of plants with visual pollen sterility (# of plants) | # independent lines | # of pollen analyzed (# plants) | % misshaped pollen | P-value | Significance |
|---|---|---|---|---|---|---|---|
| Controls | hpDMC1 siRNA | 10 (10) | 3 | 5101 (10) | 78.08 ± 10.86% | 0.0 | *** |
| | wild type | 0 (10) | 3 | 5365 (10) | 7.51 ± 2.59% | — | ns |
| | YFP-$_{DN}$DMC1 | 0 (6) | 3 | 947 (4) | 3.27 ± 1.84% | — | ns |
| Control grafts | Wild type/wild type (before estradiol induction) | 0 (12) | 3 | 1187 (7) | 4.04 ± 3.00% | — | ns |
| | Wild type/wild type (after estradiol induction) | 0 (6) | 3 | 643 (6) | 3.27 ± 3.96% | — | ns |

TABLE 1-continued

Pollen shape analysis on wild-type, transgenic, and grafted Nicotiana tabacum plants.

| | Scion/Stock | # of plants with visual pollen sterility (# of plants) | # independent lines | # of pollen analyzed (# plants) | % misshaped pollen | P-value | Significance |
|---|---|---|---|---|---|---|---|
| | Wild type/YFP-$_{DN}$DMC1 | 0 (8) | 3 | 1068 (4) | 5.62 ± 3.10% | — | ns |
| | YFP-$_{DN}$DMC1/ wild type | 0 (6) | 2 | 3664 (5) | 5.84 ± 1.31% | — | ns |
| | YFP-$_{DN}$DMC1/ YFP-$_{DN}$DMC1 | 0 (6) | 4 | 824 (3) | 4.13 ± 2.83% | — | ns |
| $_{DN}$DMC1::tRNA$^{Met}$ grafts | Wild type/ $_{DN}$DMC1::tRNA$^{Met}$ (before estradiol induction) | 0 (6) | 3 | 239 (3) | 3.35 ± 1.32% | — | ns |
| | Wild type/ $_{DN}$DMC1::tRNA$^{Met}$ (before estradiol induction) | 11 (17) | 8 | 1525 (6) | 14.23 ± 7.60% | 3.76e−24 | *** |
| | $_{DN}$DMC1::tRNA$^{Met}$/ wild type (before estradiol induction) | 3 (6) | 3 | 416 (3) | 13.94 ± 2.28% | 3.78e−10 | *** |
| | $_{DN}$DMC1::tRNA$^{Met}$/ wild type (after estradiol induction) | 16 (19) | 9 | 2331 (8) | 38.65 ± 22.46% | 7.52e−270 | *** |
| | YFP-$_{DN}$DMC1/ $_{DN}$DMC1::tRNA$^{Met}$ (after estradiol induction) | 2 (5) | 2 | 374 (1) | 10.96 ± 0.00% | 0.00417 | ** |
| $_{DN}$DMC1::StBEL5 grafts | Wild type/ $_{DN}$DMC1::StBEL5 (before estradiol induction) | 0 (4) | 2 | 433 (2) | 8.08 ± 0.76% | 0.51261 | ns |
| | Wild type/ $_{DN}$DMC1::StBEL5 (after estradiol induction) | 10 (14) | 4 | 1398 (10) | 19.67 ± 14.33% | 3.60e−65 | *** |
| | $_{DN}$DMC1::StBEL5/ Wild type (before estradiol induction) | 3 (4) | 2 | 243 (2) | 21.40 ± 6.92% | 9.04e−65 | *** |
| | $_{DN}$DMC1::StBEL5/ Wild type (before estradiol induction) | 12 (14) | 6 | 1200 (5) | 30.92 ± 7.56% | 8.43e−221 | *** |
| tRNA$^{Met}$::$_{DN}$DMC1 grafts | Wild type/ tRNA$^{Met}$::$_{DN}$DMC1 (before estradiol induction) | 0 (4) | 2 | 398 (2) | 5.28 ± 2.02% | — | ns |
| | Wild type/ tRNA$^{Met}$::$_{DN}$DMC1 (after estradiol induction) | 14 (21) | 4 | 2291 (8) | 14.80 ± 14.73% | 2.42401e−27 | *** |
| | tRNA$^{Met}$::$_{DN}$DMC1/ Wild type (before estradiol induction) | 2 (4) | 2 | 332 (3) | 9.04 ± 1.78% | 0.01835 | * |
| | tRNA$^{Met}$::$_{DN}$DMC1/ Wild type (after estradiol induction) | 18 (22) | 6 | 4540 (12) | 26.81 ± 18.68% | 1.34e−177 | *** |
| Non-grafted transgenic plants | $_{DN}$DMC1::tRNA$^{Met}$ (before estradiol induction) | 3 (6) | 6 | 723 (2) | 17.48 ± 5.83% | 4.10e−22 | *** |
| | $_{DN}$DMC1::tRNA$^{Met}$ (after estradiol induction) | 6 (6) | 6 | 555 (4) | 38.74 ± 15.32% | 3.92e−115 | *** |
| | $_{DN}$DMC1::StBEL5 (before estradiol induction) | 2 (5) | 5 | 709 (4) | 5.92 ± 2.61% | — | ns |
| | $_{DN}$DMC1::StBEL5 (after estradiol induction) | 5 (5) | 5 | 313 (3) | 56.87 ± 6.24% | 1.77e−175 | *** |
| | tRNA$^{Met}$::$_{DN}$DMC1 (before estradiol induction) | 3 (6) | 6 | 637 (2) | 25.27 ± 9.91% | 5.15e−56 | *** |

TABLE 1-continued

Pollen shape analysis on wild-type, transgenic, and grafted Nicotiana tabacum plants.

| Scion/Stock | # of plants with visual pollen sterility (# of plants) | # independent lines | # of pollen analyzed (# plants) | % misshaped pollen | P-value | Significance |
|---|---|---|---|---|---|---|
| tRNA$^{Met}$::$_{DN}$DMC1 (after estradiol induction) | 5 (6) | 6 | 287 (3) | 37.28 ± 4.45% | 1.29e-84 | *** |

Asteriks indicate statistical significance regarding the enhanced number of misshaped pollen against wild-type control using Chi-square test of independence of variables in a contingency table (ns - not significant, * p-value ≤ 0.05,  p-value ≤ 0.01, * p-value ≤ 0.001)

Figure 2F:
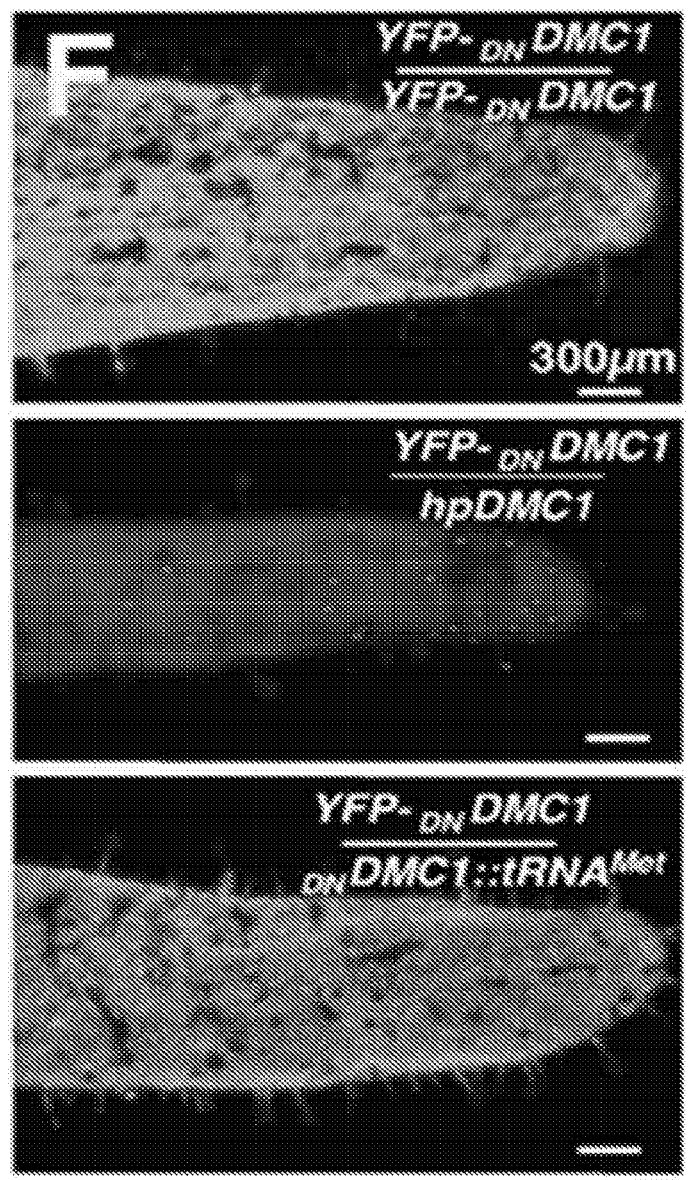
Figure 2G:
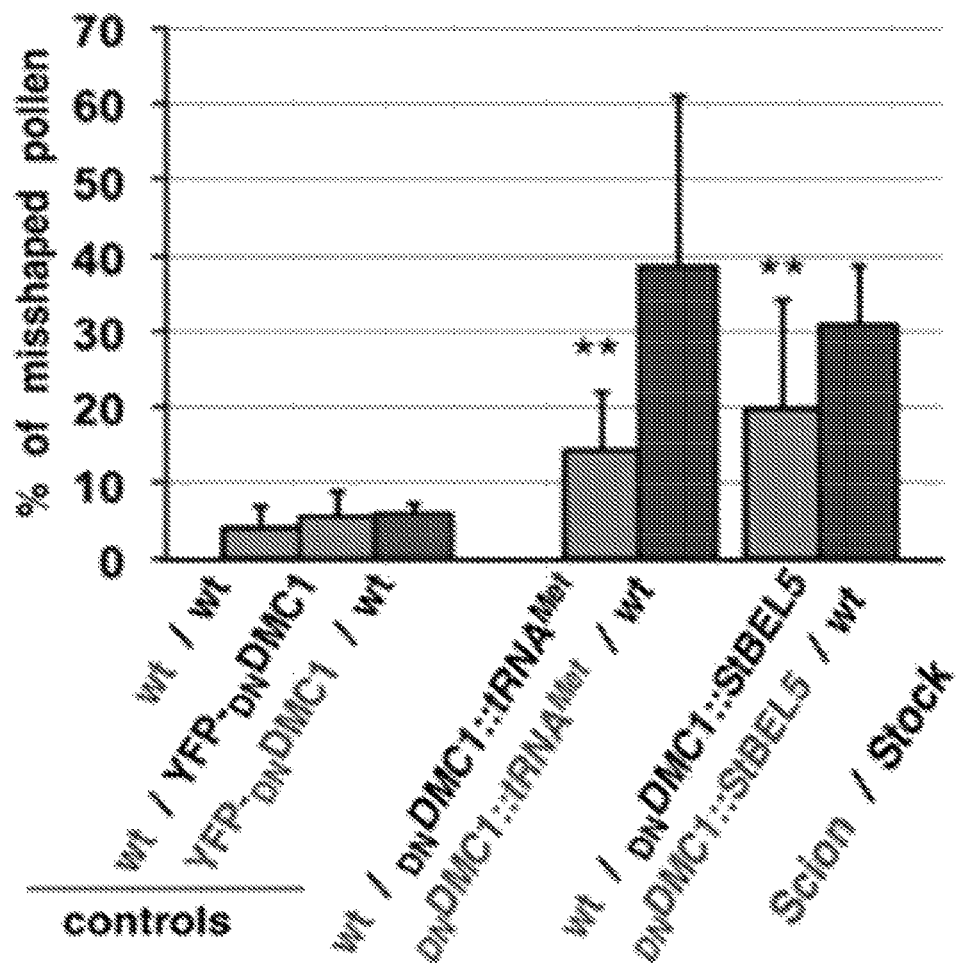
Figure 3A:
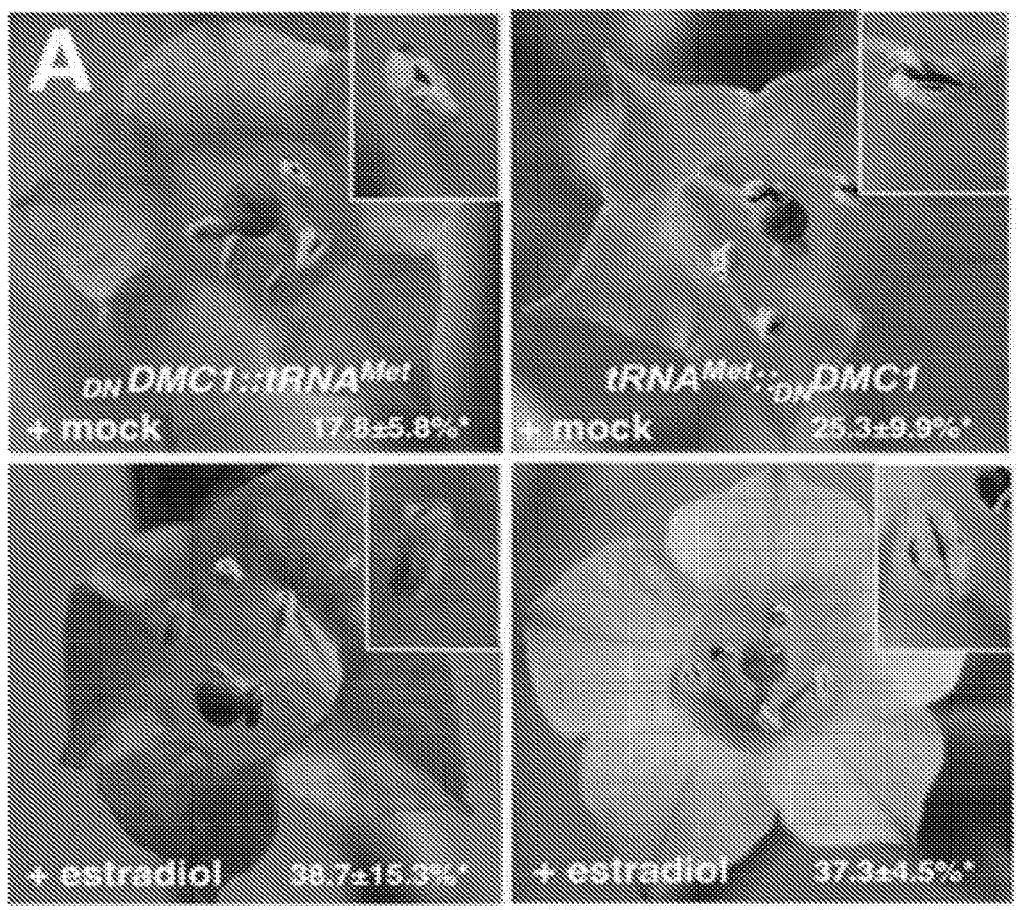
Figure 3B:
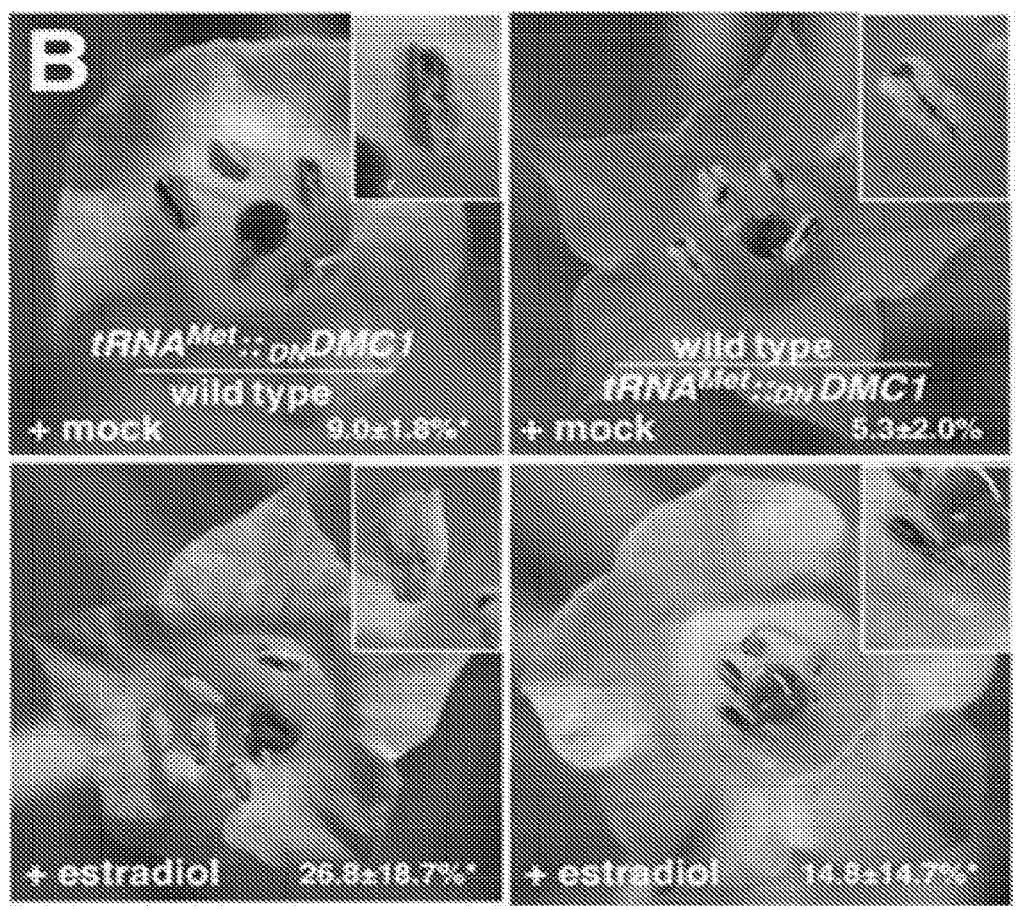
Figure 3C:
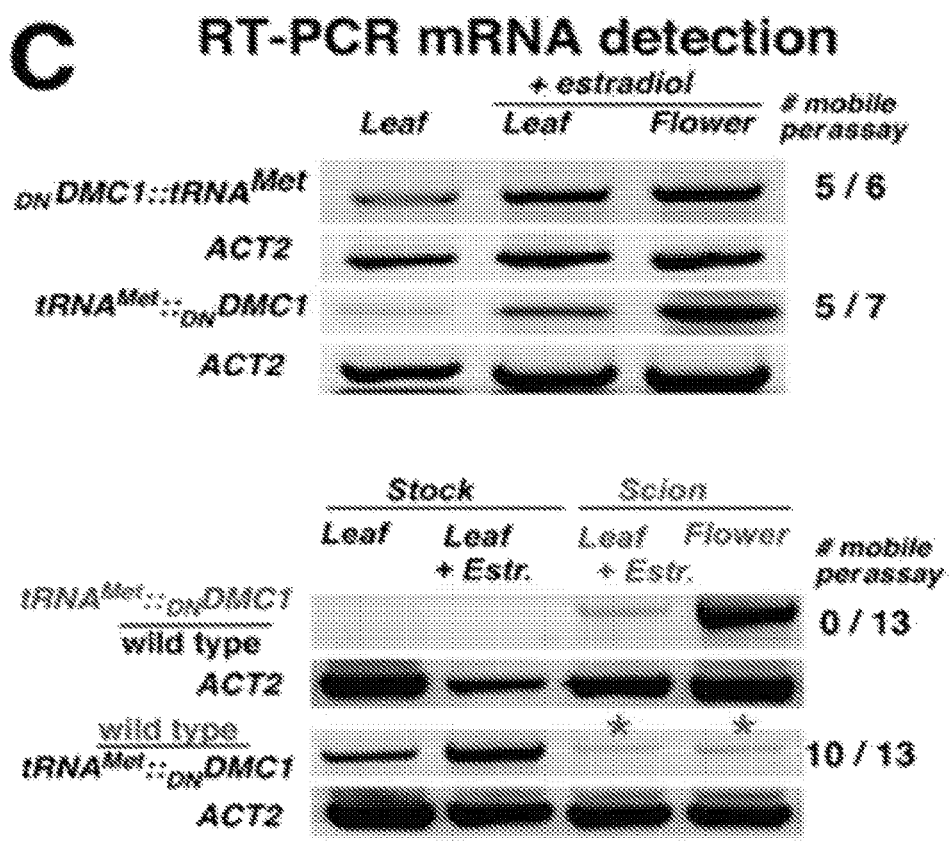
Figure 3D:
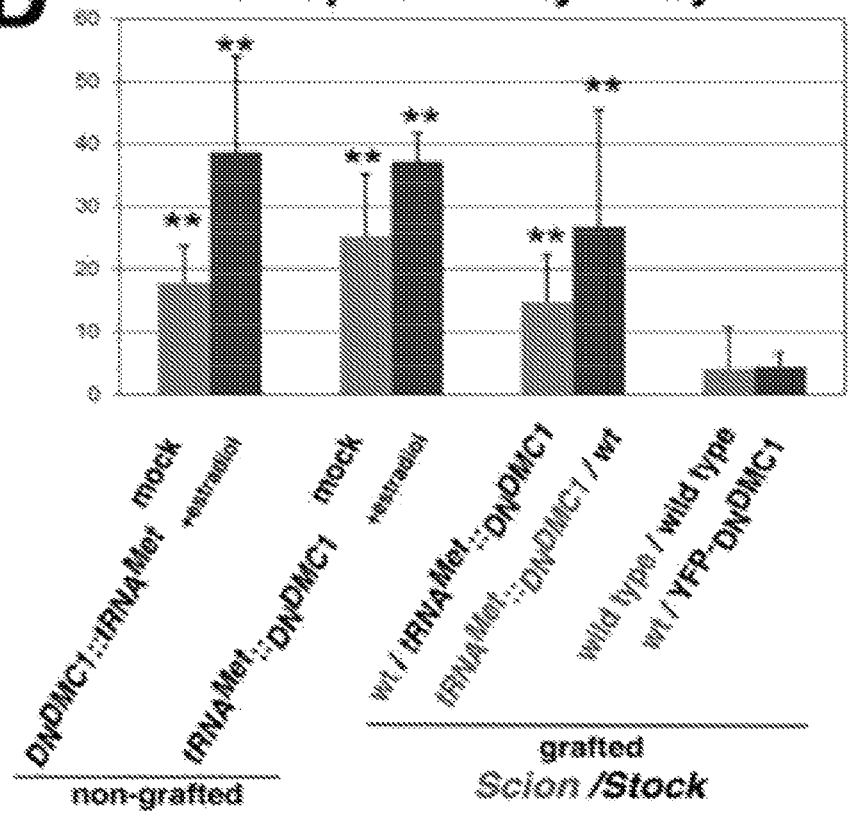

To exclude the possibility that the grafted chimeric plants produce a mobile DMC1 siRNA silencing signal that moves into the wild-type flower tissues and triggers a pollen sterility phenotype, the $_{DN}$DMC1:tRNA$^{Met}$ plants with a reporter line producing a yellow fluorescent YFP-$_{DN}$DMC1 fusion protein were grafted. In contrast to the DMC1 siRNA control lines, no systemic siRNA mediated silencing of the YFP-$_{DN}$DMC1 reporter construct could be detected in sepals (FIG. 2F). Thus, the $_{DN}$DMC1::tRNA$^{Met}$ fusion transcript does not induce systemic silencing, and the observed defects in pollen formation in grafted plants (FIG. 2G) can be attributed to the systemic delivery of the $_{DN}$DMC1 fusion transcripts.

In summary, presence of the full-length tRNA' sequence in the 5' or 3' UTR triggers transport of the $_{DN}$DMC1 poly(A) transcript from stock to source leaves and into sporogenic tissues, where it is translated as it interferes with meiosis in male tissues.

Example 2 tRNAs Harbour a Signal for Systemic mRNA Movement

To evaluate whether particular tRNA sequences related to viral TLS mediate systemic mRNA movement, the core tRNA sequences of the phloem-imported tRNA$^{Met}$ (72 bases; TAIR #AT5G57885) and tRNA$^{Gly}$ (74 bases; TAIR #AT1G71700), and the non-phloem imported tRNA$^{Ile}$ (73 bases; TAIR #AT3G05835) (Zhang et al., 2009) were fused to the 3'UTR of the cell-autonomous β-GUS mRNA sequence (FIG. 4A, FIG. 5). To evaluate the mobility of the fusion transcripts, A. thaliana Col-0 lines expressing 35S$_{pro}$:GUS or 35S$_{pro}$:GUS::tRNA fusion constructs were produced and hypocotyl-grafted with Col-0 wild type (shoot or root).

Methods

Plant Material and Growth Conditions

A. thaliana seeds of wild type (Col-0), and transgenic 35S$_{pro}$:β-GUS, ck1.1 (SALK_070759), ck1.2 (SALK_023420) plants of ecotype Col-0 were used and grown in controlled environmental chambers for growth assays or on soil in the greenhouse (relative humidity: 60%; day temperature: 22° C.; night temperature: 19° C.; diurnal cycle: 16 h light/8 h darkness; light intensity: 170-200 μE·m$^{-2}$·s$^{-1}$). The SALK-lines were obtained from the Salk Institute Genomic Analysis Laboratory, California (Alonso et al., 2003).

Grafting

A. thaliana hypocotyl grafting was performed as described (Thieme et al., 2015). In short, plants were grown vertically on solid 0.5 MS medium (1% sucrose) at 22° C. with a photoperiod of 8 h light (fluence rate of 100 μmol m$^{-2}$ s$^{-1}$). The temperature was increased to 26° C. 4 days after germination to reduce adventitious root formation. 6 to 7 days after germination seedlings were used for grafting under sterile conditions as described (Thieme et al., 2015).

In short, seedlings were cut transversely in the middle of the hypocotyl with a razor blade (Dumont; No. 5), and a silicon collar (NeoTecha; Ø0.30×0.60 mm) was slid over the stock in which the scion was inserted. Grafted plantlets were placed on solid 0.5 MS medium (supplemented with 1% agar and 1% sucrose) and grown at 22° C. (8 h light). Appearing adventitious roots were cut every two days and after two weeks successfully grafted plants were submitted to histochemical GUS stain assays, or root and shoot materials were harvested separately for RT-PCR detection of GUS transcripts.

Expression Constructs

GUS fusion constructs harbouring tRNA$^{Met}$ (AUG), tRNA$^{Gly}$ (GGC), or tRNA$^{Ile}$ (AUA) and tRNA$^{Met}$ (AUG) variants in the 3'UTR were created by PCR amplification using an NcoI GUS forward primer covering the GUS start codon and by a BstEII GUS reverse primer covering the GUS stop codon and the tRNA sequence. The resulting PCR fragment was amplified again with an unspecific XbaI reverse primer harbouring an XbaI site for identification of the cloned fragment. The resulting NcoI-BstEII digested fragments were cloned into the accordingly digested pCambia1305.1 (Chen et al., 1998) allowing expression of the GUS::tRNA constructs driven by a 35S promoter. All synthetic oligonucleotides used in the PCR reactions are listed in Table 2.

β-Glucuronidase (GUS) Detection

Histochemical reactions with substrate X-Gluc were performed with plant material incubated in 80% Acetone for 20 minutes at −20° C., washed 2× with 50 mM NaPO$_4$ buffer pH 7.0. The staining solution (1 mM X-Gluc diluted in 25 mg/ml, in 50 mM NaPO$_4$ pH 7.0 buffer, supplemented with 2 mM Potassium Ferricyanide, 2 mM Potassium Ferrocyanide, 0.1% Triton X-100) was vacuum infiltrated for 15 minutes. The staining reaction was carried out at 37° C. overnight and stopped by rinsing the tissues three times in 70% ethanol for 1 h.

The stained plant material was examined by stereomicroscopy (Leica, DFC300, FX). For thin sections, GUS stained samples were dehydrated in an ethanol series including a fixation step 20% ethanol, 35% ethanol, 50% ethanol, FAA prepared fresh (50% ethanol, 3.7% Formaldehyde, 5% acetic acid), 70% ethanol for 30 minutes each at room temperature. Then the samples were embedded in paraffin using the enclosed tissue processor Leica ASK300S and the embedding centre Leica EG1160. 10 μm and 20 μm longitudinal and traverse sections were placed on poly L-Lysine-coated slides.

After drying the samples overnight at 42° C. the slides were de-waxed twice in histoclear for 10 minutes and then incubated twice in 99.8% ethanol for 10 minutes under constant movement at room temperature. After drying overnight the cover slips were mounted with Entellan new (Merck Millipore) and examined by an epi-fluorescence microscope (BX61, Olympus).

Bioinformatic Analysis tRNA Motif Scans

Reference sequences of all protein-encoding genes [available cDNA sequence data associated with all protein-coding *Arabidopsis* genes, TAIR10 (Lamesch et al., 2012), excluding organellar genomes] were partitioned into distinct sets based on their annotation as mobile or non-mobile as detected in heterografted *Arabidopsis* accessions or Cuscuta-parasite *Arabidopsis*-host interactions (Thieme et al., 2015). Subsets were generated for genes common to both mobile sets (n=486), present in at least one of them (n=3606), as well as according to the observed movement direction (root-to-shoot, shoot-to-root, and bidirectional). All genes and associated transcripts assigned as non-mobile were used as controls. All sets were filtered for duplicate sequences, and annotated tRNA genes were removed. tRNA sequence data were obtained from the tRNAdb (Juhling et al., 2009). Prior to structure motif scans, each sequence was padded with 50 "N" leading and trailing characters to facilitate the detection of terminally located tRNA structures without asymmetric ends at the tRNA acceptor arm which are required by the default tRNA descriptor. All sets were analysed by RNAMotif version 3.1.1 (Macke et al., 2001) using the provided tRNA structure descriptor and default parameter settings. Motif enrichment associated with genes encoding mobile transcripts compared to background data was assessed by Fisher's exact test. Specificity of the searched tRNA-like structure was assessed by permutation scans of the default tRNA descriptor.

20,000 different tRNA descriptors were produced by randomly altering the accepted minimum and maximum lengths limits for the stems and the single-stranded loops in the model (normal distribution using μ=0, sigma=5; minimum stem length set to 3 nt). Each descriptor was evaluated against the mobile/non-mobile data by RNAMotif with default settings. Structuredness; i.e. the percentage of base-paired nucleotides and associated energetics, within the 3'UTR was addressed by excising the 150 nt 3'-terminal sequence portion and subsequent analysis of its predicted secondary structure (RNAfold, default settings).

tRNA-mRNA Tandem Scans

Genes adjacent to tRNA loci were identified according to TAIR10 gene models including protein-coding, non-coding genes, and pseudogenes. Statistical significance of the difference of gene proximity distributions (distances between tRNA-genes and mobile vs. non-mobile gene neighbours) was estimated by the non-parametric Kolmogorov-Smirnov test (1-sided test); relevance was assessed by the effect size (Cohen's D) based on the mean observed differences and associated standard deviations.

Bicistronic tRNA Analysis

*A. thaliana* reference genome (TAIR10) sequence information was obtained from The *Arabidopsis* Information Resource (The *Arabidopsis* Information Resource), associated gene model descriptions (gtf version 10.30) were taken from plants.ensembl.org. Paired-end RNA-Seq data (100 nt reads from both ends) was retrieved from the Sequence Read Archive (SRA) (NIH: National Library of Medicine: Sequence Read Archive), accessions SRX853394 (14.1G bases, root sample) and SRX853395 (15.3G bases, shoot sample) (Thieme et al., 2015) as well as DRX014481 (19G bases, root sample) and DRX014482 (32.7G bases, root sample). Read data were quality trimmed and Illumina adapter sequences were clipped by using Trimmomatic (Lohse et al., 2012) standard settings (ILLUMINACLIP: <adapterfile>:2:40:15, LEADING:3, TRAILING:3, SLIDINGWINDOW:4:15, and MINLEN:36).

Mapping of sequences mate pairs to the *A. thaliana* reference genome (TAIR10) was done by STAR v2.5.1 (Dobin et al., STAR: ultrafast universal RNA-seq aligner, Bioinformatics 2012) based on Ensembl gene model descriptions. Considering the high number of tRNA genes in the *Arabidopsis* genome and their similar sequences, reads with multiple alignments were excluded, minimum overhang for gene junctions was set to 10 nt for annotated junctions and 20 nt for unannotated junctions, maximum number of allowed mismatches per pair was 10 nt (outFilterMultimapNmax 1, alignSJDBoverhangMin 10, alignSJoverhangMin 20, outFilterMismatchNmax 10).

Subsequently, all read pairs mapping to chromosomes 1 to 5 with a minimum alignment quality Q≥10 were checked to be intersecting with both, tRNA and mRNA gene annotations. Finally, identified 132 bicistronic poly(A)-RNA:: tRNA transcripts were grouped by their tRNA gene identity (118 unique tRNA genes, FIG. 7C) as well as by the protein-coding gene (120 unique genes) and the assigned transcript mobility. Results were compared to the list of annotated tRNA-mRNA tandems and statistical significance for the observed overlap to the bicistronic transcripts was assessed by Fisher's exact test.

Results

Figure 4D:
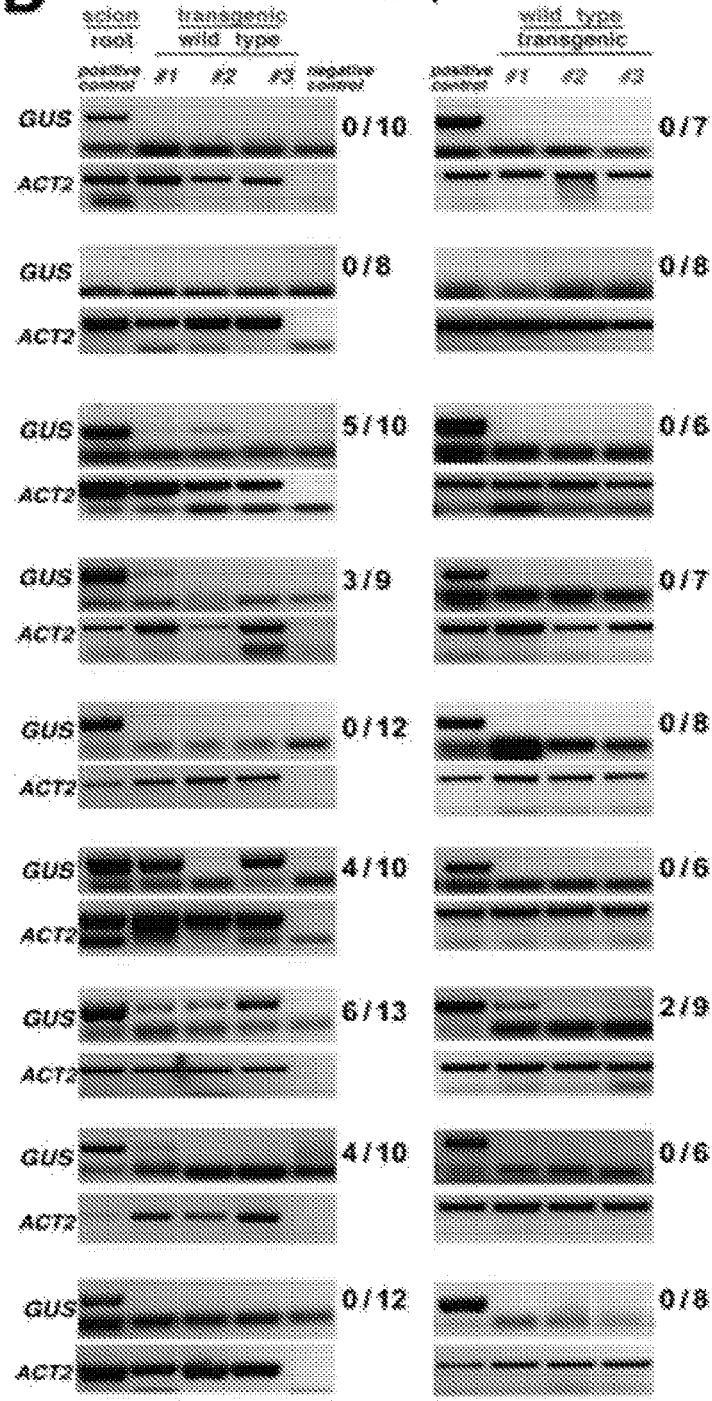

Two weeks after grafting, GUS enzyme activity was visualised in situ (FIGS. 4B-4C; FIG. 6). Control grafts with transgenic $35S_{pro}$:GUS plants lacking the tRNA sequences in the 3' UTR showed no GUS activity and GUS mRNA presence in distant wild-type root (n=0/55 grafts) or leaf (n=0/43 grafts) tissues, indicating that neither the GUS mRNA nor the GUS protein moves over grafting junctions (FIGS. 4C-4D).

However, GUS activity was detected in phloem-associated cells in wild-type roots after hypocotyl-grafted with transgenic scion plants expressing GUS::tRNA$^{Met}$ (n=9/44 grafts) or GUS::tRNA$^{Gly}$ (n=6/25 grafts). No GUS activity was observed in wild-type roots grafted with plants expressing GUS::tRNA$^{Ile}$ (n=0/57 grafts). Again, RT-PCR assays confirmed the presence of GUS::tRNA$^{Met}$ and GUS::tRNA$^{Gly}$, and the absence of GUS::tRNA$^{Ile}$ transcripts in wild-type roots after grafting (FIG. 4D). Notably, the reverse grafts with transgenic roots and wild-type scions indicate that the shoot-to-root mobile GUS::tRNA$^{Met}$ fusion transcript is not moving from root to shoot (n=0/36 grafts) and that GUS::tRNA$^{Gly}$ barely moves from root to shoot (n=3/26 grafts).

To learn whether the entire tRNA sequence is required or whether a subsequence is sufficient to mediate mRNA mobility, tRNA$^{Met}$ deletion constructs lacking the assigned dihydrouridine (D)-, anticodon (A)-, or TψC (T)-arm/loop structures and combinations thereof (FIG. 4C) were used. Again, plants expressing these GUS mRNA fusion constructs were grafted with wild-type plants and then tested for GUS activity and for fusion transcript presence. As indicated by GUS and RT-PCR assays, the ΔD, ΔDT, and ΔDA, but not the ΔAT tRNA$^{Met}$ deletion construct, were sufficient to mediate GUS transport into wild-type roots and, with a very low frequency, to scion leaves (FIGS. 4C-4D). Presence of the GUS::ΔDtRNA$^{Met}$ transcript and translation in phloem-associated cells of wild-type roots and leaves shows that only part of the tRNA$^{Met}$ sequence is required to trigger mobility. This also demonstrates that A- and TψC hairpin-loop sequences have redundant roles in triggering mRNA transport as only deletions of both, the A and TψC hairpin-loop sequences, eliminated mobility of the GUS fusion transcript.

Figure 7B:
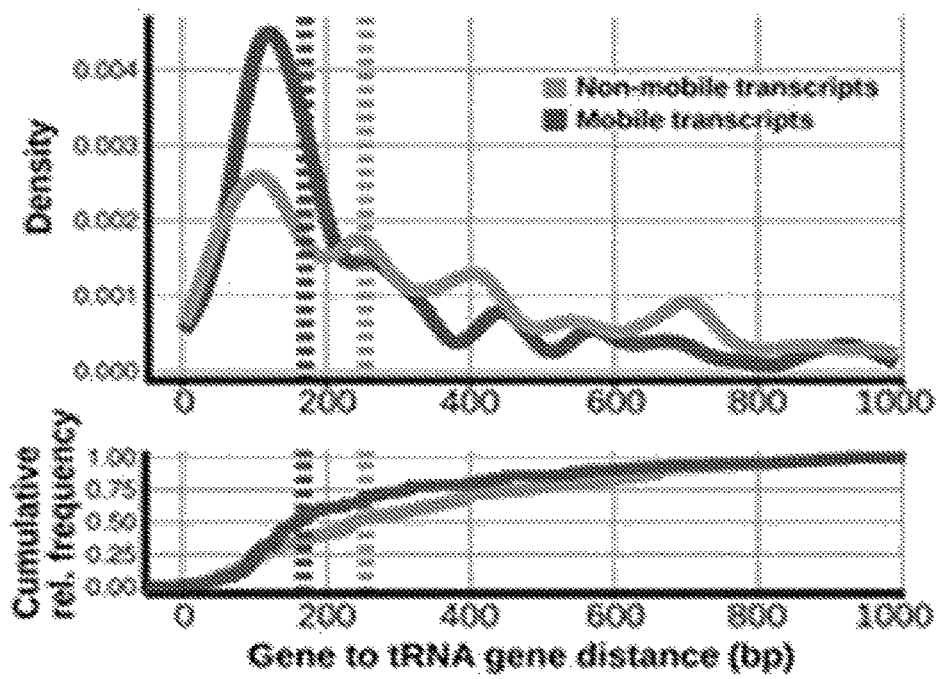
Figure 7C:
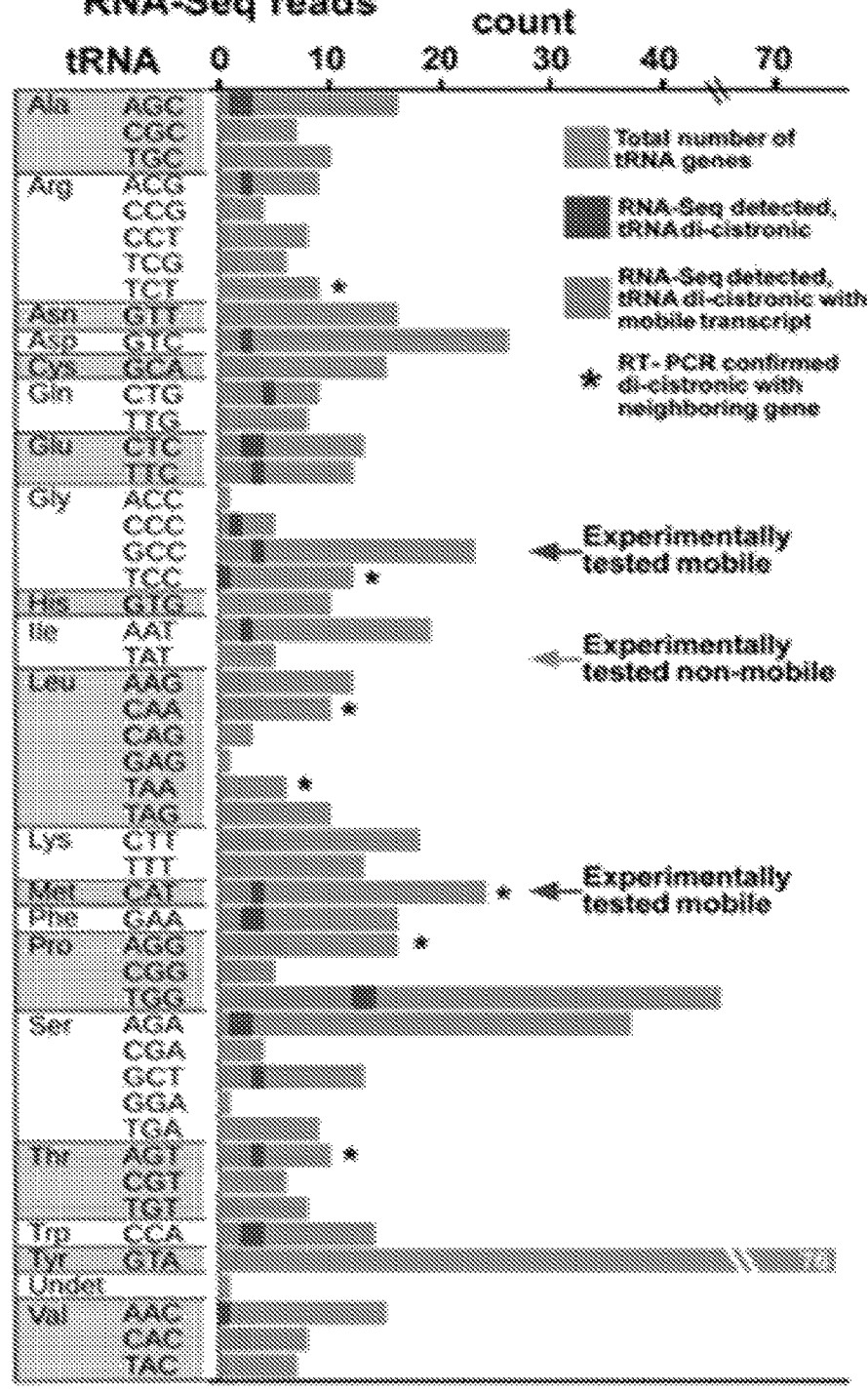

In order to elucidate whether tRNA sequences or related TLS motifs confer mRNA mobility, it was evaluated whether the endogenous mobile mRNA population found in *A. thaliana* is enriched in tRNA sequences related to viral TLS. For this purpose, the *A. thaliana* graft-mobile transcriptome database (n=3606) (Thieme et al., 2015) was screened for presence of TLS motifs in the mRNA UTRs and coding sequences (CDS) (FIG. 7A). Scans were performed for sequence-independent structure motifs using a provided consensus tRNA descriptor (Macke et al., 2001) which recognises tRNA stem-loop arrangements (FIGS. 8A-8C). The analysis revealed that a significant number of mobile transcripts found in *A. thaliana* (11.4%; n=411 of 3606) or grapevine (*Vitis vinifera*) (7.5%; n=249 of 3333) harbour a TLS motif that is found enriched in the CDS and 3'UTR (FIG. 7A). Furthermore, annotated tRNA genes were over-represented in close proximity of genes encoding mobile transcripts. Independent of DNA-strand assignment, 158 of 1,125 genes flanked by a tRNA gene produced mobile RNAs, and of these 158 cases, 113 are located within 1,000 bp distance intervals (FIG. 7B).

Example 3 tRNA-Like-Structure-Mediated mRNA Mobility is Important for Normal Development and Function Introduction To confirm the findings from Examples 1 and 2, and to substantiate the notion that TLSs play a role in transcript mobility of endogenous genes, insertion mutants of the CHOLINE KINASE 1 (CK1; TAIR #AT1G71697) gene, producing a graft mobile transcript (Thieme et al., 2015), which is in close proximity of a tRNA$^{Gly}$ locus and which produces a bicistronic transcript according to the paired end sequencing data were analysed.

Methods

Grafting

The detailed procedure of *Arabidopsis* inflorescence stem grafting used for CK1 mobility assays was performed as described (Nisar et al., 2012) and samples were harvested for RNA extraction and RT-PCR detection one week after grafting.

Quantitative RT-PCR

Quantitative Real-time PCR was performed according to the SYBR Green method in a 5 μl volume using 4 μg total RNA, 2.5 μl SYBR Green Master Mix (Applied Biosystems), 0.2 μM forward and reverse primers. For each genomic confirmed ck1 mutant RNA from 3-5 individual plants was isolated and used. At least three technical replicas were performed. An ABI System Sequence Detector (Applied Biosystems 7900HT fast Real time PCR) was used with the following regiment of thermal cycling: Stage 1: 1 cycle, 2 minutes at 50° C.; Stage 2: 1 cycle, 10 minutes at 95° C.; Stage 3: 40 cycles, 15 seconds at 95° C., 1 minute 60° C. Dissociation stage: 15 seconds at 95° C., 15 seconds at 60° C., 15 seconds at 95° C. Oligonucleotides used for RT-PCR are listed in Table 2.

Results

Figure 7D:
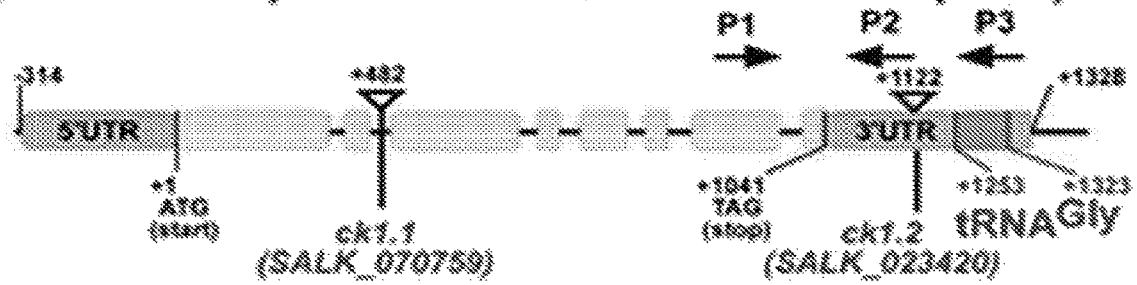

CK1 catalyses the reaction of choline to phosphatidylcholine (and the CK1 transcript is bicistronic, harbouring a tRNA$^{Gly}$ (TAIR #AT1G71700) sequence in the 3'UTR region (CK1::tRNA$^{Gly}$). To test whether CK1 mRNA mobility depends on tRNA$^{Gly}$ presence in the 3'UTR, two SALK T-DNA insertion lines for grafting experiments: ck1.1 (SALK_070759) and ck1.2 (SALK_023420) were first confirmed and then used (FIG. 7D). In ck1.1 mutants the T-DNA is located within the first intron, while ck1.2 mutants have a T-DNA insertion between the stop codon of the CK1 gene and the annotated tRNA$^{Gly}$ sequence, causing the coding sequence of CK1 and the tRNA$^{Gly}$ sequence to be spaced far apart from each other.

Figure 7E:
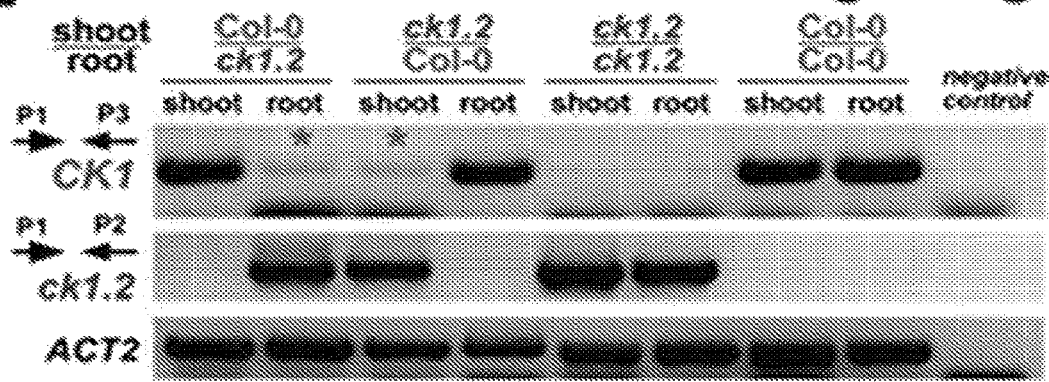

*Arabidopsis* stem grafting experiments were performed with ck1.2 and wild type (Col-0) and assayed for the presence of wild-type CK1:tRNA$^{Gly}$ and truncated ck1.2 mRNA in stock and scion samples via RT-PCR (FIG. 7E).

Although ck1.2 mutants produce a full-length CK1 poly (A) transcript containing all protein-coding sequences, the truncated transcript lacking the tRNA$^{Gly}$ sequence could not be detected in wild-type samples. In contrast, wild-type CK1:tRNA$^{Gly}$ transcript was present in both ck1.2 scion and ck1.2 stock tissue samples. This suggests that the CK1::tRNA$^{Gly}$ transcript was bi-directionally mobile from stock to scion (FIG. 7E), whereas the mutant ck1.2 transcript lacking the tRNA$^{Gly}$ sequence was not transported over graft junctions. Thus, the graft-mobility of the endogenously produced bicistronic CK1:tRNA$^{Gly}$ transcript depends on the presence of the 3'UTR tRNA$^{Gly}$ sequence.

Figure 7F:
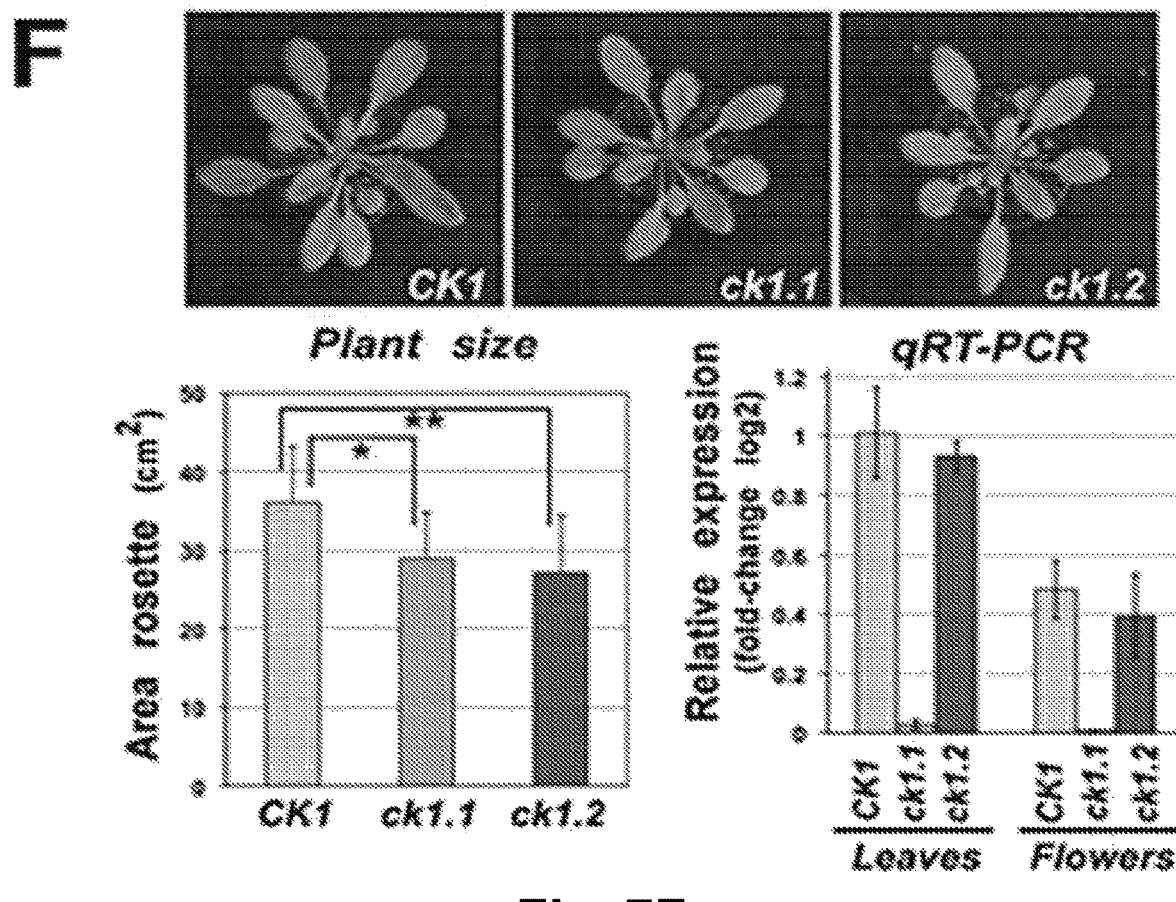
Figure 7G:
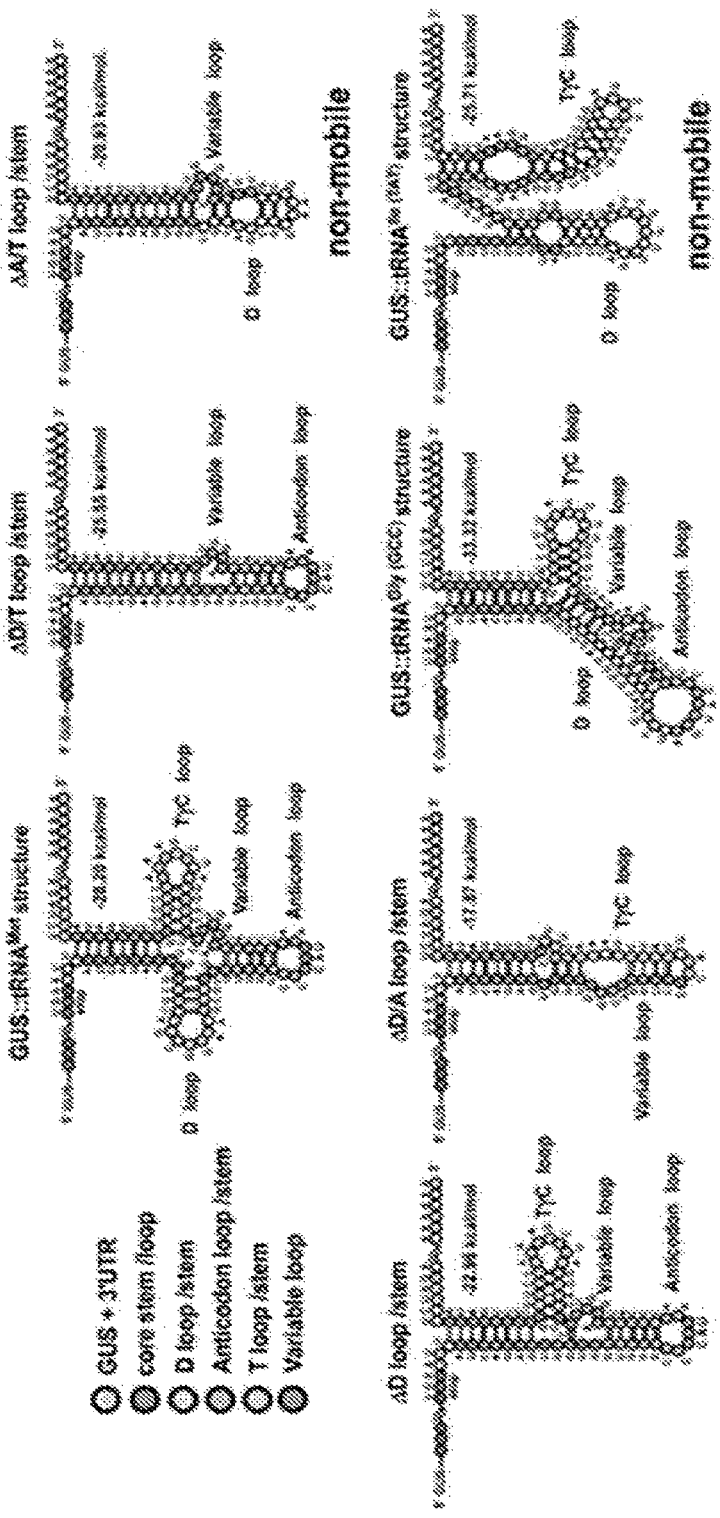

As lack of detectable ck1.2 transcript mobility could be a result of low expression levels, quantitative RT-PCR assays were performed to evaluate CK1 expression levels in the two ck1.1 and ck.2 mutants and in wild-type plants. Here, only minimal expression could be detected in the ck1.1 mutant, whereas CK1 transcript levels in the ck1.2 mutant were similar to that found in the wild type (FIG. 7F). Despite the fact that similar levels of CK1 poly(A)-RNA transcript were produced by wild-type and ck1.2 mutant plants, both the ck1.2 line and the ck1.1 line showed a significant decrease in rosette leaf size compared to wild type (FIG. 7F). This implies that not only CK1 mRNA presence in the expressing cells is required for normal growth behaviour of *Arabidopsis*, but also the mobility of the CK1 mRNA throughout the plant.

CITED REFERENCES

Alonso, J. M., Stepanova, A. N., Leisse, T. J., Kim, C. J., Chen, H., Shinn, P., Stevenson, D. K., Zimmerman, J., Barajas, P., Cheuk, R., Gadrinab, C., Heller, C., Jeske, A., Koesema, E., Meyers, C. C., Parker, H., Prednis, L., Ansari, Y., Choy, N., Deen, H., Geralt, M., Hazari, N., Horn, E., Karnes, M., Mulholland, C., Ndubaku, R., Schmidt, I., Guzman, P., Aguilar-Henonin, L., Schmid, M., Weigel, D., Carter, D. E., Marchand, T., Risseeuw, E., Brogden, D., Zeko, A., Crosby, W. L., Berry, C. C., and Ecker, J. R. (2003). Genome-wide insertional mutagenesis of *Arabidopsis thaliana*. Science 301, 653-657.

Cho, S. K., Sharma, P., Butler, N. M., Kang, I. H., Shah, S., Rao, A. G., and Hannapel, (2015). Polypyrimidine tract-binding proteins of potato mediate tuberization through an interaction with StBEL5 RNA. J Exp Bot 66, 6835-6847.

Curtis, M. D., and Grossniklaus, U. (2003). A gateway cloning vector set for high-throughput functional analysis of genes in planta. Plant Physiol 133, 462-469.

Juhling, F., Morl, M., Hartmann, R. K., Sprinzl, M., Stadler, P. F., and Putz, J. (2009). tRNAdb 2009: compilation of tRNA sequences and tRNA genes. Nucleic Acids Res 37, D159-162.

Lamesch, P., Berardini, T. Z., Li, D., Swarbreck, D., Wilks, C., Sasidharan, R., Muller, R., Dreher, K., Alexander, D. L., Garcia-Hernandez, M., Karthikeyan, A. S., Lee, C. H., Nelson, W. D., Ploetz, L., Singh, S., Wensel, A., and Huala, E. (2012). The *Arabidopsis* Information Resource (TAIR): improved gene annotation and new tools. Nucleic Acids Res 40, D1202-1210.

Lohse, M., Bolger, A. M., Nagel, A., Fernie, A. R., Lunn, J. E., Stitt, M., and Usadel, B. (2012). RobiNA: a user-friendly, integrated software solution for RNA-Seq-based transcriptomics. Nucleic Acids Res 40, W622-627.

Macke, T. J., Ecker, D. J., Gutell, R. R., Gautheret, D., Case, D. A., and Sampath, R. (2001). RNAMotif, an RNA secondary structure definition and search algorithm. Nucleic acids research 29, 4724-4735.

Nisar, N., Verma, S., Pogson, B. J., and Cazzonelli, C. I. (2012). Inflorescence stem grafting made easy in *Arabidopsis*. Plant Methods 8, 50.

Thieme, C. J., Rojas-Triana, M., Stecyk, E., Schudoma, C., Zhang, W., Yang, L., Miambres, M., Walther, D., Schulze, W. X., Paz-Ares, J., Scheible, W.-R. D., and Kragler, F. (2015). Endogenous *Arabidopsis* messenger RNAs transported to distant tissues. Nature Plants 1, 15025.

Zhang, S., Sun, L., and Kragler, F. (2009). The phloem-delivered RNA pool contains small noncoding RNAs and interferes with translation. Plant Physiology 150, 378-387.

Zhang, W., Kollwig, G., Stecyk, E., Apelt, F., Dirks, R., and Kragler, F. (2014). Graft-transmissible movement of inverted-repeat-induced siRNA signals into flowers. The Plant journal 80, 106-121.

The invention claimed is:

1. A method for changing the intercellular mobility of an mRNA of a gene in a plant, comprising including the sequence of a tRNA-like structure in the transcribed part of the gene to confer movement to the gene, wherein the gene encodes an RNA-guided endonuclease, wherein the tRNA-like structure is selected from the group consisting of tRNA$^{Ala}$, tRNA$^{Arg}$, tRNA$^{Asn}$, tRNA$^{Asp}$, tRNA$^{Cys}$, tRNA$^{Gln}$, tRNA$^{Glu}$, tRNA$^{Gly}$, tRNA$^{His}$, tRNA$^{Ile}$ excluding tRNA$^{Ile}$ with anticodon UAU, tRNA$^{Leu}$, tRNA$^{Lys}$, tRNA$^{Met}$, tRNA$^{Phe}$, tRNA$^{Pro}$, tRNA$^{Ser}$, tRNA$^{Thr}$, tRNA$^{Trp}$, tRNA$^{Tyr}$, and tRNA$^{Val}$, or wherein the tRNA-like structure is one of the aforementioned tRNA structures lacking the D stem-loop, the D and T stem-loops, or the D and A stem-loops.

2. The method of claim 1, wherein the RNA-guided endonuclease is derived from a Cas protein.

3. The method of claim 2, wherein the Cas protein is Cas9 or a variant thereof, or Cpf1.

4. The method of claim 1, wherein the RNA-guided endonuclease protein further comprises at least one localisation signal to a DNA-containing organelle, selected from the group consisting of a nuclear localisation signal, a chloroplast targeting signal and a mitochondrial targeting signal.

5. The method of claim 1, wherein the RNA-guided endonuclease protein further comprises a marker domain, selected from a fluorescent marker and an epitope tag.

6. The method of claim 1, wherein the tRNA-like structure is located in the 5'UTR of the RNA-guided endonuclease-encoding mRNA.

7. The method of claim 1, wherein the tRNA-like structure is located in the coding sequence of the RNA-guided endonuclease-encoding mRNA.

8. The method of claim 1, wherein the tRNA-like structure is located in the 3'UTR of the RNA-guided endonuclease-encoding mRNA.

9. A method for modifying a chromosomal sequence in a plant cell or spore, comprising:
   a) combining a first plant comprising a rootstock, which harbors a nucleotide sequence encoding a modified, non-naturally occurring RNA-guided endonuclease protein, with a scion from a second plant grafted onto the rootstock of the said first plant, whereby the nucleotide sequence generates a transcript in the rootstock of the first plant, which transcript is transported systemically across the graft junction to enter the scion of the second plant, and which transcript is imported into cells of the scion of the second plant, where it is translated into a functional protein;
   b) providing at least one guide RNA or DNA encoding at least one guide RNA to at least one cell or spore of the scion of the second plant, wherein the at least one guide RNA is a single molecule comprising a 5' region that is complementary to a target site in a chromosomal sequence of said second plant; and
   c) allowing each guide RNA to direct the RNA-guided endonuclease protein to a targeted site in the chromosomal sequence, where the RNA-guided endonuclease protein introduces a double-stranded break in the targeted site, and allowing the cell to repair the double-stranded break by a DNA-repair process such that the chromosomal sequence is modified in at least one cell or spore of the scion of the second plant,
   wherein a tRNA-like structure is included in the transcribed part of the nucleotide sequence, which encodes the RNA-guided endonuclease and wherein the tRNA-like structure is selected from the group consisting of tRNA$^{Ala}$, tRNA$^{Arg}$, tRNA$^{Asn}$, tRNA$^{Asp}$, tRNA$^{Cys}$, tRNA$^{Gln}$, tRNA$^{Glu}$, tRNA$^{Gly}$, tRNA$^{His}$, tRNA$^{Ile}$ excluding tRNA$^{Ile}$ with anticodon UAU, tRNA$^{Leu}$, tRNA$^{Lys}$, tRNA$^{Met}$, tRNA$^{Phe}$, tRNA$^{Pro}$, tRNA$^{Ser}$, tRNA$^{Thr}$, tRNA$^{Trp}$, tRNA$^{Tyr}$, and tRNA$^{Val}$, or wherein the tRNA-like structure is one of the aforementioned tRNA structures lacking the D stem-loop, the D and T stem-loops, or the D and A stem-loops.

10. The method of claim 9, wherein the nucleotide sequence encoding the modified, non-naturally occurring RNA-guided endonuclease protein in the first plant is operably linked to a promoter sequence that confers a ubiquitous expression profile or a tissue- or cell-type specific expression profile onto the transgenic nucleic acid sequence.

11. The method of claim 10, wherein the promoter sequence confers onto the nucleotide sequence an expression profile that encompasses roots.

12. The method of claim 9, wherein expression of the nucleotide sequence in the first plant is transient, and wherein transient expression is in particular achieved by use of an inducible promoter, selected from the group comprising heat-inducible promoters, cold-inducible promoters, chemical-inducible promoters, steroid-inducible promoters and alcohol-inducible promoters.

13. The method of claim 9, wherein said first plant and said second plant belong to the same plant family, to the same genus, or to the same plant species.

14. The method of claim 13, wherein said first plant and said second plant belong to the genus *Allium, Apium, Beta, Brassica, Capsicum, Cichorium, Citrullus, Cucumis, Cucurbita, Benincasa, Daucus, Eruca, Lactuca, Lagenaria, Luffa, Phaseolus, Pisum, Raphanus, Solanum, Spinacia, Valerianella, Nicotiana, Petunia, Arabidopsis, Capsella, Arabis, Malus, Pyrus, Prunus, Vitis, Rosa, Fragaria, Populus, Fagus, Pinus, Picea, Ginkgo, Larix, Betula, Quercus, Salix, Alnus, Corylus, Amygdalus, Vaccinium, Rubus, Persea, Citrus, Castanea, Acer, Fraxinus, Coffea, Camellia, Theobroma, Olea, Cicer, Juglans, Pistacia, Arachis, Anacardium, Macadamia, Ficus, Litchi, Actinidia, Bougainvillea, Helianthus, Hibiscus, Malva, Glycine, Gossypium, Cannabis, Stevia, Opuntia,* or *Ipomoea.*

15. The method of claim 9, wherein modifying the chromosomal sequence of the cell or spore is done without the insertion of external genetic material into the chromosomal sequence.

16. The method of claim 9, wherein the RNA-guided endonuclease protein further comprises at least one localisation signal to a DNA-containing organelle, selected from the group consisting of a nuclear localisation signal, a chloroplast targeting signal and a mitochondrial targeting signal.

17. The method of claim 9, wherein the RNA-guided endonuclease protein further comprises a marker domain, selected from a fluorescent marker and an epitope tag.

18. The method of claim 9, wherein the tRNA-like structure is located in the 5'UTR of the RNA-guided endonuclease-encoding mRNA.

19. The method of claim 9, wherein the tRNA-like structure is located in the coding sequence of the RNA-guided endonuclease-encoding mRNA.

20. The method of claim 9, wherein the tRNA-like structure is located in the 3'UTR of the RNA-guided endonuclease-encoding mRNA.

21. The method of claim 9, wherein the RNA-guided endonuclease is derived from a Cas protein, in particular Cas9 or a variant thereof, or Cpf1.

22. A method for modifying a chromosomal sequence in a plant cell or spore, comprising:
  a) providing an mRNA transcript encoding an RNA-guided endonuclease and comprising a tRNA-like structure to a plant, a plant cell or a plant spore by (micro)injection, transfection, electroporation, lipofection, nanoparticle-mediated transfection, PEG-mediated transfection, or infection with a suitable virus or a suitable bacterium;
  b) providing at least one guide RNA or DNA encoding at least one guide RNA to said plant, plant cell or plant spore by means of injection, *Agrobacterium*-mediated transformation, exogenous application, or by means of stable integration or transient expression of a DNA-construct, wherein the at least one guide RNA is a single molecule comprising a 5' region that is complementary to a target site in a chromosomal sequence of said plant; and
  c) allowing each guide RNA to direct the RNA-guided endonuclease protein to a targeted site in the chromosomal sequence, where the RNA-guided endonuclease protein introduces a double-stranded break in the targeted site, and allowing the cell to repair the double-stranded break by a DNA-repair process such that the chromosomal sequence is modified in at least one cell or spore of the plant, wherein the tRNA-like structure is selected from the group consisting of tRNA$^{Ala}$, tRNA$^{Arg}$, tRNA$^{Asn}$, tRNA$^{Asp}$, tRNA$^{Cys}$, tRNA$^{Gln}$, tRNA$^{Glu}$, tRNA$^{Gly}$, tRNA$^{His}$, tRNA$^{Ile}$ excluding tRNA$^{Ile}$ with anticodon UAU, tRNA$^{Leu}$, tRNA$^{Lys}$, tRNA$^{Met}$, tRNA$^{Pho}$, tRNA$^{Pro}$, tRNA$^{Ser}$, tRNA$^{Thr}$, tRNA$^{Trp}$, tRNA$^{Tyr}$, and tRNA$^{Val}$, or wherein the tRNA-like structure is one of the aforementioned tRNA structures lacking the D stem-loop, the D and T stem-loops, or the D and A stem-loops.

23. The method of claim 22, wherein the plant belongs to the genus *Allium, Apium, Beta, Brassica, Capsicum, Cichorium, Citrullus, Cucumis, Cucurbita, Benincasa, Daucus, Eruca, Lactuca, Lagenaria, Luffa, Phaseolus, Pisum, Lens, Raphanus, Solanum, Spinacia, Valerianella, Nicotiana, Petunia, Arabidopsis, Capsella, Arabis, Cardamine, Malus, Pyrus, Prunus, Vitis, Rosa, Fragaria, Populus, Fagus, Pinus, Picea, Ginkgo, Larix, Betula, Quercus, Salix, Alnus, Corylus, Amygdalus, Vaccinium, Rubus, Persea, Citrus, Castanea, Acer, Fraxinus, Coffea, Camellia, Theobroma, Olea, Cicer, Juglans, Pistacia, Arachis, Anacardium, Macadamia, Ficus, Litchi, Actinidia, Bougainvillea, Helianthus, Hibiscus, Malva, Glycine, Gossypium, Cannabis, Stevia, Opuntia, Ipomoea, Manihot, Humulus, Acacia, Medicago, Trifolium, Lotus, Vicia, Linum, Fagopyrum, Zea, Triticum, Avena, Hordeum, Oryza, Zizania, Secale, Triticosecale, Sorghum, Bambusa, Dendrocalamus, Saccharum, Cymbopogon, Pennisetum, Panicum, Festuca, Lolium, Phleum, Poa, Miscanthus, Asparagus, Agave, Yucca, Cocos, Elaeis, Phoenix, Amaryllis, Narcissus, Aloe, Canna, Iris, Colchicum, Crocus, Gladiolus, Juncus, Lilium, Tulipa, Musa, Dendrobium, Phalaenopsis, Vanilla, Typha, Zingiber, Curcuma,* or *Lemna.*

24. The method of claim 22, wherein modifying the chromosomal sequence of the cell or spore is done without the insertion of external genetic material into the chromosomal sequence.

25. The method of claim 22, wherein the RNA-guided endonuclease protein further comprises at least one localisation signal to a DNA-containing organelle, selected from the group consisting of a nuclear localisation signal, a chloroplast targeting signal and a mitochondrial targeting signal.

26. The method of claim 22, wherein the RNA-guided endonuclease protein further comprises a marker domain, selected from a fluorescent marker and an epitope tag.

27. The method of claim 22, wherein the tRNA-like structure is located in the 5'UTR of the RNA-guided endonuclease-encoding mRNA.

28. The method of claim 22, wherein the tRNA-like structure is located in the coding sequence of the RNA-guided endonuclease-encoding mRNA.

29. The method of claim 22, wherein the tRNA-like structure is located in the 3'UTR of the RNA-guided endonuclease-encoding mRNA.

30. The method of claim 22, wherein the RNA-guided endonuclease protein further comprises at least one localisation signal to a DNA-containing organelle, selected from the group consisting of a nuclear localisation signal, a chloroplast targeting signal and a mitochondrial targeting signal.

31. The method of claim 22, wherein the RNA-guided endonuclease is derived from a Cas protein, in particular Cas9 or a variant thereof, or Cpf1.

* * * * *

SEQUENCE LISTING

```
<160> NUMBER OF SEQ ID NOS: 117

<210> SEQ ID NO 1
<211> LENGTH: 20
<212> TYPE: DNA
<213> ORGANISM: Nicotiana tabacum
<220> FEATURE:
<223> OTHER INFORMATION: Table 2: FK868-F

<400> SEQUENCE: 1
gatgctccga atctcgctga                                        20

<210> SEQ ID NO 2
<211> LENGTH: 20
<212> TYPE: DNA
<213> ORGANISM: Nicotiana tabacum
<220> FEATURE:
<223> OTHER INFORMATION: Table 2: FK869-R

<400> SEQUENCE: 2
gttgcttgct gctggtgaag                                        20

<210> SEQ ID NO 3
<211> LENGTH: 20
<212> TYPE: DNA
<213> ORGANISM: Nicotiana tabacum
<220> FEATURE:
<223> OTHER INFORMATION: Table 2: FK868-F

<400> SEQUENCE: 3
gatgctccga atctcgctga                                        20

<210> SEQ ID NO 4
<211> LENGTH: 21
<212> TYPE: DNA
<213> ORGANISM: Nicotiana tabacum
<220> FEATURE:
<223> OTHER INFORMATION: Table 2: FK851-R

<400> SEQUENCE: 4
ttccgctgcg ccactctgat t                                      21

<210> SEQ ID NO 5
<211> LENGTH: 20
<212> TYPE: DNA
<213> ORGANISM: Nicotiana tabacum
<220> FEATURE:
<223> OTHER INFORMATION: Table 2: FK868-F

<400> SEQUENCE: 5
gatgctccga atctcgctga                                        20
```

<210> SEQ ID NO 6
<211> LENGTH: 21
<212> TYPE: DNA
<213> ORGANISM: Nicotiana tabacum
<220> FEATURE:
<223> OTHER INFORMATION: Table 2: FK851-R

<400> SEQUENCE: 6
ttccgctgcg ccactctgat t                                      21

<210> SEQ ID NO 7
<211> LENGTH: 20
<212> TYPE: DNA
<213> ORGANISM: Nicotiana tabacum
<220> FEATURE:
<223> OTHER INFORMATION: Table 2: FK868-F

<400> SEQUENCE: 7
gatgctccga atctcgctga                                        20

<210> SEQ ID NO 8
<211> LENGTH: 18
<212> TYPE: DNA
<213> ORGANISM: Nicotiana tabacum
<220> FEATURE:
<223> OTHER INFORMATION: Table 2: FK779-R

<400> SEQUENCE: 8
tagaaggcat tggtggtg                                          18

<210> SEQ ID NO 9
<211> LENGTH: 18
<212> TYPE: DNA
<213> ORGANISM: Nicotiana tabacum
<220> FEATURE:
<223> OTHER INFORMATION: Table 2: FK774-F

<400> SEQUENCE: 9
ataacccaca ggtcccag                                          18

<210> SEQ ID NO 10
<211> LENGTH: 18
<212> TYPE: DNA
<213> ORGANISM: Nicotiana tabacum
<220> FEATURE:
<223> OTHER INFORMATION: Table 2: FK771-R

<400> SEQUENCE: 10
ttccattccc tcctttca                                          18

<210> SEQ ID NO 11
<211> LENGTH: 20
<212> TYPE: DNA
<213> ORGANISM: Nicotiana tabacum
<220> FEATURE:
<223> OTHER INFORMATION: Table 2: FK938-F

<400> SEQUENCE: 11
cccgacaacc actacctgag                                        20

<210> SEQ ID NO 12
<211> LENGTH: 23
<212> TYPE: DNA
<213> ORGANISM: Nicotiana tabacum
<220> FEATURE:

<223> OTHER INFORMATION: Table 2: FK858-R

<400> SEQUENCE: 12
tcatcgagag cttgacaccc tgt                                      23

<210> SEQ ID NO 13
<211> LENGTH: 21
<212> TYPE: DNA
<213> ORGANISM: Nicotiana tabacum
<220> FEATURE:
<223> OTHER INFORMATION: Table 2: FK422-F

<400> SEQUENCE: 13
caccggtatt gtgttggact c                                        21

<210> SEQ ID NO 14
<211> LENGTH: 23
<212> TYPE: DNA
<213> ORGANISM: Nicotiana tabacum
<220> FEATURE:
<223> OTHER INFORMATION: Table 2: FK423-R

<400> SEQUENCE: 14
aggacctcag gacaacggaa acg                                      23

<210> SEQ ID NO 15
<211> LENGTH: 20
<212> TYPE: DNA
<213> ORGANISM: Nicotiana tabacum
<220> FEATURE:
<223> OTHER INFORMATION: Table 2: FK424-F

<400> SEQUENCE: 15
ggaaggatct gtacggtaac                                          20

<210> SEQ ID NO 16
<211> LENGTH: 20
<212> TYPE: DNA
<213> ORGANISM: Nicotiana tabacum
<220> FEATURE:
<223> OTHER INFORMATION: Table 2: FK425-R

<400> SEQUENCE: 16
tgtgaacgat tcctggacct                                          20

<210> SEQ ID NO 17
<211> LENGTH: 19
<212> TYPE: DNA
<213> ORGANISM: Nicotiana tabacum
<220> FEATURE:
<223> OTHER INFORMATION: Table 2: FK907-F

<400> SEQUENCE: 17
attttgccga tttcggaac                                           19

<210> SEQ ID NO 18
<211> LENGTH: 21
<212> TYPE: DNA
<213> ORGANISM: Nicotiana tabacum
<220> FEATURE:
<223> OTHER INFORMATION: Table 2: FK908-R

<400> SEQUENCE: 18
tggttcatta caggagaacc g                                        21

```
<210> SEQ ID NO 19
<211> LENGTH: 21
<212> TYPE: DNA
<213> ORGANISM: Nicotiana tabacum
<220> FEATURE:
<223> OTHER INFORMATION: Table 2: FK909-F

<400> SEQUENCE: 19
tttgtgaatc tcagggaatg c                                           21

<210> SEQ ID NO 20
<211> LENGTH: 21
<212> TYPE: DNA
<213> ORGANISM: Nicotiana tabacum
<220> FEATURE:
<223> OTHER INFORMATION: Table 2: FK914-R

<400> SEQUENCE: 20
agcagccatc tcacaaaagt g                                           21

<210> SEQ ID NO 21
<211> LENGTH: 21
<212> TYPE: DNA
<213> ORGANISM: Nicotiana tabacum
<220> FEATURE:
<223> OTHER INFORMATION: Table 2: FK915-R

<400> SEQUENCE: 21
tctaaaacgc gttttgcaaa c                                           21

<210> SEQ ID NO 22
<211> LENGTH: 20
<212> TYPE: DNA
<213> ORGANISM: Nicotiana tabacum
<220> FEATURE:
<223> OTHER INFORMATION: Table 2: FK883-F

<400> SEQUENCE: 22
ctatggggaa tcatctcggg                                             20

<210> SEQ ID NO 23
<211> LENGTH: 20
<212> TYPE: DNA
<213> ORGANISM: Nicotiana tabacum
<220> FEATURE:
<223> OTHER INFORMATION: Table 2: FK884-R

<400> SEQUENCE: 23
cactagacca ctggtgcttc                                             20

<210> SEQ ID NO 24
<211> LENGTH: 20
<212> TYPE: DNA
<213> ORGANISM: Nicotiana tabacum
<220> FEATURE:
<223> OTHER INFORMATION: Table 2: FK883-F

<400> SEQUENCE: 24
ctatggggaa tcatctcggg                                             20

<210> SEQ ID NO 25
<211> LENGTH: 20
<212> TYPE: DNA
<213> ORGANISM: Nicotiana tabacum
<220> FEATURE:
<223> OTHER INFORMATION: Table 2: FK992-R
```

<400> SEQUENCE: 25
ccgtggcagg gtactatcat                                          20

<210> SEQ ID NO 26
<211> LENGTH: 20
<212> TYPE: DNA
<213> ORGANISM: Nicotiana tabacum
<220> FEATURE:
<223> OTHER INFORMATION: Table 2: FK883-F

<400> SEQUENCE: 26
ctatggggaa tcatctcggg                                          20

<210> SEQ ID NO 27
<211> LENGTH: 25
<212> TYPE: DNA
<213> ORGANISM: Nicotiana tabacum
<220> FEATURE:
<223> OTHER INFORMATION: Table 2: FK962-R

<400> SEQUENCE: 27
gtagactata tattgtggtg taaac                                    25

<210> SEQ ID NO 28
<211> LENGTH: 21
<212> TYPE: DNA
<213> ORGANISM: Nicotiana tabacum
<220> FEATURE:
<223> OTHER INFORMATION: Table 2: FK963-F

<400> SEQUENCE: 28
ctagccatgg tagatctgag g                                        21

<210> SEQ ID NO 29
<211> LENGTH: 106
<212> TYPE: DNA
<213> ORGANISM: Nicotiana tabacum
<220> FEATURE:
<223> OTHER INFORMATION: Table 2: FK944-R

<400> SEQUENCE: 29
gcgcggtgac ctgcaccagc cgggaattga acccgggtct gtaccgtggc agggtactat    60
catgccacta gaccactggt gcaattcaca cgtgatggtg atggtg                  106

<210> SEQ ID NO 30
<211> LENGTH: 106
<212> TYPE: DNA
<213> ORGANISM: Nicotiana tabacum
<220> FEATURE:
<223> OTHER INFORMATION: Table 2: FK945-R

<400> SEQUENCE: 30
gcgcggtgac ctatcagagc caccttcgat cctgggacct gtgggttatg ggcccaccac    60
gcttccgctg cgccactctg ataattcaca cgtgatggtg atggtg                  106

<210> SEQ ID NO 31
<211> LENGTH: 108
<212> TYPE: DNA
<213> ORGANISM: Nicotiana tabacum
<220> FEATURE:
<223> OTHER INFORMATION: Table 2: FK946-R

<400> SEQUENCE: 31
gcgcggtgac cgcttccggc ggggctcgaa cccgcgacct tcggctcata agaccaacgc    60

```
tctaaccaac tgagctacgg gagcaattca cacgtgatgg tgatggtg                    108
```

<210> SEQ ID NO 32
<211> LENGTH: 94
<212> TYPE: DNA
<213> ORGANISM: Nicotiana tabacum
<220> FEATURE:
<223> OTHER INFORMATION: Table 2: FK948-R

<400> SEQUENCE: 32

```
gcgcggtgac ctatcagagc caggtttcga tcctgggacc tgtgggttat gggcccacca      60
ccactctgat aattcacacg tgatggtgat ggtg                                  94
```

<210> SEQ ID NO 33
<211> LENGTH: 79
<212> TYPE: DNA
<213> ORGANISM: Nicotiana tabacum
<220> FEATURE:
<223> OTHER INFORMATION: Table 2: FK950-R

<400> SEQUENCE: 33

```
gcgcggtgac ctatcagagc caggtttcga tcctgggacc tgccaccact ctgataattc      60
acacgtgatg gtgatggtg                                                   79
```

<210> SEQ ID NO 34
<211> LENGTH: 79
<212> TYPE: DNA
<213> ORGANISM: Nicotiana tabacum
<220> FEATURE:
<223> OTHER INFORMATION: Table 2: FK949-R

<400> SEQUENCE: 34

```
gcgcggtgac ctatcagagc ggacctgtgg gttatgggcc caccaccact ctgacaattc      60
acacgtgatg gtgatggtg                                                   79
```

<210> SEQ ID NO 35
<211> LENGTH: 77
<212> TYPE: DNA
<213> ORGANISM: Nicotiana tabacum
<220> FEATURE:
<223> OTHER INFORMATION: Table 2: FK947-R

<400> SEQUENCE: 35

```
gcgcggtgac ctatcagagc ggacctgcca cgcttccgct gcgccactct gataattcac      60
acgtgatggt gatggtg                                                     77
```

<210> SEQ ID NO 36
<211> LENGTH: 26
<212> TYPE: DNA
<213> ORGANISM: Nicotiana tabacum
<220> FEATURE:
<223> OTHER INFORMATION: Table 2: FK951-R

<400> SEQUENCE: 36

```
gcgcggtgac ctctagatat cagagc                                           26
```

<210> SEQ ID NO 37
<211> LENGTH: 23
<212> TYPE: DNA
<213> ORGANISM: Nicotiana tabacum
<220> FEATURE:
<223> OTHER INFORMATION: Table 2: FK952-R

<400> SEQUENCE: 37
gcgcggtgac ctctagatgc acc					23

<210> SEQ ID NO 38
<211> LENGTH: 25
<212> TYPE: DNA
<213> ORGANISM: Nicotiana tabacum
<220> FEATURE:
<223> OTHER INFORMATION: Table 2: FK953-R

<400> SEQUENCE: 38
gcgcggtgac ctctagagct tccgg					25

<210> SEQ ID NO 39
<211> LENGTH: 20
<212> TYPE: DNA
<213> ORGANISM: Nicotiana tabacum
<220> FEATURE:
<223> OTHER INFORMATION: Table 2: FK1091-F

<400> SEQUENCE: 39
caacagcttc cggaccgcac					20

<210> SEQ ID NO 40
<211> LENGTH: 20
<212> TYPE: DNA
<213> ORGANISM: Nicotiana tabacum
<220> FEATURE:
<223> OTHER INFORMATION: Table 2: FK1092-R

<400> SEQUENCE: 40
gattgagcgc gatgacgtca					20

<210> SEQ ID NO 41
<211> LENGTH: 20
<212> TYPE: DNA
<213> ORGANISM: Nicotiana tabacum
<220> FEATURE:
<223> OTHER INFORMATION: Table 2: FK1079-F

<400> SEQUENCE: 41
cgagtactac caggcgaacc					20

<210> SEQ ID NO 42
<211> LENGTH: 21
<212> TYPE: DNA
<213> ORGANISM: Nicotiana tabacum
<220> FEATURE:
<223> OTHER INFORMATION: Table 2: FK1079-F

<400> SEQUENCE: 42
cagagccagg tttcgatcct g					21

<210> SEQ ID NO 43
<211> LENGTH: 20
<212> TYPE: DNA
<213> ORGANISM: Nicotiana tabacum
<220> FEATURE:
<223> OTHER INFORMATION: Table 2: FK1079-F

<400> SEQUENCE: 43
cgagtactac caggcgaacc					20

<210> SEQ ID NO 44
<211> LENGTH: 20

```
<212> TYPE: DNA
<213> ORGANISM: Nicotiana tabacum
<220> FEATURE:
<223> OTHER INFORMATION: Table 2: FK1086-R

<400> SEQUENCE: 44
gcagggtact atcatgccac                                                 20

<210> SEQ ID NO 45
<211> LENGTH: 20
<212> TYPE: DNA
<213> ORGANISM: Nicotiana tabacum
<220> FEATURE:
<223> OTHER INFORMATION: Table 2: FK1080-F

<400> SEQUENCE: 45
accacgtcgt gttcgatgag                                                 20

<210> SEQ ID NO 46
<211> LENGTH: 20
<212> TYPE: DNA
<213> ORGANISM: Nicotiana tabacum
<220> FEATURE:
<223> OTHER INFORMATION: Table 2: FK1085-R

<400> SEQUENCE: 46
ggctcataag accaacgctc                                                 20

<210> SEQ ID NO 47
<211> LENGTH: 20
<212> TYPE: DNA
<213> ORGANISM: Nicotiana tabacum
<220> FEATURE:
<223> OTHER INFORMATION: Table 2: FK1079-F

<400> SEQUENCE: 47
cgagtactac caggcgaacc                                                 20

<210> SEQ ID NO 48
<211> LENGTH: 21
<212> TYPE: DNA
<213> ORGANISM: Nicotiana tabacum
<220> FEATURE:
<223> OTHER INFORMATION: Table 2: FK1081-R

<400> SEQUENCE: 48
cagagccagg tttcgatcct g                                               21

<210> SEQ ID NO 49
<211> LENGTH: 20
<212> TYPE: DNA
<213> ORGANISM: Nicotiana tabacum
<220> FEATURE:
<223> OTHER INFORMATION: Table 2: FK1080-F

<400> SEQUENCE: 49
accacgtcgt gttcgatgag                                                 20

<210> SEQ ID NO 50
<211> LENGTH: 21
<212> TYPE: DNA
<213> ORGANISM: Nicotiana tabacum
<220> FEATURE:
<223> OTHER INFORMATION: Table 2: FK1083-R

<400> SEQUENCE: 50
```

| | |
|---|---|
| gttatgggcc caccaccact c | 21 |

<210> SEQ ID NO 51
<211> LENGTH: 20
<212> TYPE: DNA
<213> ORGANISM: Nicotiana tabacum
<220> FEATURE:
<223> OTHER INFORMATION: Table 2: FK1079-F

<400> SEQUENCE: 51

| | |
|---|---|
| cgagtactac caggcgaacc | 20 |

<210> SEQ ID NO 52
<211> LENGTH: 18
<212> TYPE: DNA
<213> ORGANISM: Nicotiana tabacum
<220> FEATURE:
<223> OTHER INFORMATION: Table 2: FK1084-R

<400> SEQUENCE: 52

| | |
|---|---|
| gatcctggga cctgccac | 18 |

<210> SEQ ID NO 53
<211> LENGTH: 20
<212> TYPE: DNA
<213> ORGANISM: Nicotiana tabacum
<220> FEATURE:
<223> OTHER INFORMATION: Table 2: FK1079-F

<400> SEQUENCE: 53

| | |
|---|---|
| cgagtactac caggcgaacc | 20 |

<210> SEQ ID NO 54
<211> LENGTH: 21
<212> TYPE: DNA
<213> ORGANISM: Nicotiana tabacum
<220> FEATURE:
<223> OTHER INFORMATION: Table 2: FK1082-R

<400> SEQUENCE: 54

| | |
|---|---|
| gctgcgccac tctgataatt c | 21 |

<210> SEQ ID NO 55
<211> LENGTH: 21
<212> TYPE: DNA
<213> ORGANISM: Nicotiana tabacum
<220> FEATURE:
<223> OTHER INFORMATION: Table 2: FK1099-F

<400> SEQUENCE: 55

| | |
|---|---|
| agaacgctag ccatcaccat c | 21 |

<210> SEQ ID NO 56
<211> LENGTH: 22
<212> TYPE: DNA
<213> ORGANISM: Nicotiana tabacum
<220> FEATURE:
<223> OTHER INFORMATION: Table 2: FK1100-R

<400> SEQUENCE: 56

| | |
|---|---|
| gccaaatgtt tgaacgatcg gg | 22 |

<210> SEQ ID NO 57
<211> LENGTH: 21
<212> TYPE: DNA
<213> ORGANISM: Nicotiana tabacum

```
<220> FEATURE:
<223> OTHER INFORMATION: Table 2: FK1099-F

<400> SEQUENCE: 57
agaacgctag ccatcaccat c                                           21

<210> SEQ ID NO 58
<211> LENGTH: 19
<212> TYPE: DNA
<213> ORGANISM: Nicotiana tabacum
<220> FEATURE:
<223> OTHER INFORMATION: Table 2: FK1090-R

<400> SEQUENCE: 58
gcaagaccgg caacaggat                                              19

<210> SEQ ID NO 59
<211> LENGTH: 21
<212> TYPE: DNA
<213> ORGANISM: Nicotiana tabacum
<220> FEATURE:
<223> OTHER INFORMATION: Table 2: FK1093-F

<400> SEQUENCE: 59
cgcgtccaag gaaacaagaa g                                           21

<210> SEQ ID NO 60
<211> LENGTH: 23
<212> TYPE: DNA
<213> ORGANISM: Nicotiana tabacum
<220> FEATURE:
<223> OTHER INFORMATION: Table 2: FK1094-F

<400> SEQUENCE: 60
ttcacacgtg atggtgatgg tga                                         23

<210> SEQ ID NO 61
<211> LENGTH: 23
<212> TYPE: DNA
<213> ORGANISM: Nicotiana tabacum
<220> FEATURE:
<223> OTHER INFORMATION: Table 2: FK1097-F

<400> SEQUENCE: 61
tccctcagca cattccagca gat                                         23

<210> SEQ ID NO 62
<211> LENGTH: 24
<212> TYPE: DNA
<213> ORGANISM: Nicotiana tabacum
<220> FEATURE:
<223> OTHER INFORMATION: Table 2: FK1098-F

<400> SEQUENCE: 62
aacgattcct ggacctgcct catc                                        24

<210> SEQ ID NO 63
<211> LENGTH: 22
<212> TYPE: DNA
<213> ORGANISM: Nicotiana tabacum
<220> FEATURE:
<223> OTHER INFORMATION: Table 2: FK1095-F

<400> SEQUENCE: 63
cacacttcac ttggtcttgc gt                                          22
```

<210> SEQ ID NO 64
<211> LENGTH: 24
<212> TYPE: DNA
<213> ORGANISM: Nicotiana tabacum
<220> FEATURE:
<223> OTHER INFORMATION: Table 2: FK1096-R

<400> SEQUENCE: 64
tagtctttcc ggtgagagtc ttca                                              24

<210> SEQ ID NO 65
<211> LENGTH: 21
<212> TYPE: DNA
<213> ORGANISM: Nicotiana tabacum
<220> FEATURE:
<223> OTHER INFORMATION: Table 2: FK1105-F

<400> SEQUENCE: 65
atcttctggg gactatgggg a                                                 21

<210> SEQ ID NO 66
<211> LENGTH: 22
<212> TYPE: DNA
<213> ORGANISM: Nicotiana tabacum
<220> FEATURE:
<223> OTHER INFORMATION: Table 2: FK1106-R

<400> SEQUENCE: 66
tcatccttca agaagcaaag gc                                                22

<210> SEQ ID NO 67
<211> LENGTH: 22
<212> TYPE: DNA
<213> ORGANISM: Nicotiana tabacum
<220> FEATURE:
<223> OTHER INFORMATION: Table 2: FK1107-F

<400> SEQUENCE: 67
tcatacacgc cagaactctt tc                                                22

<210> SEQ ID NO 68
<211> LENGTH: 24
<212> TYPE: DNA
<213> ORGANISM: Nicotiana tabacum
<220> FEATURE:
<223> OTHER INFORMATION: Table 2: FK1108-R

<400> SEQUENCE: 68
ccaaccgata cttatccatc tcta                                              24

<210> SEQ ID NO 69
<211> LENGTH: 24
<212> TYPE: DNA
<213> ORGANISM: Nicotiana tabacum
<220> FEATURE:
<223> OTHER INFORMATION: Table 2: FK1122-F

<400> SEQUENCE: 69
ccggattctt catcttctct ctct                                              24

<210> SEQ ID NO 70
<211> LENGTH: 27
<212> TYPE: DNA
<213> ORGANISM: Nicotiana tabacum
<220> FEATURE:
<223> OTHER INFORMATION: Table 2: FK1123-R

<400> SEQUENCE: 70
cctaagcgag aatcatacca ctagacc                                              27

<210> SEQ ID NO 71
<211> LENGTH: 25
<212> TYPE: DNA
<213> ORGANISM: Nicotiana tabacum
<220> FEATURE:
<223> OTHER INFORMATION: Table 2: FK1124-F

<400> SEQUENCE: 71
gttacagtag cagagaggtc ttaca                                                25

<210> SEQ ID NO 72
<211> LENGTH: 22
<212> TYPE: DNA
<213> ORGANISM: Nicotiana tabacum
<220> FEATURE:
<223> OTHER INFORMATION: Table 2: FK1125-R

<400> SEQUENCE: 72
cgagttcaat tctcggaatg cc                                                   22

<210> SEQ ID NO 73
<211> LENGTH: 24
<212> TYPE: DNA
<213> ORGANISM: Nicotiana tabacum
<220> FEATURE:
<223> OTHER INFORMATION: Table 2: FK1126-F

<400> SEQUENCE: 73
caacagacca aactaagaaa gctc                                                 24

<210> SEQ ID NO 74
<211> LENGTH: 22
<212> TYPE: DNA
<213> ORGANISM: Nicotiana tabacum
<220> FEATURE:
<223> OTHER INFORMATION: Table 2: FK1125-R

<400> SEQUENCE: 74
cgagttcaat tctcggaatg cc                                                   22

<210> SEQ ID NO 75
<211> LENGTH: 27
<212> TYPE: DNA
<213> ORGANISM: Nicotiana tabacum
<220> FEATURE:
<223> OTHER INFORMATION: Table 2: FK1127-F

<400> SEQUENCE: 75
cctttagaag atactcgatt tggtgtc                                              27

<210> SEQ ID NO 76
<211> LENGTH: 23
<212> TYPE: DNA
<213> ORGANISM: Nicotiana tabacum
<220> FEATURE:
<223> OTHER INFORMATION: Table 2: FK1128-R

<400> SEQUENCE: 76
gtctgattag aagtcagacg cct                                                  23

<210> SEQ ID NO 77

```
<210> SEQ ID NO 77
<211> LENGTH: 20
<212> TYPE: DNA
<213> ORGANISM: Nicotiana tabacum
<220> FEATURE:
<223> OTHER INFORMATION: Table 2: FK1129-F

<400> SEQUENCE: 77
cgacataaaa gcaccgttcc                                                   20

<210> SEQ ID NO 78
<211> LENGTH: 19
<212> TYPE: DNA
<213> ORGANISM: Nicotiana tabacum
<220> FEATURE:
<223> OTHER INFORMATION: Table 2: FK1130-R

<400> SEQUENCE: 78
ggcccaatgg ataaggcgt                                                    19

<210> SEQ ID NO 79
<211> LENGTH: 21
<212> TYPE: DNA
<213> ORGANISM: Nicotiana tabacum
<220> FEATURE:
<223> OTHER INFORMATION: Table 2: FK1131-F

<400> SEQUENCE: 79
cagtgcagct gcttgagaag a                                                 21

<210> SEQ ID NO 80
<211> LENGTH: 21
<212> TYPE: DNA
<213> ORGANISM: Nicotiana tabacum
<220> FEATURE:
<223> OTHER INFORMATION: Table 2: FK1132-R

<400> SEQUENCE: 80
gtcttccccc ttaaccactc g                                                 21

<210> SEQ ID NO 81
<211> LENGTH: 20
<212> TYPE: DNA
<213> ORGANISM: Nicotiana tabacum
<220> FEATURE:
<223> OTHER INFORMATION: Table 2: FK1133-F

<400> SEQUENCE: 81
ggtttgcccg agtggttaag                                                   20

<210> SEQ ID NO 82
<211> LENGTH: 21
<212> TYPE: DNA
<213> ORGANISM: Nicotiana tabacum
<220> FEATURE:
<223> OTHER INFORMATION: Table 2: FK1134-R

<400> SEQUENCE: 82
gacaaggtgc agcttctttg a                                                 21

<210> SEQ ID NO 83
<211> LENGTH: 25
<212> TYPE: DNA
<213> ORGANISM: Nicotiana tabacum
<220> FEATURE:
<223> OTHER INFORMATION: Table 2: FK1135-F

<400> SEQUENCE: 83
```

```
ctctgaacaa gaagaaggat taagg                                      25

<210> SEQ ID NO 84
<211> LENGTH: 20
<212> TYPE: DNA
<213> ORGANISM: Nicotiana tabacum
<220> FEATURE:
<223> OTHER INFORMATION: Table 2: FK1136-R

<400> SEQUENCE: 84
ccttagacca ctcggccatc                                            20

<210> SEQ ID NO 85
<211> LENGTH: 24
<212> TYPE: DNA
<213> ORGANISM: Nicotiana tabacum
<220> FEATURE:
<223> OTHER INFORMATION: Table 2: FK1137-F

<400> SEQUENCE: 85
gacttctacg gataaagact ctga                                       24

<210> SEQ ID NO 86
<211> LENGTH: 20
<212> TYPE: DNA
<213> ORGANISM: Nicotiana tabacum
<220> FEATURE:
<223> OTHER INFORMATION: Table 2: FK1138-R

<400> SEQUENCE: 86
tctaaggcgc cagactcaag                                            20

<210> SEQ ID NO 87
<211> LENGTH: 21
<212> TYPE: DNA
<213> ORGANISM: Nicotiana tabacum
<220> FEATURE:
<223> OTHER INFORMATION: Table 2: FK1139-F

<400> SEQUENCE: 87
gcctcctgct gcttaaactc t                                          21

<210> SEQ ID NO 88
<211> LENGTH: 20
<212> TYPE: DNA
<213> ORGANISM: Nicotiana tabacum
<220> FEATURE:
<223> OTHER INFORMATION: Table 2: FK1140-R

<400> SEQUENCE: 88
gtaagcggga ggtcttgagt                                            20

<210> SEQ ID NO 89
<211> LENGTH: 21
<212> TYPE: DNA
<213> ORGANISM: Nicotiana tabacum
<220> FEATURE:
<223> OTHER INFORMATION: Table 2: FK1141-F

<400> SEQUENCE: 89
gctccaaagg caaaagcaaa c                                          21

<210> SEQ ID NO 90
<211> LENGTH: 20
<212> TYPE: DNA
```

<213> ORGANISM: Nicotiana tabacum
<220> FEATURE:
<223> OTHER INFORMATION: Table 2: FK1142-R

<400> SEQUENCE: 90
aacgggtgct ctaaccaact                                              20

<210> SEQ ID NO 91
<211> LENGTH: 20
<212> TYPE: DNA
<213> ORGANISM: Nicotiana tabacum
<220> FEATURE:
<223> OTHER INFORMATION: Table 2: FK1143-F

<400> SEQUENCE: 91
gctagcgcgt aggtctcata                                              20

<210> SEQ ID NO 92
<211> LENGTH: 20
<212> TYPE: DNA
<213> ORGANISM: Nicotiana tabacum
<220> FEATURE:
<223> OTHER INFORMATION: Table 2: FK1144-R

<400> SEQUENCE: 92
gaagcaaagc tgccgagatg                                              20

<210> SEQ ID NO 93
<211> LENGTH: 20
<212> TYPE: DNA
<213> ORGANISM: Nicotiana tabacum
<220> FEATURE:
<223> OTHER INFORMATION: Table 2: FK1143-F

<400> SEQUENCE: 93
gctagcgcgt aggtctcata                                              20

<210> SEQ ID NO 94
<211> LENGTH: 20
<212> TYPE: DNA
<213> ORGANISM: Nicotiana tabacum
<220> FEATURE:
<223> OTHER INFORMATION: Table 2: FK1145-R

<400> SEQUENCE: 94
ttctccaccg tccatgcaat                                              20

<210> SEQ ID NO 95
<211> LENGTH: 20
<212> TYPE: DNA
<213> ORGANISM: Nicotiana tabacum
<220> FEATURE:
<223> OTHER INFORMATION: Table 2: FK1146-F

<400> SEQUENCE: 95
cgctcgctag agaggaccat                                              20

<210> SEQ ID NO 96
<211> LENGTH: 20
<212> TYPE: DNA
<213> ORGANISM: Nicotiana tabacum
<220> FEATURE:
<223> OTHER INFORMATION: Table 2: FK1147-R

<400> SEQUENCE: 96
gacctacgcg ctagccaact                                              20

<210> SEQ ID NO 97
<211> LENGTH: 23
<212> TYPE: DNA
<213> ORGANISM: Nicotiana tabacum
<220> FEATURE:
<223> OTHER INFORMATION: Table 2: FK1148-F

<400> SEQUENCE: 97
ctgaaactga atcttgcctg gag                                        23

<210> SEQ ID NO 98
<211> LENGTH: 22
<212> TYPE: DNA
<213> ORGANISM: Nicotiana tabacum
<220> FEATURE:
<223> OTHER INFORMATION: Table 2: FK1149-R

<400> SEQUENCE: 98
ggactctgaa tccagtaacc cg                                         22

<210> SEQ ID NO 99
<211> LENGTH: 20
<212> TYPE: DNA
<213> ORGANISM: Nicotiana tabacum
<220> FEATURE:
<223> OTHER INFORMATION: Table 2: FK1152-F

<400> SEQUENCE: 99
actttcatca gccgttttga                                            20

<210> SEQ ID NO 100
<211> LENGTH: 22
<212> TYPE: DNA
<213> ORGANISM: Nicotiana tabacum
<220> FEATURE:
<223> OTHER INFORMATION: Table 2: FK1153-R

<400> SEQUENCE: 100
acgattggtt gaatatcatc ag                                         22

<210> SEQ ID NO 101
<211> LENGTH: 84
<212> TYPE: DNA
<213> ORGANISM: Nicotiana tabacum
<220> FEATURE:
<223> OTHER INFORMATION: Fig 5: tRNAmet

<400> SEQUENCE: 101
tgaattatca gagtggcgca gcggaagcgt ggtgggccca taacccacag gtcccaggat    60
cgaaacctgg ctctgatatc taga                                         84

<210> SEQ ID NO 102
<211> LENGTH: 83
<212> TYPE: DNA
<213> ORGANISM: Nicotiana tabacum
<220> FEATURE:
<223> OTHER INFORMATION: Fig 5: tRNAgly

<400> SEQUENCE: 102
tgaattgcac cagtggtcta gtggcatgat agtaccctgc cacggtacag acccgggttc    60
aattcccggc tggtgcatct aga                                          83

<210> SEQ ID NO 103

```
<211> LENGTH: 85
<212> TYPE: DNA
<213> ORGANISM: Nicotiana tabacum
<220> FEATURE:
<223> OTHER INFORMATION: Fig 5: tRNAIle

<400> SEQUENCE: 103
tgaattgctc ccgtagctca gttggttaga gcgttggtct tatgagccga aggtcgcggg    60
ttcgagcccc gccggaagct ctaga                                          85

<210> SEQ ID NO 104
<211> LENGTH: 71
<212> TYPE: DNA
<213> ORGANISM: Nicotiana tabacum
<220> FEATURE:
<223> OTHER INFORMATION: Fig 5: tRNAmet D-loop

<400> SEQUENCE: 104
tgaattatca gagtggtggt gggcccataa cccacaggtc ccaggatcga aacctggctc    60
tgatatctag a                                                         71

<210> SEQ ID NO 105
<211> LENGTH: 56
<212> TYPE: DNA
<213> ORGANISM: Nicotiana tabacum
<220> FEATURE:
<223> OTHER INFORMATION: Fig 5: tRNAmet DA-loop

<400> SEQUENCE: 105
tgaattatca gagtggtggc aggtcccagg atcgaaacct ggctctgata tctaga        56

<210> SEQ ID NO 106
<211> LENGTH: 56
<212> TYPE: DNA
<213> ORGANISM: Nicotiana tabacum
<220> FEATURE:
<223> OTHER INFORMATION: Fig 5: tRNAmet DT-loop

<400> SEQUENCE: 106
tgaattatca gagtggtggt gggcccataa cccacaggtc cgctctgata tctaga        56

<210> SEQ ID NO 107
<211> LENGTH: 54
<212> TYPE: DNA
<213> ORGANISM: Nicotiana tabacum
<220> FEATURE:
<223> OTHER INFORMATION: Fig 5: tRNAmet AT-loop

<400> SEQUENCE: 107
tgaattatca gagtggcgca gcggaagcgt ggcaggtccg ctctgatatc taga          54

<210> SEQ ID NO 108
<211> LENGTH: 72
<212> TYPE: RNA
<213> ORGANISM: Nicotiana tabacum
<220> FEATURE:
<223> OTHER INFORMATION: Fig 8: tRNAmet

<400> SEQUENCE: 108
aucagagugg cgcagcggaa gcgguguggg cccauaaccc acagguccca ggaucgaaac    60
cuggcucuga ua                                                        72

<210> SEQ ID NO 109
<211> LENGTH: 70
```

```
<212> TYPE: RNA
<213> ORGANISM: Nicotiana tabacum
<220> FEATURE:
<223> OTHER INFORMATION: Fig 8: tRNAgly

<400> SEQUENCE: 109
gcaccagugg ucuaguggca ugauaguacc cugccacggu acagacccgg guucaauucc    60
cggcuggugc                                                           70

<210> SEQ ID NO 110
<211> LENGTH: 73
<212> TYPE: RNA
<213> ORGANISM: Nicotiana tabacum
<220> FEATURE:
<223> OTHER INFORMATION: Fig 8: tRNA Ile

<400> SEQUENCE: 110
gcucccguag cucaguuggu uagagcguug gucuuaugag ccgaaggucg cggguucgag    60
ccccgccgga agc                                                      73

<210> SEQ ID NO 111
<211> LENGTH: 84
<212> TYPE: RNA
<213> ORGANISM: Nicotiana tabacum
<220> FEATURE:
<223> OTHER INFORMATION: Fig:7G GUS:: tRNAmet

<400> SEQUENCE: 111
ugaauuauca gaguggcgca gcggaagcgu gguggggccca uaacccacag gucccaggau    60
cgaaaccugg cucugauauc uaga                                          84

<210> SEQ ID NO 112
<211> LENGTH: 56
<212> TYPE: RNA
<213> ORGANISM: Nicotiana tabacum
<220> FEATURE:
<223> OTHER INFORMATION: Fig:7G GUS:: tRNAmet deltaD/T loop/stem

<400> SEQUENCE: 112
ugaauuauca gagugguggu gggcccauaa cccacagguc cgcucugaua ucuagu        56

<210> SEQ ID NO 113
<211> LENGTH: 54
<212> TYPE: RNA
<213> ORGANISM: Nicotiana tabacum
<220> FEATURE:
<223> OTHER INFORMATION: GUS:tRNAmet deltaA/T loop/stem

<400> SEQUENCE: 113
ugaauuauca gaguggcgca gcggaagcgu gacagguccg cucugauauc uaga          54

<210> SEQ ID NO 114
<211> LENGTH: 71
<212> TYPE: RNA
<213> ORGANISM: Nicotiana tabacum
<220> FEATURE:
<223> OTHER INFORMATION: GUS::tRNAmet deltaD loop/stem

<400> SEQUENCE: 114
ugaauuauca gagugguggu gggcccauaa cccacagguc ccaggaucga aaccuggcuc    60
ugauaucuag u                                                        71

<210> SEQ ID NO 115
```

```
<211> LENGTH: 57
<212> TYPE: RNA
<213> ORGANISM: Nicotiana tabacum
<220> FEATURE:
<223> OTHER INFORMATION: GUS::tRNAmet deltaD/a loop/stem

<400> SEQUENCE: 115
ugaauuauca gagugguggu caggucccag gaucgaaacc uggcucugau aucuagu        57

<210> SEQ ID NO 116
<211> LENGTH: 82
<212> TYPE: RNA
<213> ORGANISM: Nicotiana tabacum
<220> FEATURE:
<223> OTHER INFORMATION: GUS::tRNAgly

<400> SEQUENCE: 116
ugaauugcac caguggucua guggcaugau aguacccugc cacgguacag acccggguuc     60
aauucccggc uggugcucua ga                                             82

<210> SEQ ID NO 117
<211> LENGTH: 85
<212> TYPE: RNA
<213> ORGANISM: Nicotiana tabacum
<220> FEATURE:
<223> OTHER INFORMATION: GUS:tRNAIle

<400> SEQUENCE: 117
ugaauugcuc ccguagcuca guugguuaga gcguuggucu uaugagccga aggucgcggg     60
uucgagcccc gccggaagcu cuaga                                          85
```

UNITED STATES PATENT AND TRADEMARK OFFICE
CERTIFICATE OF CORRECTION

PATENT NO. : 11,981,901 B2
APPLICATION NO. : 17/446931
DATED : May 14, 2024
INVENTOR(S) : Friedrich Kragler et al.

Page 1 of 1

It is certified that error appears in the above-identified patent and that said Letters Patent is hereby corrected as shown below:

On the Title Page

At Item (72), please delete "Wim Verelst, De Lier (NL)".

Signed and Sealed this
Third Day of June, 2025

Coke Morgan Stewart
*Acting Director of the United States Patent and Trademark Office*